(12) United States Patent
Cundiff et al.

(10) Patent No.: US 12,419,654 B2
(45) Date of Patent: Sep. 23, 2025

(54) SURGICAL INSTRUMENTS INCLUDING A SET OF CUTTING BLADES FOR PERFORMING AN OSTEOTOMY

(71) Applicant: Fusion Orthopedics, LLC, Mesa, AZ (US)

(72) Inventors: Adam J. Cundiff, Gilbert, AZ (US); Nathan G. Peterson, Gilbert, AZ (US); Eli W. Jacobson, Chandler, AZ (US)

(73) Assignee: Fusion Orthopedics, LLC, Mesa, AZ (US)

( * ) Notice: Subject to any disclaimer, the term of this patent is extended or adjusted under 35 U.S.C. 154(b) by 328 days.

(21) Appl. No.: 18/177,572

(22) Filed: Mar. 2, 2023

(65) Prior Publication Data

US 2023/0389940 A1 Dec. 7, 2023

Related U.S. Application Data

(63) Continuation of application No. 17/832,469, filed on Jun. 3, 2022, which is a continuation-in-part of application No. 17/538,781, filed on Nov. 30, 2021, now Pat. No. 12,035,927, which is a continuation of application No. 16/537,495, filed on Aug. 9, 2019, now Pat. No. 11,253,273, which is a continuation-in-part of application No. 16/459,555, filed on Jul. 1, 2019, now Pat. No. 11,253,272.

(51) Int. Cl.
    *A61B 17/16* (2006.01)

(52) U.S. Cl.
    CPC .................. *A61B 17/1659* (2013.01)

(58) Field of Classification Search
    CPC ..... A61B 17/151; A61B 17/152; A61B 17/14; A61B 17/142; A61B 17/1659; B25D 3/006; B23D 61/006
    See application file for complete search history.

(56) References Cited

U.S. PATENT DOCUMENTS

| | | | |
|---|---|---|---|
| 4,872,452 A * | 10/1989 | Alexson | A61B 17/1659 407/29.1 |
| 5,087,261 A | 2/1992 | Ryd | |
| 6,120,508 A | 9/2000 | Grunig | |
| 8,939,981 B1 * | 1/2015 | Anderson | A61B 17/14 606/82 |
| 2007/0233131 A1 | 10/2007 | Song | |

\* cited by examiner

*Primary Examiner* — Andrew Yang

(57) ABSTRACT

Surgical instruments and methods for performing an osteotomy are disclosed herein. A surgical instrument includes a body with a distal end, a proximal end, a first surface, and a second surface. The surgical instrument can include cutting blades positioned on the first surface and the second surface. The surgical instrument can include columns of cutting blades positioned on the first surface and/or the second surface. The surgical instrument can include rows of cutting blades positioned on the first surface and/or the second surface.

20 Claims, 45 Drawing Sheets

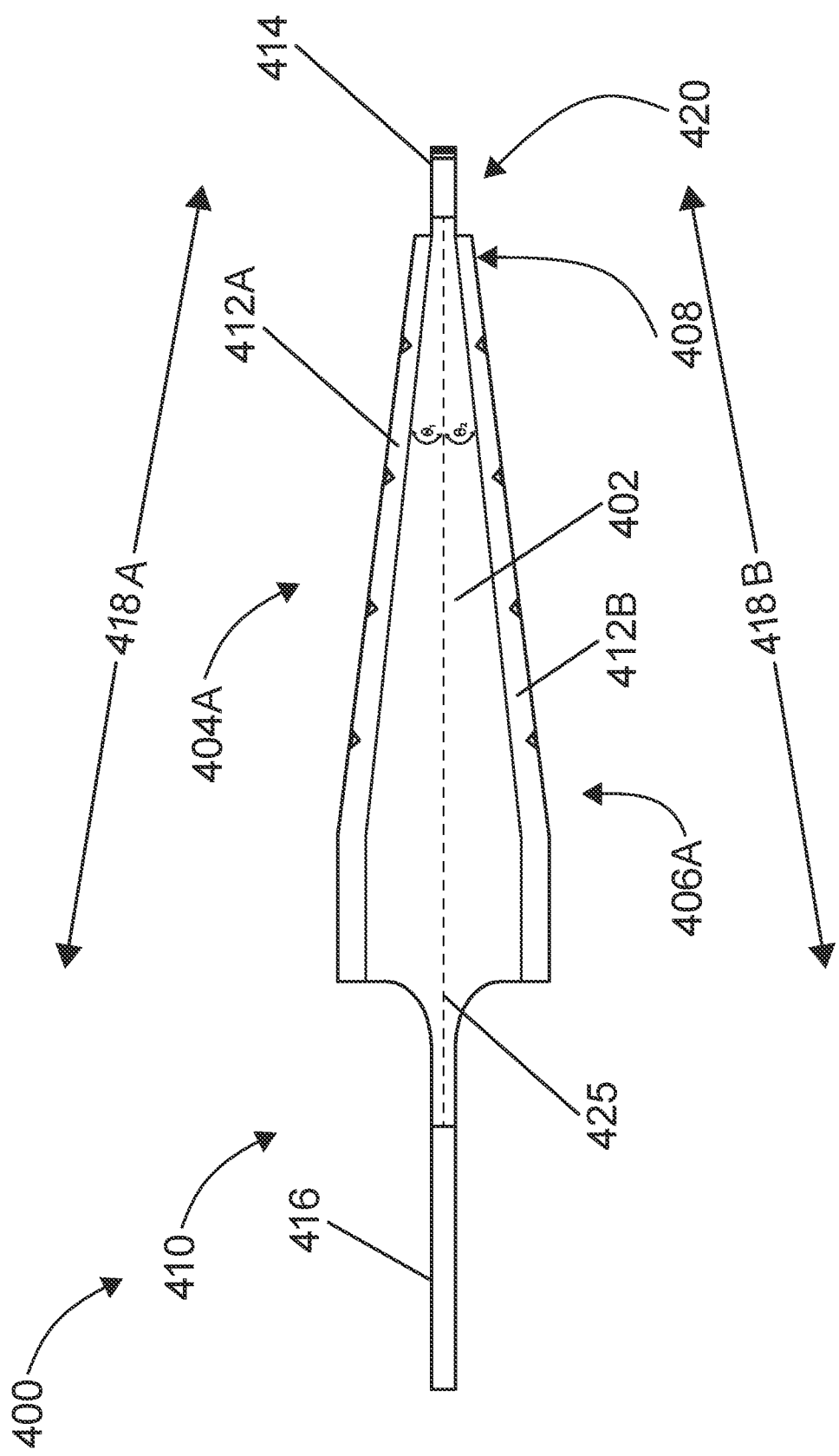

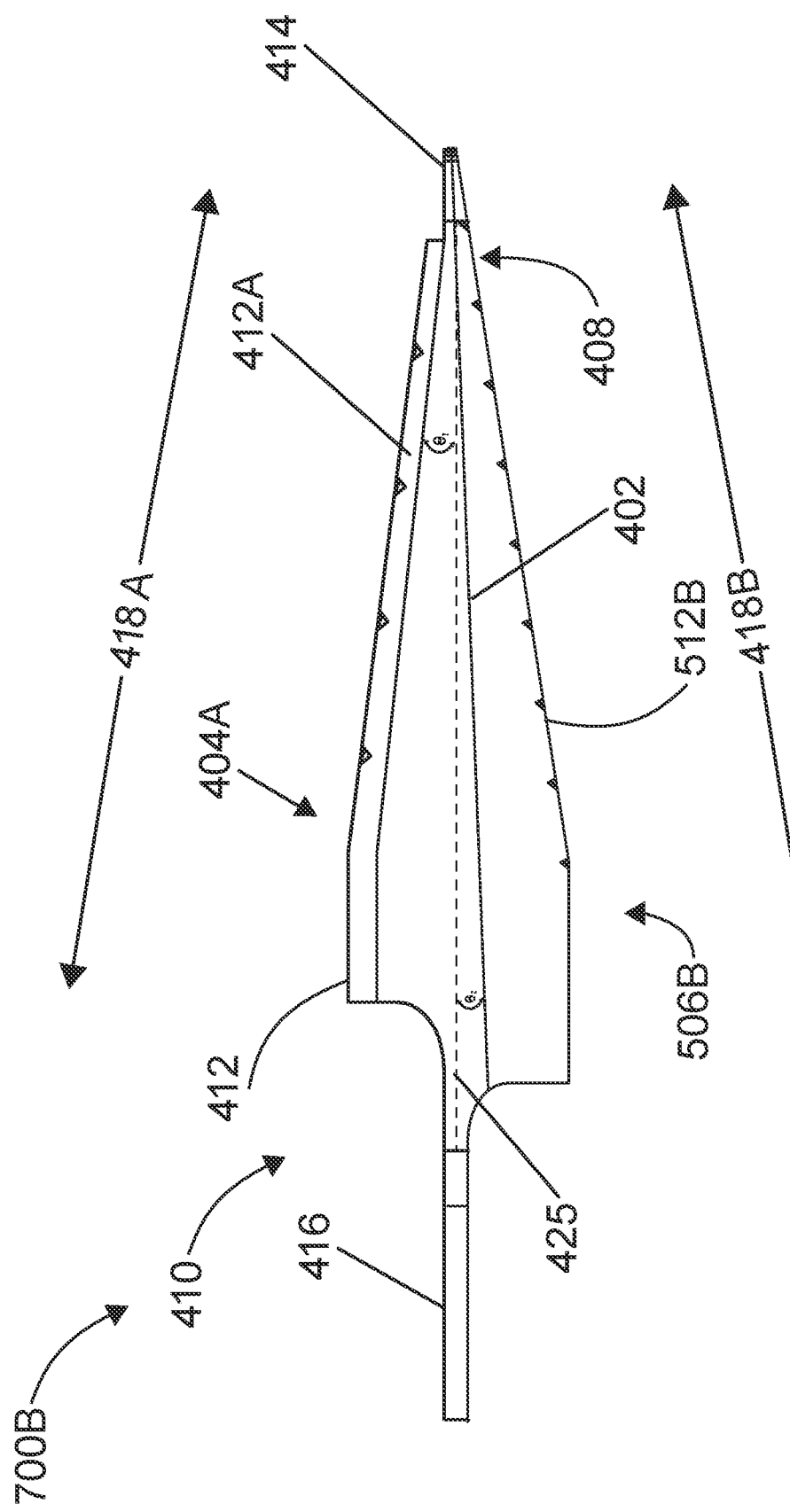

SURGICAL INSTRUMENTS INCLUDING A SET OF CUTTING BLADES FOR PERFORMING AN OSTEOTOMY

REFERENCE TO RELATED APPLICATIONS

This application is a Continuation of and claims priority to U.S. patent application Ser. No. 17/832,469, which is a Continuation-In-Part of and claims priority to U.S. patent application Ser. No. 17/538,781, filed on Nov. 30, 2021, which is a Continuation of and claims priority to U.S. patent application Ser. No. 16/537,495, now U.S. Pat. No. 11,253,273, filed on Aug. 9, 2019, which is a Continuation-In-Part of and claims priority to U.S. patent application Ser. No. 16/459,555, now U.S. Pat. No. 11,253,272, filed on Jul. 1, 2019, the contents of each of which are incorporated herein by reference in their entirety.

FIELD OF THE TECHNOLOGY

The present technology relates generally to surgical cutting apparatus, and more particularly to, surgical instruments for performing osteotomies.

BACKGROUND

Surgical cutting instruments come in many shapes and sizes. In performing an osteotomy with a single-sided device, the user (e.g., a physician, surgeon, etc.) is often required to perform multiple cuts and/or passes to achieve a desired shape and/or osteotomy. Further, multiple cuts and/or passes with using a surgical instrument can result in inconsistencies in shape and/or size of the resulting osteotomy in different patients. In other words, it takes more time to perform a osteotomy than is otherwise needed and/or there is a degree of inconsistency and/or inaccuracy when a traditional surgical instrument is utilized to perform an osteotomy.

SUMMARY

Various embodiments provide surgical instruments and methods for performing an osteotomy. A surgical instrument includes a body with a distal end, a proximal end, a first surface, and a second surface. The surgical instrument can include cutting blades positioned on the first surface and the second surface. The surgical instrument can include columns of cutting blades positioned on the first surface and/or the second surface. The surgical instrument can include rows of cutting blades positioned on the first surface and/or the second surface.

BRIEF DESCRIPTION OF THE DRAWINGS

To readily understand the advantages and benefits of the technology, a more particular description of the technology briefly described above will be rendered by reference to specific embodiments that are illustrated in the appended drawings. Understanding that these drawings depict typical embodiments of the technology, and are therefore not to be considered to be limiting of its scope, the technology will be described and explained with additional specificity and detail through the use of the accompanying drawings, in which:

FIGS. 4A through 4F are schematic diagrams illustrating various embodiments of a double-sided surgical instrument including multiple columns of cutting blades;

FIGS. 7A through 7D are schematic diagram illustrating various embodiments of a double-sided surgical instrument including multiple rows of cutting blades and multiple columns of cutting blades;

DETAILED DESCRIPTION OF THE DRAWINGS

Figure 1A:
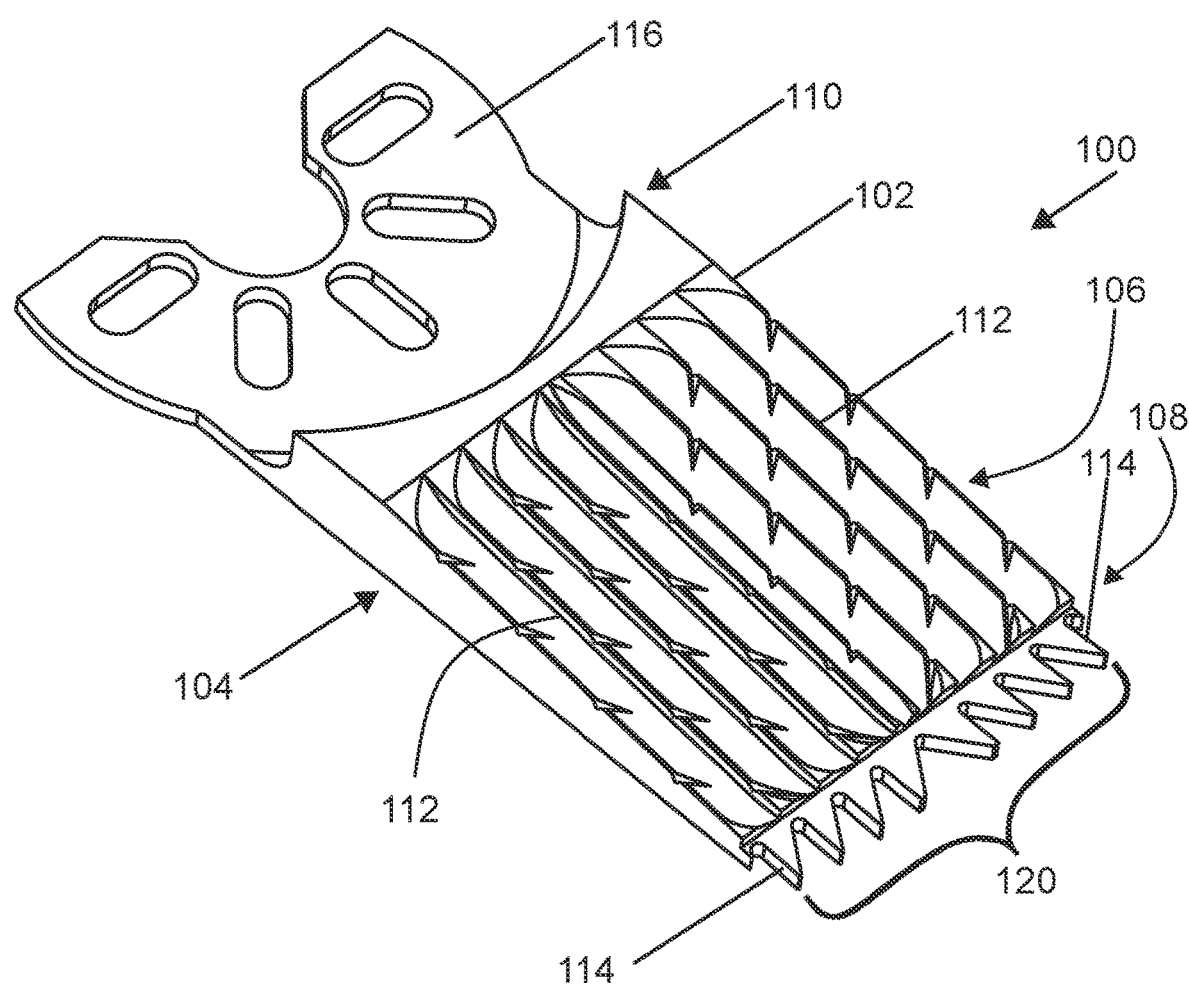
FIGS. 1A through 1D are schematic diagrams illustrating various embodiments of a surgical instrument including multiple columns of cutting blades.
Figure 1B:
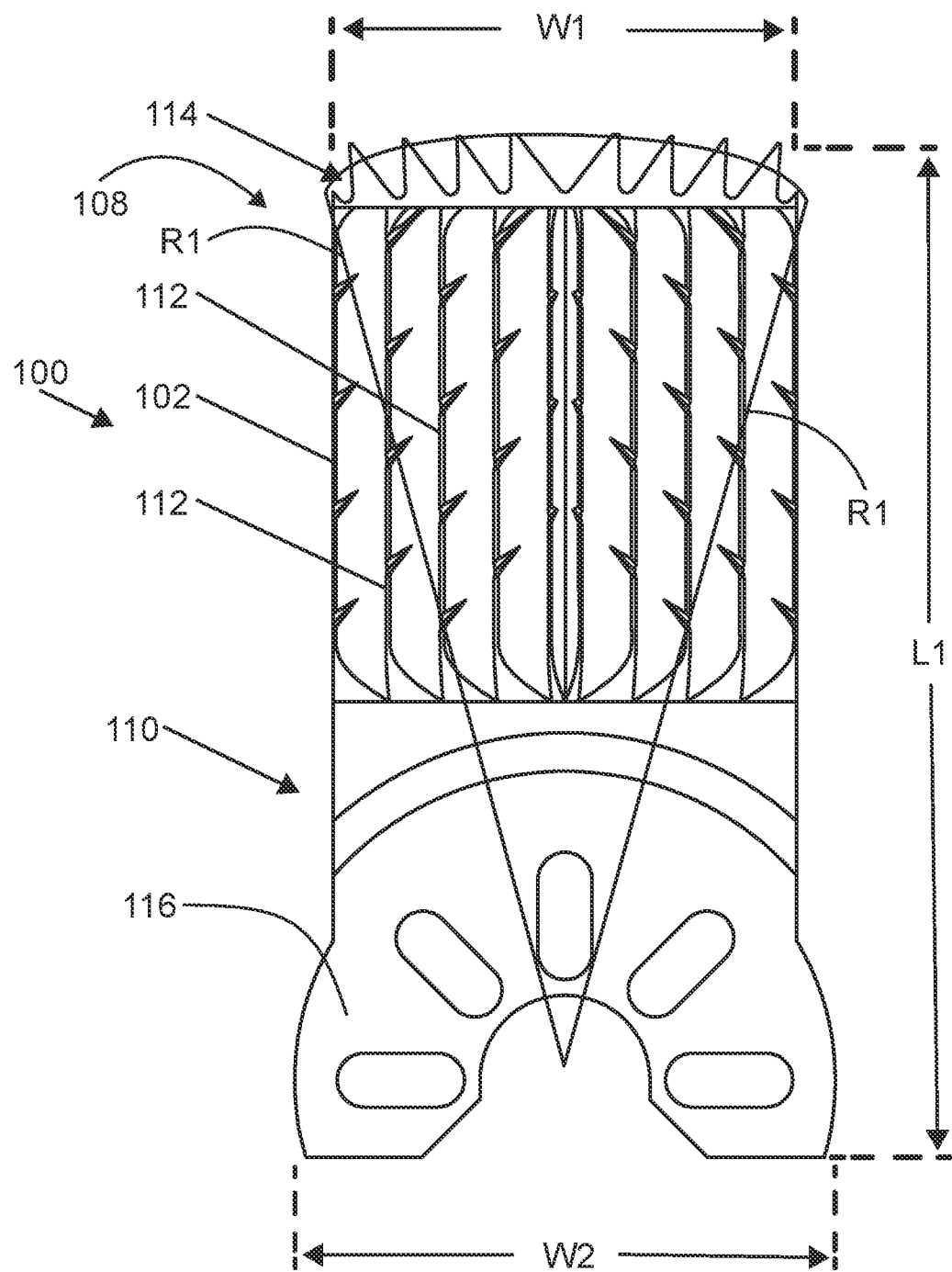

It should be understood that the language used in the present disclosure has been principally selected for readability and instructional purposes, and not to limit the scope of the subject matter disclosed herein in any manner. Further, reference throughout this specification to "one embodiment," "an embodiment," or similar language means that a particular feature, structure, or characteristic described in connection with the embodiment is included in at least one embodiment. Thus, appearances of the phrases "in one embodiment," "in an embodiment," and similar language throughout this specification may, but do not necessarily, all refer to the same embodiment, but mean "one or more but not all embodiments" unless expressly specified otherwise. The terms "including," "comprising," "having," and variations thereof mean "including, but not limited to" unless expressly specified otherwise. An enumerated listing of items does not imply that any or all of the items are mutually exclusive and/or mutually inclusive, unless expressly specified otherwise. The terms "a," "an," and "the" also refer to "one or more" unless expressly specified otherwise.

In addition, as used herein, the term "set" can mean "one or more," unless expressly specified otherwise. The term "sets" can mean multiples of or a plurality of "one or mores," "ones or more," and/or "ones or mores" consistent with set theory, unless expressly specified otherwise.

Furthermore, the described features, advantages, and characteristics of the embodiments may be combined in any suitable manner. One skilled in the relevant art will recognize that the embodiments may be practiced without one or more of the specific features or advantages of a particular embodiment. In other instances, additional features and advantages may be recognized in certain embodiments that may not be present in all embodiments. Aspects of the embodiments are described below with reference to schematic flowchart diagrams and/or schematic block diagrams of methods, apparatuses, and systems according to embodiments. The schematic flowchart diagrams and/or schematic block diagrams in the Figures illustrate the structure, functionality, and operation of possible implementations of apparatuses, systems, and methods according to various embodiments.

It should also be noted that, in some alternative implementations, the functions noted in the block may occur out of the order noted in the Figures. For example, two blocks shown in succession may, in fact, be executed substantially concurrently, or the blocks may sometimes be executed in the reverse order. Other steps and methods may be conceived that are equivalent in function, logic, or effect to one or more blocks, or portions thereof, of the illustrated Figures.

Although various arrow types and line types may be employed in the flowchart and/or block diagrams, they are understood not to limit the scope of the corresponding embodiments. Indeed, some arrows or other connectors may be used to indicate only the logical flow of the depicted embodiment. For instance, an arrow may indicate a waiting or monitoring period of unspecified duration between enumerated steps of the depicted embodiment. It will also be noted that each block of the block diagrams and/or flowchart diagrams, and combinations of blocks in the block diagrams and/or flowchart diagrams, can be implemented by special purpose hardware-based systems that perform the specified functions or acts, or combinations of special purpose hardware and code.

The present technology may include any type of surgical instrument and is not limited to the style of surgical instrument depicted in the drawings. Furthermore, the described features, structures, or characteristics of the various embodiments may be combined in any suitable manner. One skilled in the relevant art will recognize, however, that embodiments may be practiced without one or more of the specific details, or with other methods, components, materials, and so forth. In other instances, well-known structures, and/or materials are not shown or described in detail to avoid obscuring aspects of an embodiment.

Turning now to the Figures, FIGS. 1A through 1D are schematic diagrams illustrating various views of one embodiment of a surgical instrument 100. In various embodiments, the surgical instrument 100 can be utilized to perform a wedge-shaped osteotomy. Further, the wedge-shaped osteotomy can be achieved with a single cut or pass utilizing the surgical instrument 100.

A surgical instrument 100 may be constructed of any suitable material that can cut bone. In various embodiments, the surgical instrument 100 is constructed of a sterilized suitable material that can cut bone. In some embodiments, the surgical instrument 100 includes stainless steel, among other suitable materials that are possible and contemplated herein. In additional or alternative embodiments, the surgical instrument 100 includes surgical grade stainless steel, among other suitable surgical grade materials that are possible and contemplated herein.

At least in the illustrated embodiment, the surgical instrument 100 includes, among other features, a body 102 including at least a bottom surface 104, a top surface 106, a distal end 108, and a proximal end 110, a set of cutting blades 112 positioned on the body 102, a set of cutting teeth 114 positioned on the distal end 108, and an attachment mechanism 116 positioned on the proximal end 110. A body 102 may include any suitable dimensions that can perform an osteotomy. In various embodiments, the body 102 includes dimensions that are suitable for performing an osteotomy on a human.

In various embodiments, the body 102 includes a length L1 (see FIG. 1B) in the range of about 15 mm to about 70 mm, among other ranges of length and/or lengths that are possible and contemplated herein. In some embodiments, the body 102 includes a length L1 of about 20 mm, among other lengths that are possible and contemplated herein.

The body 102 further includes a width W1 (see FIG. 1B) at the distal end 108 and a width W2 (see FIG. 1B) at the proximal end 110. In various embodiments, the width W1 is in the range of about 5 mm to about 30 mm, among other ranges of widths and/or widths that are possible and contemplated herein. In some embodiments, the width W1 is about 7.5 mm, among other widths that are possible and contemplated herein. In additional or alternative embodiments, the width W2 is in the range of about 5 mm to about 70 mm, among other ranges of widths and/or widths that are possible and contemplated herein. In some embodiments, the width W2 is about 11 mm, among other widths that are possible and contemplated herein.

In some embodiments, the width W1 and the width W2 are the same width or substantially the same width. In other embodiments, the width W2 is greater than the width W1 such that the proximate end 110 is wider than the distal end 108 or, alternatively, the distal end 108 is narrower than the proximate end 110 (e.g., the width W1 is less than the width W2). That is, in various embodiments, the surgical instrument 100 includes a tapered shape and/or tapers from the distal end 108 to the proximate end 110.

A bottom surface 104 may include any suitable shape and/or profile that can facilitate or assist the surgical instrument 100 in performing an osteotomy (e.g., a wedge-shaped osteotomy). In various embodiments, the bottom surface 104 includes a flat or substantially flat surface, among other profiles and/or planes that are possible and contemplated herein.

A top surface 106 may include any suitable profile upon which one or more cutting blades 112 can be positioned. In various embodiments, the top surface 106 includes a slope 118 (see FIGS. 1C and 1D) that extends upward and/or away from the bottom surface 104 and the distal end 108. The slope 118 may include any suitable grade (e.g., rise over run) that can facilitate and/or assist the surgical instrument 100 in performing an osteotomy and particularly, a wedge-shaped osteotomy. That is, the top surface 106 and/or surgical instrument 100 may include any suitable grade that can facilitate and/or assist the surgical instrument 100 in performing a wedge-shaped osteotomy in one cut and/or one pass.

Figure 1C:
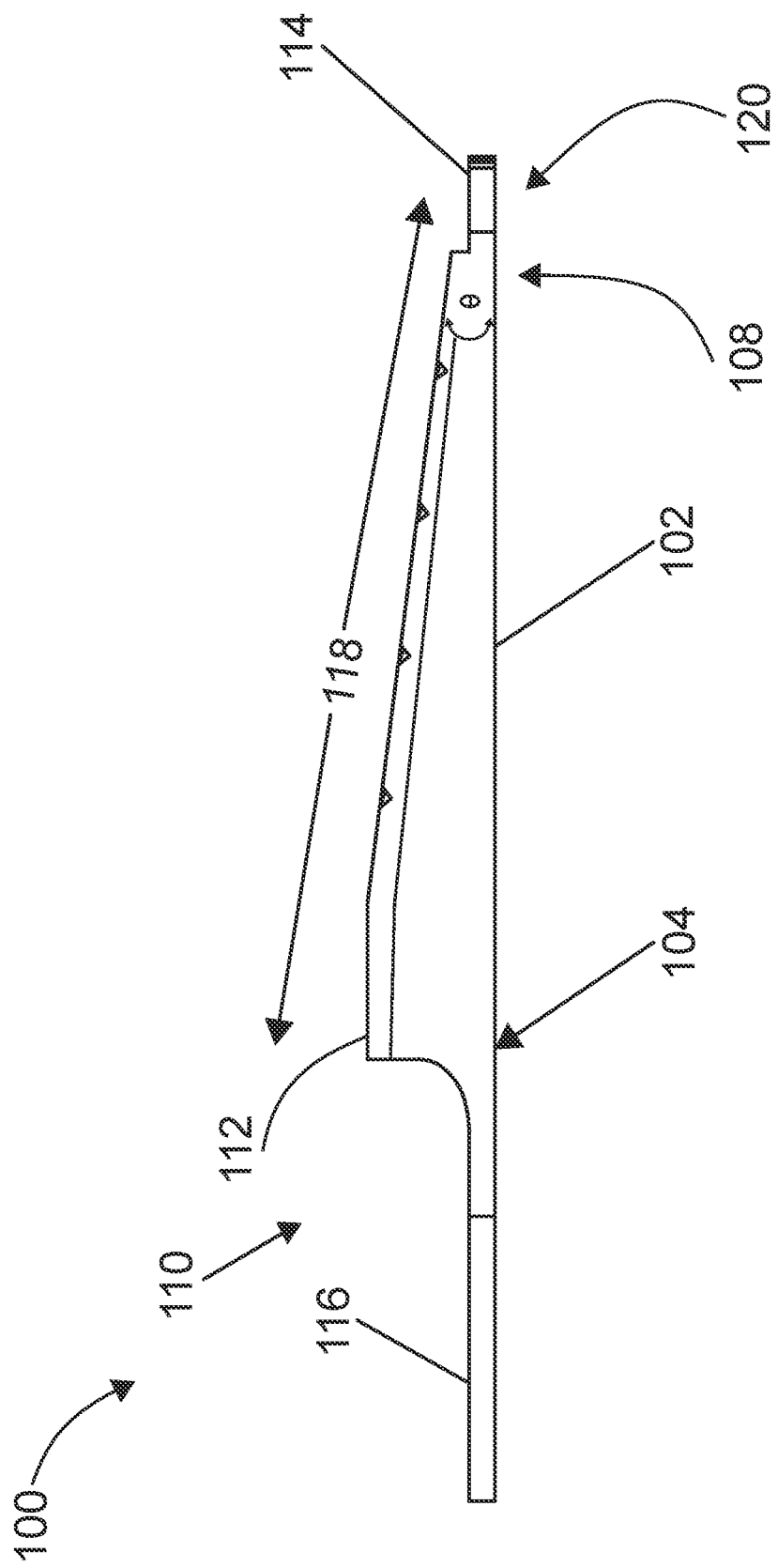
Figure 1D:
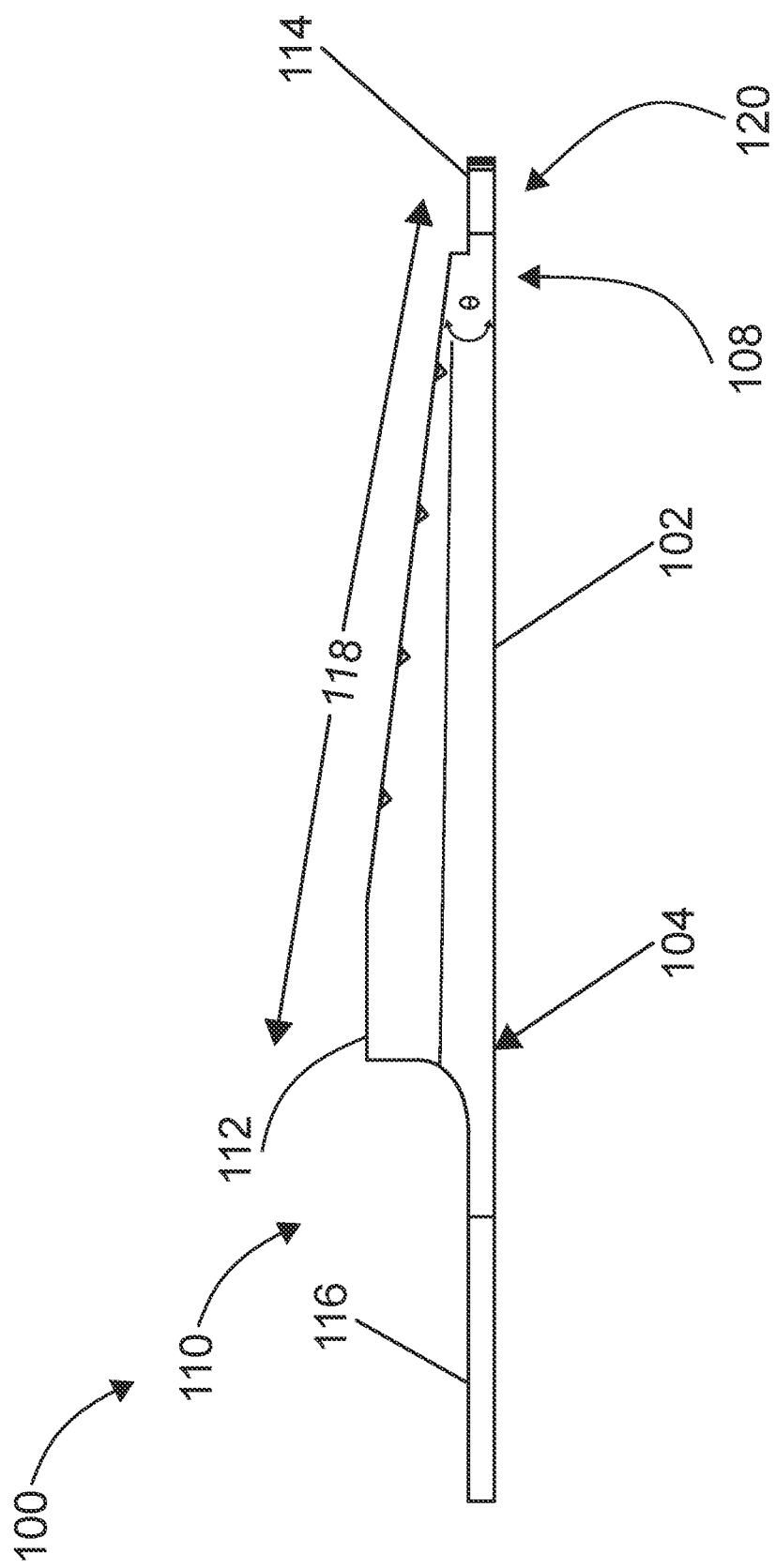

In various embodiments, the slope 118 includes a grade in the range of about zero degrees (0° or flat) to about fifteen degrees (15°), among other ranges of grades, grades, and/or slopes that are possible and contemplated herein. In other words, an angle θ in the range of about 0° to about 15° (e.g., the angle θ=0°, 1°, 2°, 3°, 4°, 5°, 6°, 7°, 8°, 9°, 10°, 11°, 12°, 13°, 14°, or 15° and/or the angle θ≈0°, 1°, 2°, 3°, 4°, 5°, 6°, 7°, 8°, 9°, 10°, 11°, 12°, 13°, 14°, or 15°) is defined between the top surface 106 and the bottom surface 104 beginning at the distal end 108 and extending upward and toward the proximate end 110, as shown in FIGS. 1C and 1D. In some embodiments, the slope 118 includes a grade of about seven (7°) degrees (e.g., the angle θ=7° or the angle θ 7°), among other suitable grades and/or slopes that are possible and contemplated herein.

In several embodiments, the top surface 106 includes a set of cutting blades 112 positioned thereon. As illustrated, the set of cutting blades 112 are spaced apart and positioned vertically to form a set of columns of cutting blades 112.

A set of cutting blades 112 may include any suitable quantity of cutting blades 112 and/or quantity of columns of cutting blades 112 that can facilitate and/or assist the surgical instrument 100 in performing an osteotomy and particularly, a wedge-shaped osteotomy. In various embodiments, the top surface 106 includes a suitable quantity of cutting blades 112 so that the surgical instrument 100 can perform a wedge-shaped osteotomy in one cut and/or one pass.

In various embodiments, the top surface 106 includes a quantity of cutting blades 112 in the range of about 2 cutting blades 112 to about 40 cutting blades 112, among other ranges of quantities of cutting blades 112 and/or quantities of cutting blades 112 that are possible and contemplated herein. In some embodiments, the top surface 106 includes 12 cutting blades 112, among other quantities of cutting blades 112 that are possible and contemplated herein.

While the surgical instrument 100 is shown with a top surface 106 including 8 cutting blades 112, the various embodiments of the surgical instrument 100 are not limited to 8 cutting blades 112. That is, various other embodiments of a surgical instrument 100 can include a different quantity of cutting blades 112 such that the top surface 106 can include a greater quantity of cutting blades 112 than 8 cutting blades 112 or a smaller quantity of cutting blades 112 than 8 cutting blades 112.

In some embodiments, the cutting blades 112 may be included on the entirety or substantially the entirety of the top surface 106. In other embodiments, the cutting blades 112 may be included on a portion or at least a portion of the top surface 106. That is, the cutting blades 112 may extend partially or fully from the distal end 108 to the proximal end 110.

The portion of the top surface 106 including the cutting blades 112 may include any suitable sized portion that can produce a wedge-shaped osteotomy. Various embodiments of the surgical instrument 100 may include varying sized portions of the top surface 106 including the cutting blades 112 so that different sized and/or wedge-shaped osteotomies can be obtained. That is, different embodiments may include cutting blades 112 with differing lengths to produce different sized and/or wedge-shaped osteotomies.

A cutting blade 112 may include any suitable shape that can facilitate and/or assist the surgical instrument 100 in performing an osteotomy (e.g., a wedge-shaped osteotomy). In various embodiments, a cutting blade 112 can include a curved blade (e.g., a vertically curved blade), a straight blade, waved blade (e.g., a horizontally curved blade), or a wavy blade (e.g., a blade with multiple horizontal curves), among other suitable shapes that can facilitate cutting bone that are possible and contemplated herein. In additional or alternative embodiments, a cutting blade 112 can include a straight cutting edge and/or a serrated cutting edge, among other cutting edges that are possible and contemplated herein.

In some embodiments, all of the cutting blades 112 in the set of cutting blades 112 on the top surface 106 include the same or substantially the same shape. In alternative embodiments, at least two cutting blades 112 in the set of cutting blades 112 on the top surface 106 include different shapes or substantially different shapes. In one non-limiting example, at least one cutting blade 112 includes a straight blade and at least one cutting blade 112 includes a curved blade (or other non-straight blade), among other shapes and/or combinations of shapes that are possible and contemplated herein. In an additional or alternative non-limiting example, the straight blade(s) and/or the curved blade(s) include a serrated cutting edge.

In additional or alternative embodiments, a set of cutting blades 112 can include at least two subsets of cutting blades 112 in which a first subset includes two or more cutting blades 112 including a first shape and at least a second subset that includes two or more cutting blades 112 including a second, different shape. In some embodiments, one or more of the cutting blades 112 in one or more of the subsets of cutting blades 112 includes a serrated edge.

In further additional or alternative embodiments, the first subset of cutting blades 112 and the second subset of cutting blades 112 include the same quantity of cutting blades 112. In other embodiments, the first subset of cutting blades 112 and the second subset of cutting blades 112 include different quantities of cutting blades 112.

In yet further additional or alternative embodiments, the cutting blades 112 in the first subset of cutting blades 112 and the cutting blades 112 in the second subset of cutting blades 112 can be positioned in a pattern. The pattern may include any suitable pattern that can assist in and/or facilitate performing an osteotomy (e.g., a wedge-shaped osteotomy). In some embodiments, the pattern may include cutting blades 112 with different shapes in an alternating pattern to provide alternating columns of cutting blades 112.

A cutting blade 112 may include any suitable height that can facilitate and/or assist the surgical instrument 100 in performing an osteotomy (e.g., a wedge-shaped osteotomy). In various embodiments, the cutting blades 112 can include a height in the range of about 0.1 mm to about 30 mm, among other suitable heights that can facilitate cutting bone that are possible and contemplated herein. In some embodiments, the cutting blades 112 include a height of 0.75 mm.

In some embodiments, all of the cutting blades 112 in the set of cutting blades 112 on the top surface 106 include a uniform height (see FIG. 1C). In alternative embodiments, one or more of the cutting blades 112 on the top surface 106 include a height that gradually increases from the distal end 108 to the proximal end 110 (see FIG. 1D).

As shown, the distal end 108 includes a set of cutting teeth 114 (e.g., a single tooth 114 or multiple teeth 114) positioned thereon. A set of cutting teeth 114 may include any suitable quantity of teeth 114 that can assist in and/or facilitate initiating an osteotomy and particularly, a wedge-shaped osteotomy, when oscillated.

In various embodiments, the set of cutting teeth 114 includes a quantity of cutting teeth 114 in the range of one (1) cutting tooth 114 to about 50 cutting teeth 114, among other ranges of quantities and/or quantities of cutting teeth 114 that are possible and contemplated herein. In some embodiments, a set of cutting teeth 114 includes about 8 cutting teeth 114, among other quantities of cutting teeth 114 that are possible and contemplated herein.

In some embodiments, the set of cutting teeth 114 are positioned on the distal end 108 in a straight line or substantially straight line. In other embodiments, the set of cutting teeth 114 are positioned along a curve on the distal end 108 defined by a radius R1.

The radius R1 may be any suitable radius and/or curvature that can assist in and/or facilitate initiating an osteotomy (e.g., a wedge-shaped osteotomy) when oscillated. In various embodiments, the radius R1 is in the range of about 5 mm to about 80 mm, among other ranges of lengths and/or lengths that can define an amount and/or degree of curvature that are possible and contemplated herein. In some embodiments, the radius R1 is about 25 mm, among other lengths that can define an amount and/or degree of curvature that are possible and contemplated herein.

In some embodiments, the set of cutting teeth 114 on the distal end 108 may define a cutting tip 120 that can initiate an osteotomy (e.g., a wedge osteotomy). Further, the cutting blades 112 positioned along the single-plane slope 118 may define a cutting slope 118 that can perform the osteotomy to produce a wedge-shaped cut. In various embodiments, the coordination of the cutting tip 120 and the cutting slope 118 can allow the surgical instrument 100 to produce a wedge-shaped osteotomy in a single cut and/or single pass.

As further shown, the proximal end 110 includes an attachment mechanism 116 positioned thereon. The attachment mechanism 116 may include any suitable size dimensions, shape, and/or configuration that enables attachments of the surgical instrument 100 to a surgical instrument (not shown). That is, while the attachment mechanism 116 is shown as including particular relative size dimensions, shapes, and configurations, the various embodiments of the surgical instrument 100 are not limited to the illustrated attachment mechanism 116. That is, other embodiments of the surgical instrument 100 may include one or more different relative size dimension(s), shapes, and/or configurations.

FIGS. 2A through 2D are schematic diagrams illustrating various views of another embodiment of a surgical instrument 200. In various embodiments, the surgical instrument 200 can be utilized to perform a wedge-shaped osteotomy. Further, the wedge-shaped osteotomy can be achieved with a single cut or pass utilizing the surgical instrument 200.

A surgical instrument 200 may be constructed of any suitable material that can cut bone. In various embodiments, the surgical instrument 200 is constructed of a sterilized suitable material that can cut bone. In some embodiments, the surgical instrument 200 includes stainless steel, among other suitable materials that are possible and contemplated herein. In additional or alternative embodiments, the surgical instrument 200 includes surgical grade stainless steel, among other suitable surgical grade materials that are possible and contemplated herein.

At least in the illustrated embodiment, the surgical instrument 200 includes, among other features, a body 202 including at least a bottom surface 204, a top surface 206, a distal end 208, and a proximal end 210, a set of cutting blades 212 positioned on the body 202, a set of cutting teeth 214 positioned on the distal end 208, and an attachment mechanism 216 positioned on the proximal end 210. A body 202 may include any suitable dimensions that can perform an osteotomy. In various embodiments, the body 202 includes dimensions that are suitable for performing an osteotomy on a human.

In various embodiments, the body 202 includes a length L2 (see FIG. 2B) in the range of about 15 mm to about 70 mm, among other ranges of length and/or lengths that are possible and contemplated herein. In some embodiments, the body 202 includes a length L2 of about 20 mm, among other lengths that are possible and contemplated herein.

The body 202 further includes a width W3 (see FIG. 2B) at the distal end 208 and a width W4 (see FIG. 2B) at the proximal end 210. In various embodiments, the width W3 is in the range of about 5 mm to about 30 mm, among other ranges of widths and/or widths that are possible and contemplated herein. In some embodiments, the width W3 is about 7.5 mm, among other widths that are possible and contemplated herein. In additional or alternative embodiments, the width W4 is in the range of about 5 mm to about 70 mm, among other ranges of widths and/or widths that are possible and contemplated herein. In some embodiments, the width W4 is about 11 mm, among other widths that are possible and contemplated herein.

In some embodiments, the width W3 and the width W4 are the same width or substantially the same width. In other embodiments, the width W4 is greater than the width W3 such that the proximate end 210 is wider than the distal end 208 or, alternatively, the distal end 208 is narrower than the proximate end 210 (e.g., the width W3 is less than the width W4). That is, in various embodiments, the surgical instrument 200 includes a tapered shape and/or tapers from the distal end 208 to the proximate end 210.

A bottom surface 204 may include any suitable shape and/or profile that can facilitate or assist the surgical instrument 200 in performing an osteotomy (e.g., a wedge-shaped osteotomy). In various embodiments, the bottom surface 204 includes a flat or substantially flat surface, among other profiles and/or planes that are possible and contemplated herein.

A top surface 206 may include any suitable profile upon which one or more cutting blades 212 can be positioned. In various embodiments, the top surface 206 includes a slope 218 (see FIGS. 2C and 2D) that extends upward and/or away from the bottom surface 204 and the distal end 208. The slope 218 may include any suitable grade (e.g., rise over run) that can facilitate and/or assist the surgical instrument 200 in performing an osteotomy and particularly, a wedge-shaped osteotomy. That is, the top surface 206 and/or surgical instrument 200 may include any suitable grade that can facilitate and/or assist the surgical instrument 200 in performing a wedge-shaped osteotomy in one cut and/or one pass.

Figure 2A:
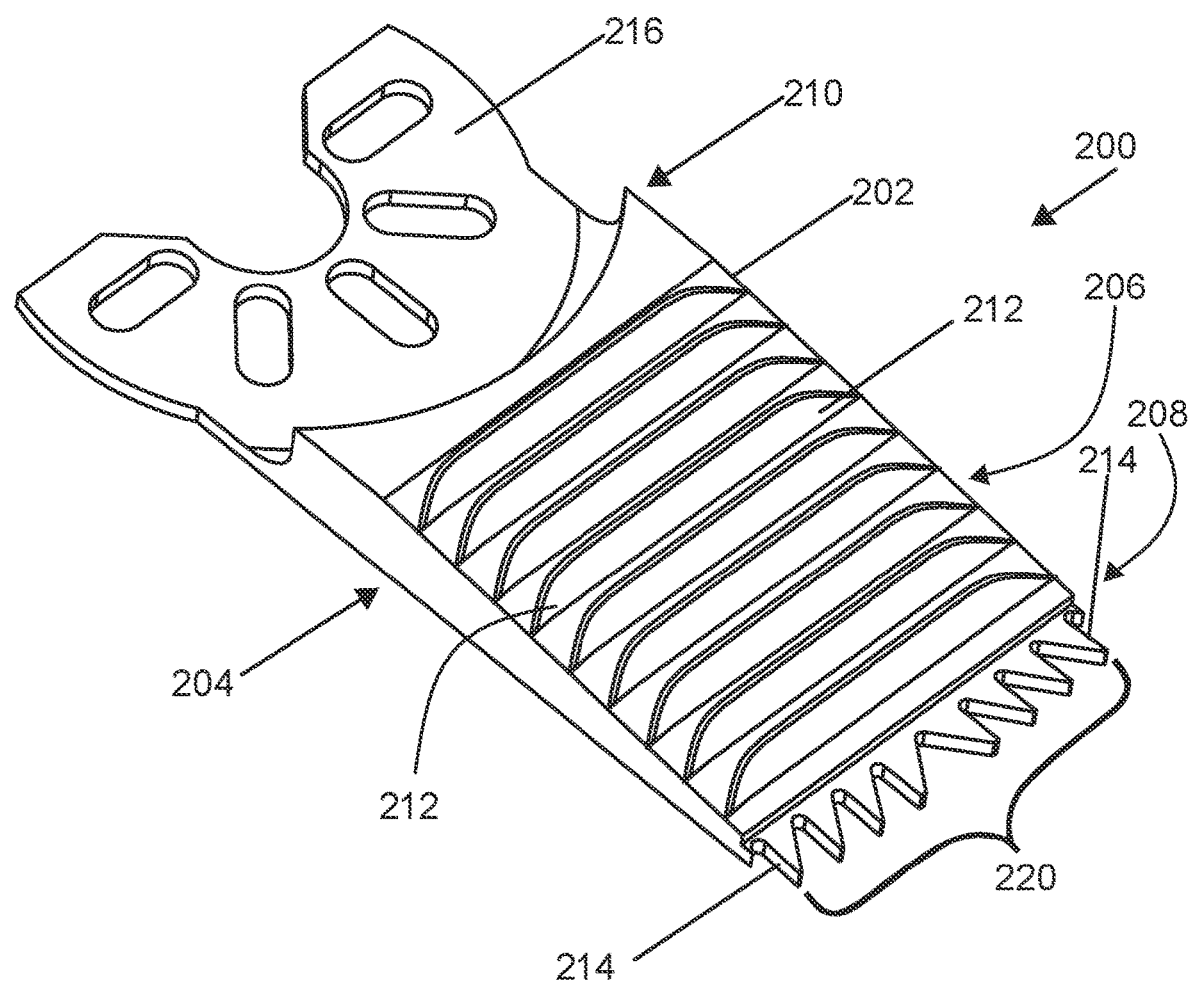
FIGS. 2A through 2D are schematic diagrams illustrating various embodiments of a surgical instrument including multiple rows of cutting blades.
Figure 2B:
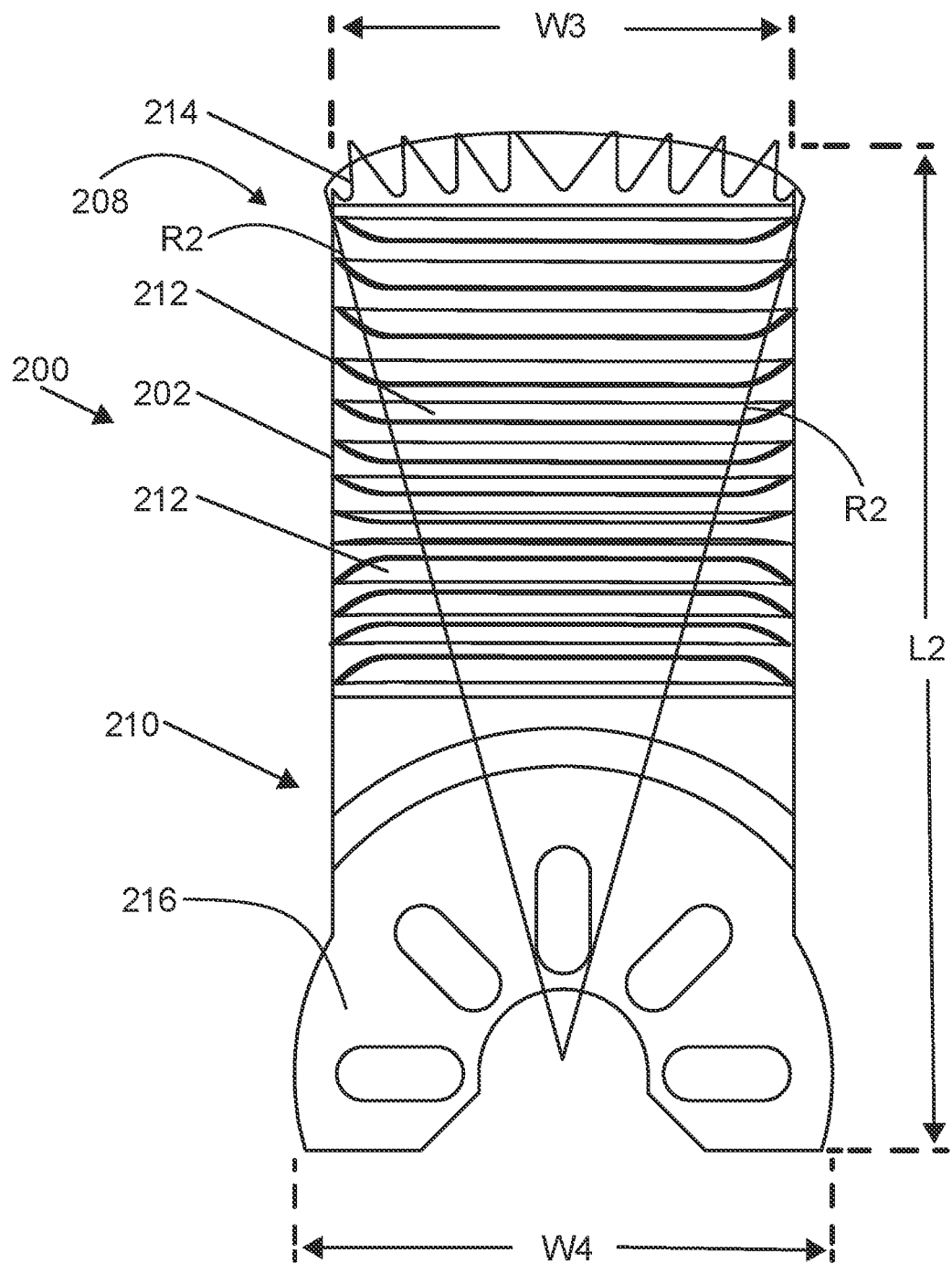
Figure 2C:
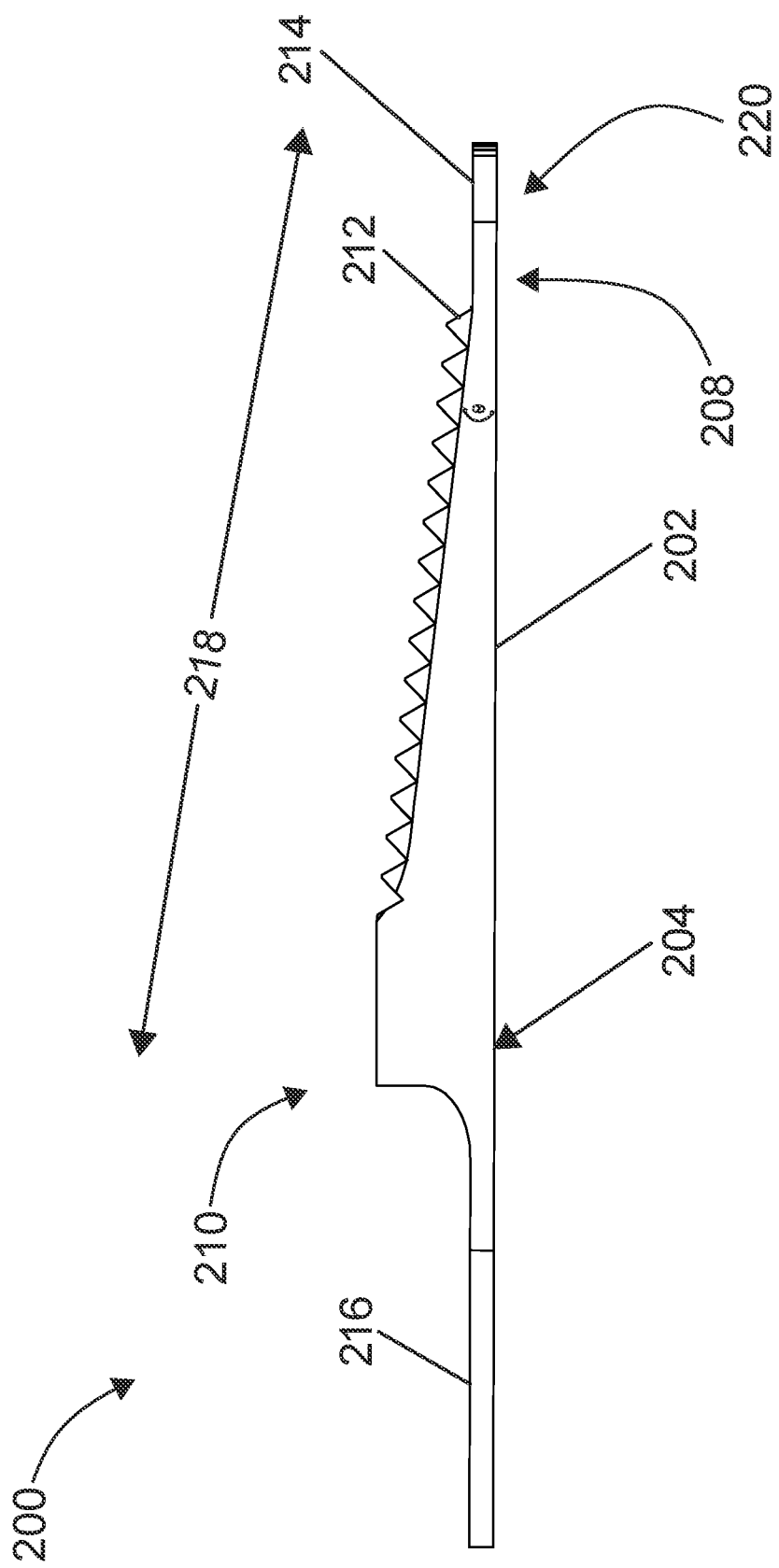
Figure 2D:
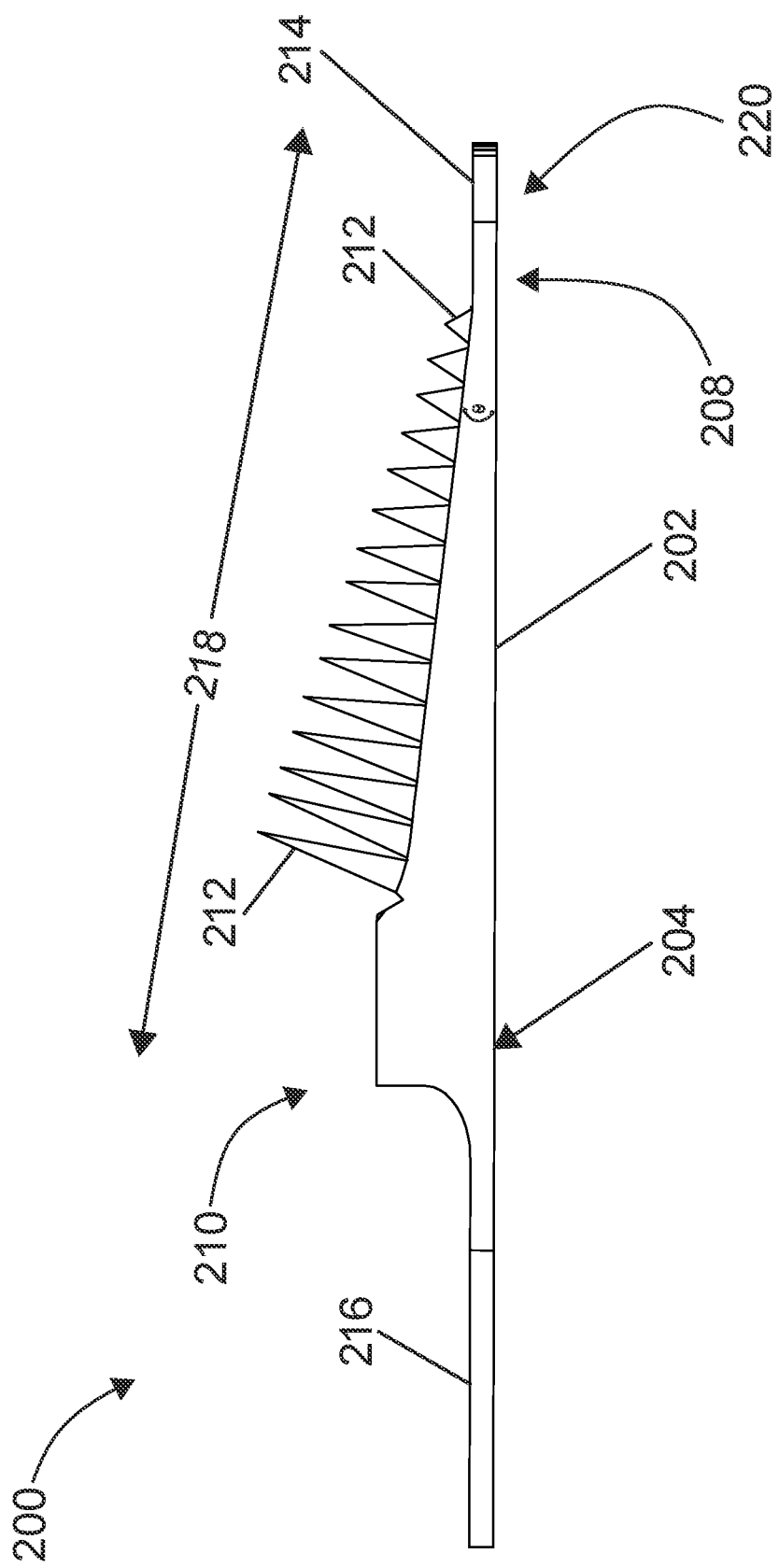

In various embodiments, the slope 218 includes a grade in the range of about 0° (or flat) to about 15°, among other ranges of grades, grades, and/or slopes that are possible and contemplated herein. In other words, an angle θ in the range of about 0° to about 15° (e.g., the angle θ=0°, 1°, 2°, 3°, 4°, 5°, 6°, 7°, 8°, 9°, 10°, 11°, 12°, 13°, 14°, or 15° and/or the angle θ≈0°, 1°, 2°, 3°, 4°, 5°, 6°, 7°, 8°, 9°, 10°, 11°, 12°, 13°, 14°, or 15°) is defined between the top surface 206 and the bottom surface 204 beginning at the distal end 208 and extending upward and toward the proximate end 210, as shown in FIGS. 2C and 2D. In some embodiments, the slope 218 includes a grade of about 7° degrees (e.g., the angle θ=7° or the angle θ≈7°), among other suitable grades and/or slopes that are possible and contemplated herein.

In several embodiments, the top surface 206 includes a set of cutting blades 212 positioned thereon. As illustrated, the set of cutting blades 212 are spaced apart and positioned horizontally to form a set of rows of cutting blades 212.

A set of cutting blades 212 may include any suitable quantity of cutting blades 212 and/or quantity of rows of cutting blades 212 that can facilitate and/or assist the surgical instrument 200 in performing an osteotomy and particularly, a wedge-shaped osteotomy. In various embodiments, the top surface 206 includes a suitable quantity of cutting blades 212 or rows of cutting blades 212 so that the surgical instrument 200 can perform a wedge-shaped osteotomy in one cut and/or one pass.

In various embodiments, the top surface 206 includes a quantity of cutting blades 212 in the range of about two (2) cutting blades 212 to about 40 cutting blades 212, among other ranges of quantities of cutting blades 212 and/or quantities of cutting blades 212 that are possible and contemplated herein. In some embodiments, the top surface 206 includes 12 cutting blades 212, among other quantities of cutting blades 212 that are possible and contemplated herein.

While the surgical instrument 200 is shown with a top surface 206 including 9 cutting blades 212, the various embodiments of the surgical instrument 200 are not limited to 9 cutting blades 212. That is, various other embodiments of a surgical instrument 200 can include a different quantity of cutting blades 212 such that the top surface 206 can include a greater quantity of cutting blades 212 than 9 cutting blades 212 or a smaller quantity of cutting blades 212 than 9 cutting blades 212.

In some embodiments, the cutting blades 212 may be included on the entirety or substantially the entirety of the top surface 206. In other embodiments, the cutting blades 212 may be included on a portion or at least a portion of the top surface 206. That is, the quantity of rows of cutting blades 212 may extend partially or fully along the slope 208 on the top surface 106.

The portion of the top surface 206 including the cutting blades 212 may include any suitable sized portion that can produce a wedge-shaped osteotomy. Various embodiments of the surgical instrument 200 may include varying sized portions of the top surface 206 including the cutting blades 212 so that different sized and/or shaped wedge-shaped osteotomies can be obtained.

A cutting blade 212 may include any suitable shape that can facilitate and/or assist the surgical instrument 200 in performing an osteotomy (e.g., a wedge-shaped osteotomy). In various embodiments, a cutting blade 212 can include a curved blade, a straight blade, waved blade, or a wavy blade, among other suitable shapes that can facilitate cutting bone that are possible and contemplated herein. In additional or alternative embodiments, a cutting blade 212 can include a straight cutting edge and/or a serrated cutting edge, among other cutting edges that are possible and contemplated herein.

In some embodiments, all of the cutting blades 212 in the set of cutting blades 212 on the top surface 206 include the same or substantially the same shape. In alternative embodiments, at least two cutting blades 212 in the set of cutting blades 212 on the top surface 206 include different shapes or substantially different shapes. In one non-limiting example, at least one cutting blade 212 includes a straight blade and at least one cutting blade 212 includes a non-straight blade, among other shapes and/or combinations of shapes that are possible and contemplated herein. In an additional or alternative non-limiting example, the curved blade(s) and/or the straight blade(s) include a serrated edge.

In additional or alternative embodiments, a set of cutting blades 212 can include at least two subsets of cutting blades 212 in which a first subset includes two or more cutting blades 212 including a first shape and at least a second subset that includes two or more cutting blades 212 including a second, different shape. In some embodiments, one or more of the cutting blades 212 in one or more of the subsets of cutting blades 212 include a serrated edge.

In further additional or alternative embodiments, the first subset of cutting blades 212 and the second subset of cutting blades 212 include the same quantity of cutting blades 212. In other embodiments, the first subset of cutting blades 212 and the second subset of cutting blades 212 include different quantities of cutting blades 212.

In yet further additional or alternative embodiments, the cutting blades 212 in the first subset of cutting blades 212 and the cutting blades 212 in the second subset of cutting blades 212 can be positioned in a pattern. The pattern may include any suitable pattern that can assist in and/or facilitate performing an osteotomy (e.g., a wedge-shaped osteotomy). In some embodiments, the pattern may include cutting blades 212 with different shapes in an alternating pattern to provide alternating rows of cutting blades 212.

A cutting blade 212 may include any suitable height that can facilitate and/or assist the surgical instrument 200 in performing an osteotomy (e.g., a wedge-shaped osteotomy). In various embodiments, the cutting blades 212 can include a height in the range of about 0.1 mm to about 30 mm, among other suitable heights that can facilitate cutting bone that are possible and contemplated herein. In some embodiments, the cutting blades 212 include a height of 0.75 mm.

In some embodiments, all of the rows of cutting blades 212 on the top surface 206 include a uniform height (see FIG. 2C). In alternative embodiments, the rows of cutting blades 212 on the top surface 206 include a gradually increasing height (see FIG. 2D). In some embodiments, the height of the rows of cutting blades 212 gradually increases from the distal end 208 to the proximal end 210.

As shown, the distal end 208 includes a set of cutting teeth 214 (e.g., a single tooth 214 or multiple teeth 214) positioned thereon. A set of cutting teeth 214 may include any suitable quantity of teeth 214 that can assist in and/or facilitate initiating an osteotomy and particularly, a wedge-shaped osteotomy, when oscillated.

In various embodiments, the set of cutting teeth 214 includes a quantity of cutting teeth 214 in the range of one cutting tooth 214 to about 50 cutting teeth 214, among other ranges of quantities and/or quantities of cutting teeth 214 that are possible and contemplated herein. In some embodiments, a set of cutting teeth 214 includes about 8 cutting teeth 214, among other quantities of cutting teeth 214 that are possible and contemplated herein.

In some embodiments, the set of cutting teeth 214 are positioned on the distal end 208 in a straight line or substantially straight line. In other embodiments, the set of cutting teeth 214 are positioned along a curve on the distal end 208 defined by a radius R2.

The radius R2 may be any suitable radius and/or curvature that can assist in and/or facilitate initiating an osteotomy (e.g., a wedge-shaped osteotomy) when oscillated. In various embodiments, the radius R2 is in the range of about 5 mm to about 80 mm, among other ranges of lengths and/or lengths that can define an amount and/or degree of curvature that are possible and contemplated herein. In some embodiments, the radius R2 is about 25 mm, among other lengths that can define an amount and/or degree of curvature that are possible and contemplated herein.

In some embodiments, the set of cutting teeth 214 on the distal end may define a cutting tip 220 that can initiate an osteotomy (e.g., a wedge osteotomy). Further, the cutting blades 212 positioned along the single-plane slope 218 may define a cutting slope 218 that can perform the osteotomy to produce a wedge-shaped cut. In various embodiments, the coordination of the cutting tip 220 and the cutting slope 218 can allow the surgical instrument 200 to produce a wedge-shaped osteotomy in a single cut and/or single pass.

As further shown, the proximal end 210 includes an attachment mechanism 216 positioned thereon. The attachment mechanism 216 may include any suitable size dimensions, shape, and/or configuration that enables attachments of the surgical instrument 200 to a surgical instrument (not shown). That is, while the attachment mechanism 216 is shown as including particular relative size dimensions, shapes, and configurations, the various embodiments of the surgical instrument 200 are not limited to the illustrated attachment mechanism 216. That is, other embodiments of the surgical instrument 200 may include one or more different relative size dimension(s), shapes, and/or configurations.

With reference to FIGS. 3A through 3E, FIGS. 3A through 3E are schematic diagrams illustrating various views of one embodiment of a surgical instrument 300. In various embodiments, the surgical instrument 300 can be utilized to perform a wedge-shaped osteotomy. Further, the wedge-shaped osteotomy can be achieved with a single cut or pass utilizing the surgical instrument 300.

A surgical instrument 300 may be constructed of any suitable material that can cut bone. In various embodiments, the surgical instrument 300 is constructed of a sterilized suitable material that can cut bone. In some embodiments, the surgical instrument 300 includes stainless steel, among other suitable materials that are possible and contemplated herein. In additional or alternative embodiments, the surgical instrument 300 includes surgical grade stainless steel, among other suitable surgical grade materials that are possible and contemplated herein.

At least in the illustrated embodiment, the surgical instrument 300 includes, among other features, a body 302 including at least a bottom surface 304, a top surface 306, a distal end 308, and a proximal end 310, a set of cutting blades 312 positioned on the body 302, a set of cutting teeth 314 positioned on the distal end 308, and an attachment mechanism 316 positioned on the proximal end 310. A body 302 may include any suitable dimensions that can perform an osteotomy. In various embodiments, the body 302 includes dimensions that are suitable for performing an osteotomy on a human.

In various embodiments, the body 302 includes a length L3 (see FIG. 3B) in the range of about 15 mm to about 70 mm, among other ranges of length and/or lengths that are possible and contemplated herein. In some embodiments, the body 302 includes a length L3 of about 20 mm, among other lengths that are possible and contemplated herein.

The body 302 further includes a width W5 (see FIG. 3B) at the distal end 308 and a width W6 (see FIG. 3B) at the proximal end 310. In various embodiments, the width W5 is in the range of about 5 mm to about 30 mm, among other ranges of widths and/or widths that are possible and contemplated herein. In some embodiments, the width W5 is about 7.5 mm, among other widths that are possible and contemplated herein. In additional or alternative embodiments, the width W6 is in the range of about 5 mm to about 70 mm, among other ranges of widths and/or widths that are possible and contemplated herein. In some embodiments, the width W6 is about 11 mm, among other widths that are possible and contemplated herein.

In some embodiments, the width W5 and the width W6 are the same width or substantially the same width. In other embodiments, the width W6 is greater than the width W5 such that the proximate end 310 is wider than the distal end 308 or, alternatively, the distal end 308 is narrower than the proximate end 310 (e.g., the width W5 is less than the width W6). That is, in various embodiments, the surgical instrument 300 includes a tapered shape and/or tapers from the distal end 308 to the proximate end 310.

A bottom surface 304 may include any suitable shape and/or profile that can facilitate or assist the surgical instrument 300 in performing an osteotomy (e.g., a wedge-shaped osteotomy). In various embodiments, the bottom surface 304 includes a flat or substantially flat surface, among other profiles and/or planes that are possible and contemplated herein.

A top surface 306 may include any suitable profile upon which one or more cutting blades 312 can be positioned. In various embodiments, the top surface 306 includes a slope 318 (see FIG. 3D) that extends upward and/or away from the bottom surface 304 and the distal end 308. The slope 318 may include any suitable grade (e.g., rise over run) that can facilitate and/or assist the surgical instrument 300 in performing an osteotomy and particularly, a wedge-shaped osteotomy. That is, the top surface 306 and/or surgical instrument 300 may include any suitable grade that can facilitate and/or assist the surgical instrument 300 in performing a wedge-shaped osteotomy in one cut and/or one pass.

In various embodiments, the slope 318 includes a grade in the range of about zero degrees (0° or flat, see FIG. 3E) to about fifteen degrees (15°, see FIG. 3D), among other ranges of grades, grades, and/or slopes that are possible and contemplated herein. In other words, an angle θ in the range of about 0° to about 15° (e.g., the angle θ=0°, 1°, 2°, 3°, 4°, 5°, 6°, 7°, 8°, 9°, 10°, 11°, 12°, 13°, 14°, or 15° and/or the angle θ≈0°, 1°, 2°, 3°, 4°, 5°, 6°, 7°, 8°, 9°, 10°, 11°, 12°, 13°, 14°, or 15°) is defined between the top surface 306 and the bottom surface 304 beginning at the distal end 308 and extending upward and toward the proximate end 310, as shown in FIGS. 3D and 3E. In some embodiments, the slope 318 includes a grade of about seven (7°) degrees (e.g., the angle θ=7° or the angle θ≈7°), among other suitable grades and/or slopes that are possible and contemplated herein.

In several embodiments, the top surface 306 includes a set of cutting blades 312 positioned thereon. As illustrated, the set of cutting blades 312 are spaced apart and positioned vertically to form a set of columns of cutting blades 312. As shown, one or more cutting blades 312 are positioned on the top surface 306 so that one end of the cutting blade 312 or cutting blades 312 begin(s) at or substantially at the distal end 308 and extend toward the proximal end 310.

In various embodiments, all of the cutting blades 312 in the set of cutting blades 312 begin at or substantially at the distal end 308 or a portion of the cutting blades 312 in the set of cutting blades 312 begin(s) at or substantially at the distal end 308. The cutting blades 312 may include any suitable shape and/or dimensions at the distal end 308 can assist in and/or facilitate initiating an osteotomy and particularly, a wedge-shaped osteotomy, when oscillated.

A set of cutting blades 312 may include any suitable quantity of cutting blades 312 and/or quantity of columns of cutting blades 312 that can facilitate and/or assist the surgical instrument 300 in performing an osteotomy and particularly, a wedge-shaped osteotomy.

The top surface 306 may include any suitable quantity of cutting blades 312 so that the surgical instrument 300 can perform a wedge-shaped osteotomy in one cut and/or one pass. In various embodiments, the top surface 306 includes a quantity of cutting blades 312 in the range of about 2 cutting blades 312 to about 40 cutting blades 312, among other ranges of quantities of cutting blades 312 and/or quantities of cutting blades 312 that are possible and contemplated herein. In some embodiments, the top surface 306 includes 12 cutting blades 312, among other quantities of cutting blades 312 that are possible and contemplated herein.

While the surgical instrument 300 is shown with a top surface 306 including 14 cutting blades 312, the various embodiments of the surgical instrument 300 are not limited to 14 cutting blades 312. That is, various other embodiments of a surgical instrument 300 can include a different quantity of cutting blades 312 such that the top surface 306 can include a greater quantity of cutting blades 312 than 14 cutting blades 312 or a smaller quantity of cutting blades 312 than 14 cutting blades 312.

Figure 3A:
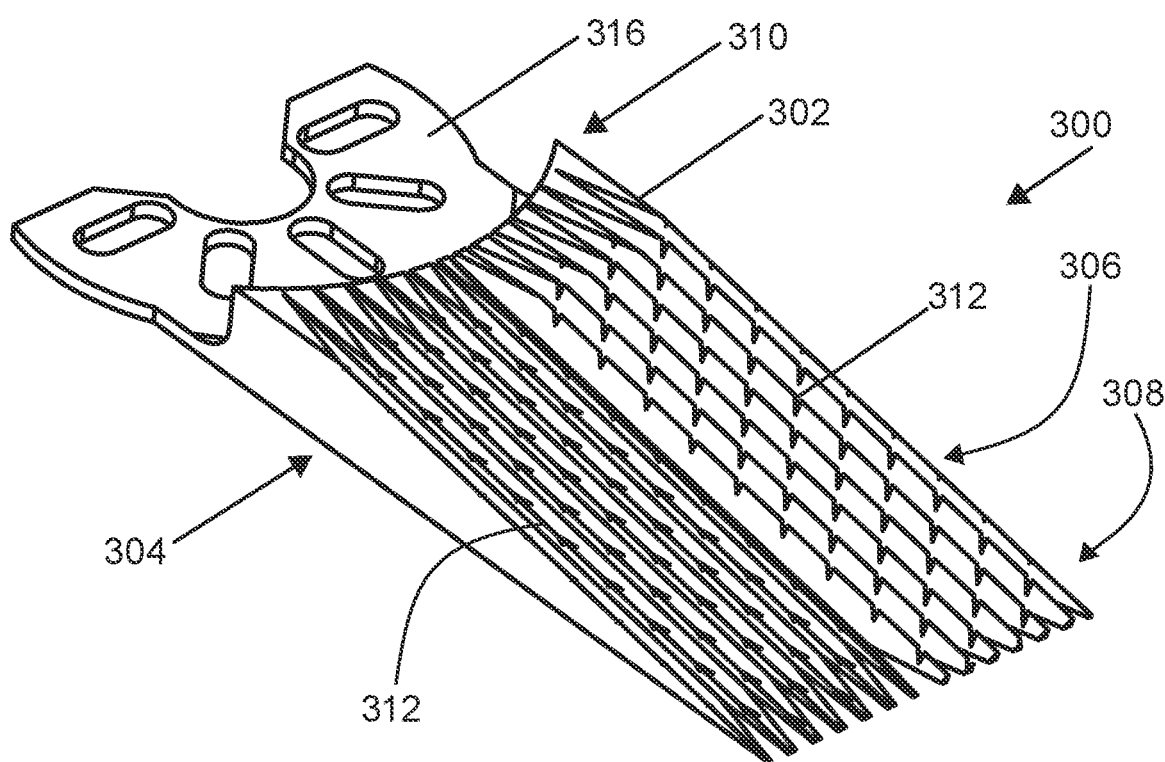
FIGS. 3A through 3E are schematic diagrams illustrating various another embodiments of a surgical instrument including multiple columns of cutting blades.
Figure 3B:
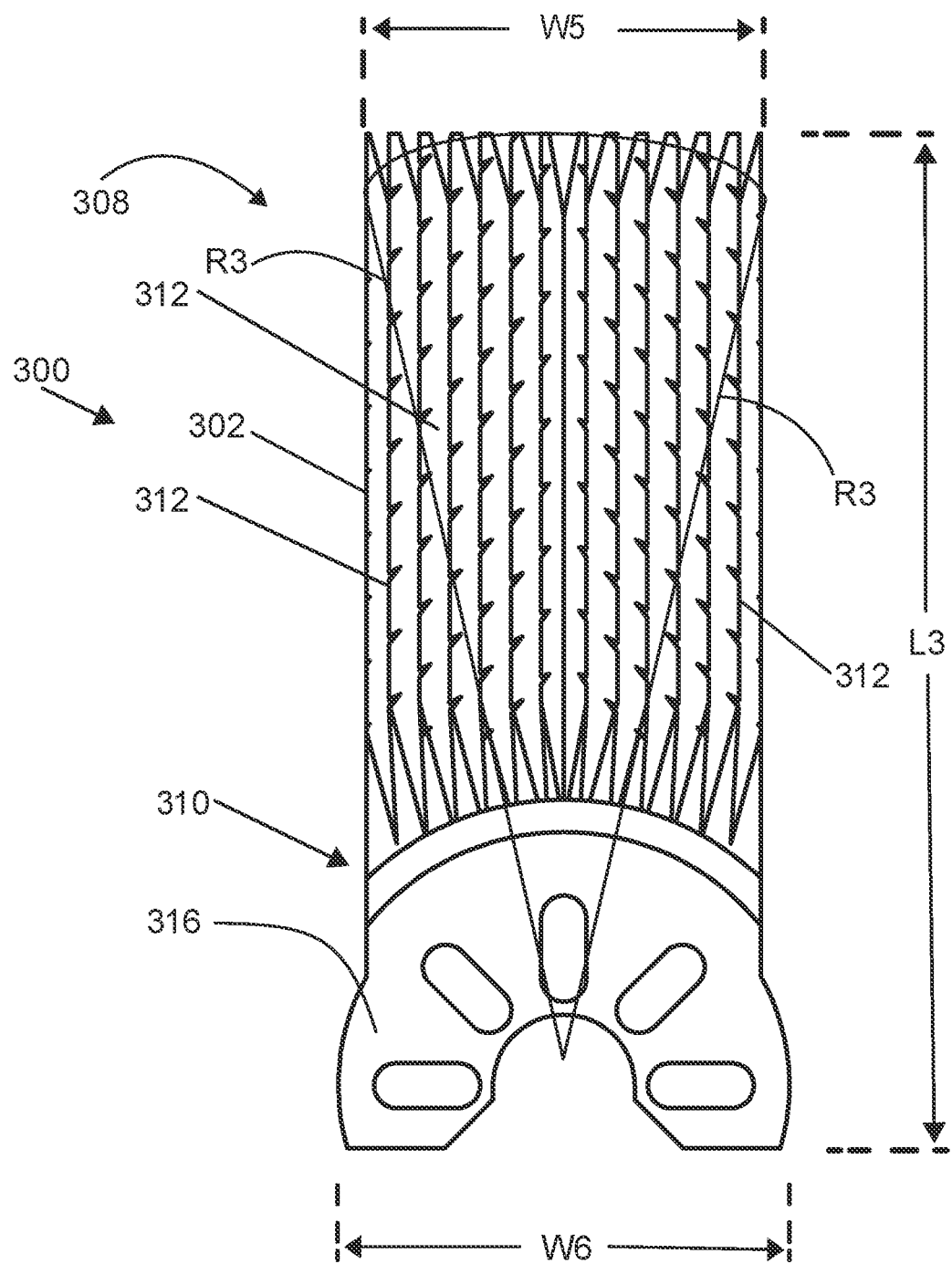
Figure 3C:
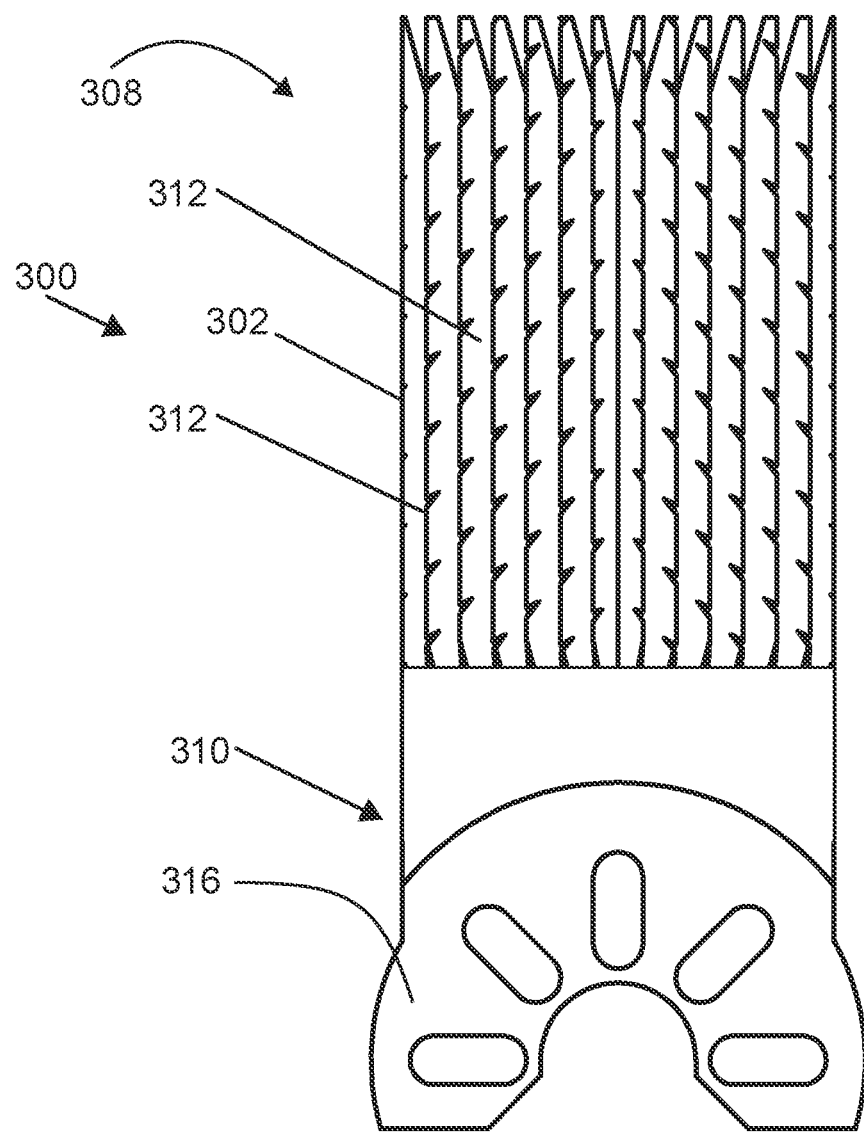
Figure 3D:
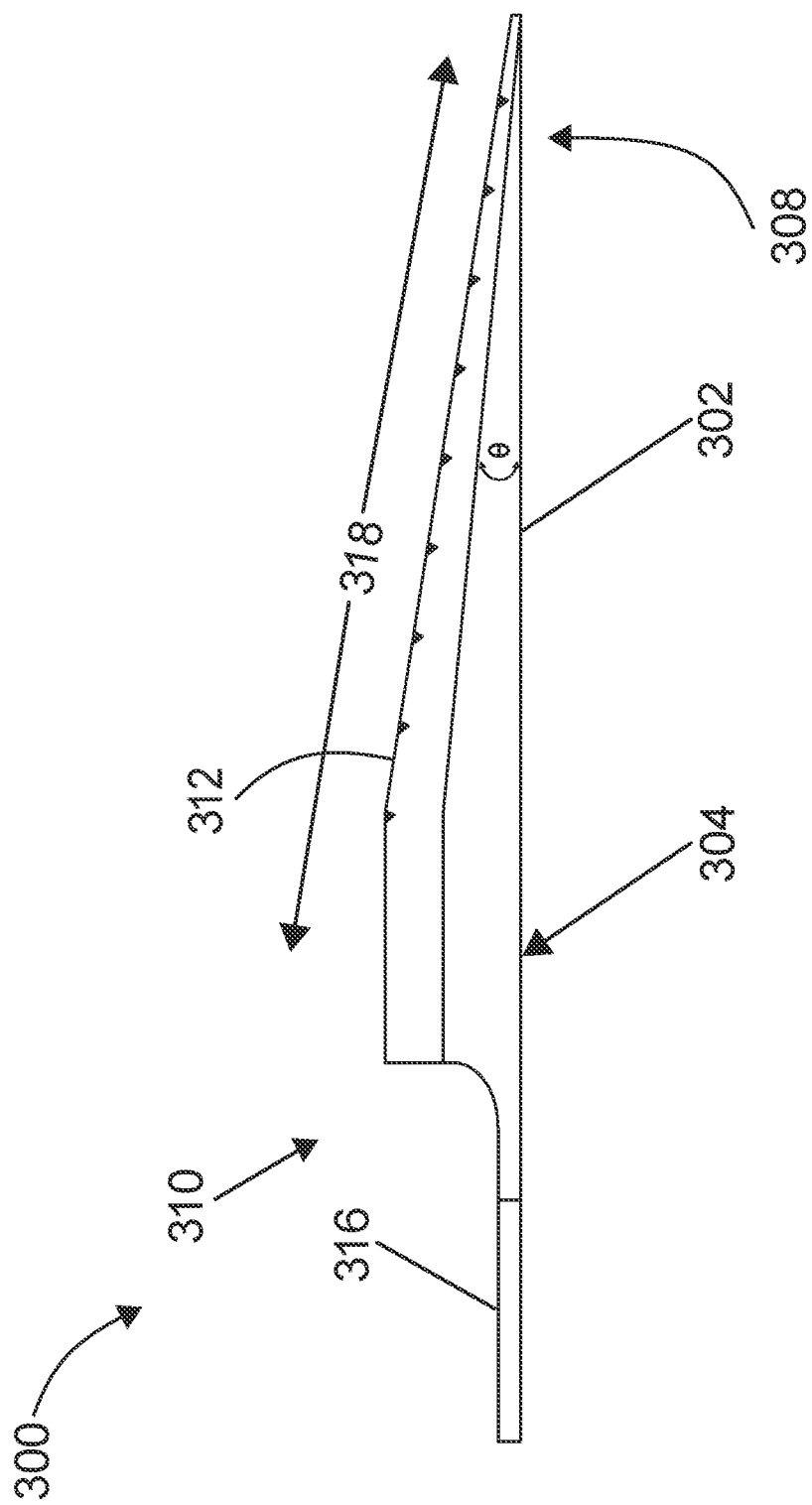
Figure 3E:
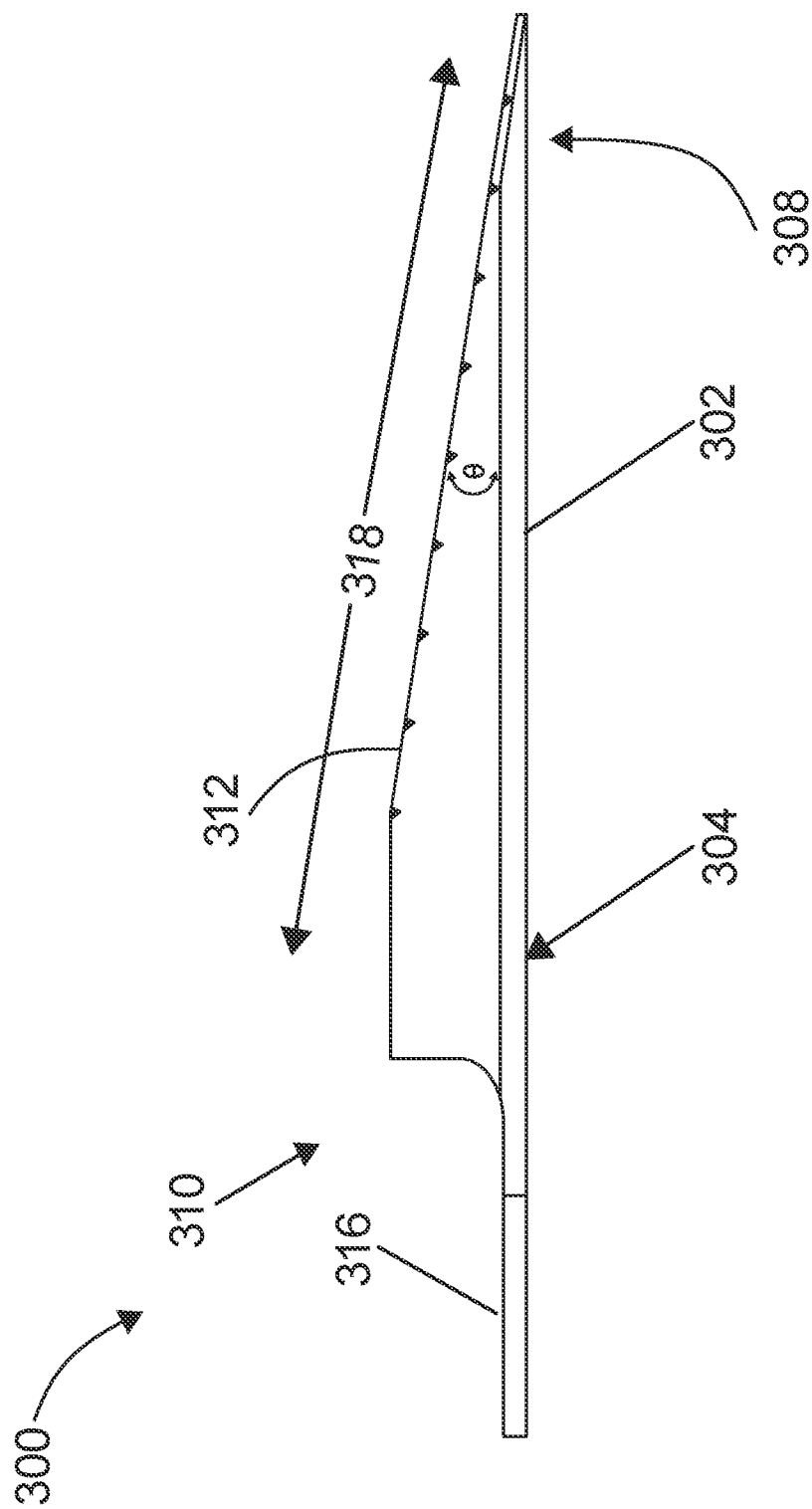

In some embodiments, the cutting blades 312 may extend over and/or along the entirety or substantially the entirety of the top surface 306 (see FIG. 3B). In other embodiments, the cutting blades 312 extend over and/or along a portion or at least a portion of the top surface 306 (see FIG. 3C). That is, the cutting blades 312 may extend partially or fully from the distal end 308 to the proximal end 310.

The portion of the top surface 306 including the cutting blades 312 may include any suitable sized portion that can produce a wedge-shaped osteotomy. Various embodiments of the surgical instrument 300 may include varying sized portions of the top surface 306 including the cutting blades 312 so that different sized and/or wedge-shaped osteotomies can be obtained. That is, different embodiments may include cutting blades 312 with differing lengths to produce different sized and/or wedge-shaped osteotomies.

A cutting blade 312 may include any suitable shape that can facilitate and/or assist the surgical instrument 300 in performing an osteotomy (e.g., a wedge-shaped osteotomy). In various embodiments, a cutting blade 312 can include a curved blade (e.g., a vertically curved blade), a straight blade, waved blade (e.g., a horizontally curved blade), or a wavy blade (e.g., a blade with multiple horizontal curves), among other suitable shapes that can facilitate cutting bone that are possible and contemplated herein. In additional or alternative embodiments, a cutting blade 312 can include a straight cutting edge and/or a serrated cutting edge, among other cutting edges that are possible and contemplated herein.

In some embodiments, all of the cutting blades 312 in the set of cutting blades 312 on the top surface 306 include the same or substantially the same shape. In alternative embodiments, at least two cutting blades 312 in the set of cutting blades 312 on the top surface 306 include different shapes or substantially different shapes. In one non-limiting example, at least one cutting blade 312 includes a straight blade and at least one cutting blade 312 includes a curved blade (or other non-straight blade), among other shapes and/or combinations of shapes that are possible and contemplated herein. In an additional or alternative non-limiting example, the straight blade(s) and/or the curved blade(s) include a serrated cutting edge.

In additional or alternative embodiments, a set of cutting blades 312 can include at least two subsets of cutting blades 312 in which a first subset includes two or more cutting blades 312 including a first shape and at least a second subset that includes two or more cutting blades 312 including a second, different shape. In some embodiments, one or more of the cutting blades 312 in one or more of the subsets of cutting blades 312 includes a serrated edge.

In further additional or alternative embodiments, the first subset of cutting blades 312 and the second subset of cutting blades 312 include the same quantity of cutting blades 312. In other embodiments, the first subset of cutting blades 312 and the second subset of cutting blades 312 include different quantities of cutting blades 312.

In yet further additional or alternative embodiments, the cutting blades 312 in the first subset of cutting blades 312 and the cutting blades 312 in the second subset of cutting blades 312 can be positioned in a pattern. The pattern may include any suitable pattern that can assist in and/or facilitate performing an osteotomy (e.g., a wedge-shaped osteotomy). In some embodiments, the pattern may include cutting blades 312 with different shapes in an alternating pattern to provide alternating columns of cutting blades 312.

A cutting blade 312 may include any suitable height that can facilitate and/or assist the surgical instrument 300 in performing an osteotomy (e.g., a wedge-shaped osteotomy). In various embodiments, the cutting blades 312 can include a height in the range of about 0.1 mm to about 30 mm, among other suitable heights that can facilitate cutting bone that are possible and contemplated herein. In some embodiments, the cutting blades 312 include a height of about 0.75 mm, among other suitable heights that can facilitate cutting bone that are possible and contemplated herein.

In some embodiments, all of the cutting blades 312 in the set of cutting blades 312 on the top surface 306 include a respective uniform height (see FIG. 3D). In various embodiments, all of the cutting blades 312 in the set of cutting blades 312 include the same respective uniform height or at least two cutting blades 312 in the set of cutting blades 312 include different respective uniform heights.

As shown in FIG. 3D, various embodiments include the body 302 with angle θ created between the bottom surface 304 and the top surface 306 such that the top surface 306 defines the slope 318 from the distal end 308 to the proximal end 310. Further illustrated in FIG. 3D, the set of cutting blades 312 includes a uniform height such that when positioned on the top surface 306, the cutting surface (or top surface) of each cutting blade 312 mirrors and/or includes the same slope 318 as that of the top surface 306. In other words, the cutting surface of each cutting blade 312 extends vertically and rises upward along the slope 318 from the distal end 308 to the proximal end 310 (see FIG. 3B) or toward the proximal end 310 on a portion of the top surface 306 (see FIG. 3C).

In alternative embodiments, all of the cutting blades 312 on the top surface 306 include a respective height that increases from the distal end 308 to the proximal end 310 (see FIG. 3E). As shown in FIG. 3E, various embodiments include the body with a flat (0° slope) top surface 306 and one or more cutting blades 312 with angle θ between the cutting surface and a surface of the cutting blade 312 positioned on the body 302 such that the height of each cutting blade 312 increases along the slope 318 from the distal end 308 to the proximal end 310.

In various embodiments, the angle θ of each cutting blade 312 is in the range of about 1° to about 15°, among other ranges of angles and/or angles that are possible and contemplated herein. In other words, an angle θ in the range of about 1° to about 15° (e.g., the angle θ=1°, 2°, 3°, 4°, 5°, 6°, 7°, 8°, 9°, 10°, 11°, 12°, 13°, 14°, or 15° and/or the angle θ≈1°, 2°, 3°, 4°, 5°, 6°, 7°, 8°, 9°, 10°, 11°, 12°, 13°, 14°, or 15°) is defined between the cutting surface of each cutting blade 312 and the surface of the cutting blade positioned on the body 302, as shown in FIG. 3E. In other words, the cutting surface of each cutting blade 312 extends vertically and rises upward along the slope 318 from the distal end 308 to the proximal end 310 (see FIG. 3B) or toward the proximal end 310 on a portion of the top surface 306 (see FIG. 3C).

In some embodiments, all of the cutting blades 312 in the set of cutting blades 312 include the same respective increasing height or angle θ such that the cutting blades 312 increase in height starting at or proximate to the distal end 308 and extend to or toward the proximal end 310 at the same rate. In alternative embodiments, at least two cutting blades 312 in the set of cutting blades 312 include different respective increasing heights or angles θ such that at least two cutting blades 312 increase in height starting at or proximate to the distal end 308 and extend to or toward the proximal end 310 at different rates.

In some embodiments, the set of cutting blades 312 are positioned on the distal end 308 in a straight line or substantially straight line. In other embodiments, the set of cutting blades 312 are positioned along a curve on the distal end 308 defined by a radius R3.

The radius R3 may be any suitable radius and/or curvature that can assist in and/or facilitate initiating an osteotomy (e.g., a wedge-shaped osteotomy) when oscillated. In various embodiments, the radius R3 is in the range of about 5 mm to about 80 mm, among other ranges of lengths and/or lengths that can define an amount and/or degree of curvature that are possible and contemplated herein. In some embodiments, the radius R3 is about 25 mm, among other lengths that can define an amount and/or degree of curvature that are possible and contemplated herein.

In some embodiments, the cutting blades 312 include a cutting surface along the slope 318 that can define single-plane. The single-plane may define a cutting slope 318 that can perform a wedge-shaped osteotomy in a single cut and/or single pass.

As further shown in FIGS. 3A through 3E, the proximal end 310 includes an attachment mechanism 316 positioned thereon. The attachment mechanism 316 may include any suitable size dimensions, shape, and/or configuration that enables attachments of the surgical instrument 300 to a surgical instrument (not shown). That is, while the attachment mechanism 316 is shown as including particular relative size dimensions, shapes, and configurations, the various embodiments of the surgical instrument 300 are not limited to the illustrated attachment mechanism 316. That is, other embodiments of the surgical instrument 300 may include one or more different relative size dimension(s), shapes, and/or configurations.

FIGS. 4A through 4F are schematic diagrams illustrating various views of various embodiments of a surgical instrument 400. In various embodiments, the surgical instrument 400 can be utilized to perform a wedge-shaped osteotomy, a straight-cut osteotomy, and/or a parallel-cut osteotomy. Further, the wedge-shaped osteotomy, straight-cut osteotomy, and/or parallel-cut osteotomy can be achieved with a single cut or pass utilizing the surgical instrument 400.

A surgical instrument 400 may be constructed of any suitable material that can cut bone. In various embodiments, the surgical instrument 400 is constructed of a sterilized suitable material that can cut bone. In some embodiments, the surgical instrument 400 includes stainless steel, among other suitable materials that are possible and contemplated herein. In additional or alternative embodiments, the surgical instrument 400 includes surgical grade stainless steel, among other suitable surgical grade materials that are possible and contemplated herein.

At least in the embodiments illustrated in FIGS. 4A, 4B, 4C, 4D, 4E, and 4F, the surgical instrument 400 includes, among other features, a body 402 including at least a first surface 404, a second surface 406 (e.g., opposite the first surface 404), a distal end 408, and a proximal end 410. The body 402 may include any suitable dimensions that can perform an osteotomy. In various embodiments, the body 402 includes dimensions that are suitable for performing an osteotomy on a human. A surgical instrument 400 can further include, among other features and/or elements, a set of cutting blades 412A positioned on the first surface 404, a set of cutting blades 412B positioned on the second surface 406, a set of cutting teeth 414 positioned on the distal end 408, and an attachment mechanism 416 positioned on the proximal end 410.

In various embodiments, the first surface 404 includes a set of cutting blades 412A positioned thereon. As illustrated, the set of cutting blades 412A are spaced apart and positioned vertically and/or angles with respect to the first surface 404 to form a set of columns 422A of cutting blades 412A.

In further embodiments, the second surface 406 includes a set of cutting blades 412B positioned thereon. As illustrated, the set of cutting blades 412B are spaced apart and positioned vertically and/or angles with respect to the second surface 406 to form a set of columns 422B of cutting blades 412B.

A cutting blade 412A and 412B (also referred to herein individually and/or collectively, as cutting blade(s) 412) may include any suitable shape that can facilitate and/or assist the surgical instrument 400 in performing an osteotomy (e.g., a wedge-shaped osteotomy, a straight-cut osteotomy, and/or a parallel-cut osteotomy). In various embodiments, a cutting blade 412 can include a curved blade (e.g., a vertically curved blade), a straight blade, a single edge blade, a smooth edge blade, waved blade (e.g., a horizontally curved blade), or a wavy blade (e.g., a blade with multiple horizontal curves), among other suitable shapes that can facilitate cutting bone that are possible and contemplated herein. In additional or alternative embodiments, a cutting blade 412 can include a straight cutting edge and/or a serrated cutting edge, among other cutting edges that are possible and contemplated herein.

In some embodiments, all of the cutting blades 412A in the set of cutting blades 412A on the first surface 404 include the same or substantially the same shape. In alternative embodiments, at least two cutting blades 412A in the set of cutting blades 412A on the first surface 404 include different shapes or substantially different shapes.

In additional embodiments, all of the cutting blades 412B in the set of cutting blades 412B on the second surface 406 include the same or substantially the same shape. In alternative embodiments, at least two cutting blades 412B in the set of cutting blades 412B on the second surface 406 include different shapes or substantially different shapes.

In further embodiments, all of the cutting blades 412 on the first surface 404 and the second surface 406 include the same or substantially the same shape. In alternative embodiments, at least one cutting blade 412A on the first surface 404 includes a different shape or substantially different shape than at least one cutting blade 412B on the second surface 406.

A cutting blade 412 may include any suitable height that can facilitate and/or assist the surgical instrument 400 in performing an osteotomy. In various embodiments, a cutting blade 412 can include a height in the range of about 0.1 mm to about 30 mm, among other suitable heights that can facilitate cutting bone that are possible and contemplated herein. In some embodiments, a cutting blade 412 include a height of 0.75 mm.

In some embodiments, all of the cutting blades 412A on the first surface 404 include a uniform height (see, e.g., FIG. 4E). In alternative embodiments, one or more of the cutting blades 412A on the first surface 404 include a height that gradually increases from the distal end 408 to the proximal end 410 (see, e.g., FIG. 4F).

In additional embodiments, all of the cutting blades 412B on the second surface 406 include a uniform height (see, e.g., FIG. 4E). In alternative embodiments, one or more of the cutting blades 412B on the second surface 406 include a height that gradually increases from the distal end 408 to the proximal end 410 (see, e.g., FIG. 4F).

In further embodiments, all of the cutting blades 412 on the first surface 404 and the second surface 406 include a uniform height, which can be the same and/or different uniform heights from one another. In other embodiments, all of the cutting blades 412 on the first surface 404 and the second surface 406 include gradually increasing heights, which can be the same and/or different gradually increasing heights from one another. In still further embodiments, one or more of the cutting blades 412A on the first surface 404 can include uniform heights and/or gradually increasing heights and one or more of the cutting blades 412B on the second surface 406 can include uniform heights and/or gradually increasing heights, and the various possible combinations thereof, which also includes the various combinations of the same and/or different gradually increasing heights on the first surface 404 and/or the second surface 406.

A set of cutting blades 412 may include any suitable quantity of cutting blades 412 and/or quantity of columns 422A and 422B (also referred to herein individually and/or collectively, as column(s) 422) of cutting blades 412 that can facilitate and/or assist the surgical instrument 400 in performing an osteotomy. In various embodiments, the first surface 404 and the second surface 406 includes a suitable quantity of cutting blades 412 so that the surgical instrument 400 can perform an osteotomy in one cut and/or one pass.

In various embodiments, the first surface 404 includes a quantity of cutting blades 412A in the range of about 2 cutting blades 412A to about 40 cutting blades 412A, among other ranges of quantities of cutting blades 412A and/or quantities of cutting blades 412A that are possible and contemplated herein. In some embodiments, the first surface 404 includes 12 cutting blades 412A, among other quantities of cutting blades 412A that are possible and contemplated herein.

In additional embodiments, the second surface 406 includes a quantity of cutting blades 412B in the range of about 2 cutting blades 412B to about 40 cutting blades 412B, among other ranges of quantities of cutting blades 412B and/or quantities of cutting blades 412B that are possible and contemplated herein. In some embodiments, the second surface 406 includes 12 cutting blades 412B, among other quantities of cutting blades 412B that are possible and contemplated herein.

In various embodiments, the first surface 404 and the second surface 406 include the same quantity of cutting blades 412. In alternative embodiments, the first surface 404 and the second surface 406 include different quantities of cutting blades 412. In certain embodiments, the first surface 404 includes a greater quantity or lesser quantity of cutting blades 412 than the second surface 406 or vice versa.

While the surgical instrument 400 is shown with the first surface 404 and the second surface 406 each including 8 cutting blades 412, the various embodiments of the surgical instrument 400 are not limited to 8 cutting blades 412. That is, various other embodiments of a surgical instrument 400 can include a different quantity of cutting blades 412 such that the first surface 404 and/or the second surface 406 can include a greater quantity of cutting blades 412 than 8 cutting blades 412 and/or a smaller quantity of cutting blades 412 than 8 cutting blades 412.

In some embodiments, the cutting blades 412 may be included on the entirety or substantially the entirety of the first surface 404 and/or the second surface 406. In other embodiments, the cutting blades 412 may be included on a portion or at least a portion of the first surface 404 and/or second surface 406. That is, the cutting blades 412 may extend partially or fully from the distal end 408 to the proximal end 410 on the first surface 404 and/or the second surface 406.

In some embodiments, the cutting blades 412 extend fully from the distal end 408 to the proximal end 410 on both the first surface 404 and the second surface 406. In other embodiments, the cutting blades 412 extend partially from the distal end 408 to the proximal end 410 on both the first surface 404 and the second surface 406. In still other embodiments, the cutting blades 412A extend fully from the distal end 408 to the proximal end 410 on the first surface 404 and the cutting blades 412B extend partially from the distal end 408 to the proximal end 410 on the second surface 406. In still further embodiments, the cutting blades 412B extend fully from the distal end 408 to the proximal end 410 on the second surface 406 and the cutting blades 412A extend partially from the distal end 408 to the proximal end 410 on the first surface 404.

The portion of the first surface 404 and/or the second surface 406 including the cutting blades 412 may include any suitable sized portion that can produce a wedge-shaped, a straight-cut osteotomy, and/or a parallel-cut osteotomy. Various embodiments of the surgical instrument 400 may include varying sized portions of the first surface 404 and/or the second surface 406 including the cutting blades 412 so that different sized and/or shaped osteotomies can be obtained.

In some embodiments, the first surface 404 and the second surface 406 include the same sized portions of cutting blades 412. In other embodiments, the first surface 404 and the second surface 406 include different sized portions of cutting blades 412. In still other embodiments, the first surface 404 includes a larger sized portion or smaller sized portion of cutting blades 412 than the second surface 406 or vice versa.

In various embodiments, the body 402 includes a length L4 (see, FIG. 4B) in the range of about 15 mm to about 70 mm, among other ranges of length and/or lengths that are possible and contemplated herein. In some embodiments, the body 402 includes a length L4 of about 20 mm, among other lengths that are possible and contemplated herein.

The body 402 further includes a width W7 (see, FIG. 4B) at the distal end 408 and a width W8 (see, FIG. 4B) at the proximal end 410. In various embodiments, the width W7 is in the range of about 5 mm to about 30 mm, among other ranges of widths and/or widths that are possible and contemplated herein. In some embodiments, the width W7 is about 7.5 mm, among other widths that are possible and contemplated herein.

In additional or alternative embodiments, the width W8 is in the range of about to about 70 mm, among other ranges of widths and/or widths that are possible and contemplated herein. In some embodiments, the width W8 is about 11 mm, among other widths that are possible and contemplated herein.

In some embodiments, the width W7 and the width W8 are the same width or substantially the same width. In other embodiments, the width W8 is greater than the width W7 such that the proximate end 410 is wider than the distal end 408 or, alternatively, the distal end 408 is narrower than the proximate end 410 (e.g., the width W7 is less than the width W8). That is, in various embodiments, the surgical instrument 400 includes a tapered shape and/or tapers from the distal end 408 to the proximate end 410.

A first surface 404 may include any suitable profile upon which one or more cutting blades 412A can be positioned. In various embodiments, the first surface 404 includes a slope 418A (see, FIGS. 4E and 4F) that extends upward and/or away from a reference plane 425 (e.g., a flat plane or 0° plane) and the distal end 408. The slope 418A may include any suitable grade (e.g., rise over run) that can facilitate and/or assist the surgical instrument 400 in performing an osteotomy. That is, the first surface 404 and/or surgical instrument 400 may include any suitable grade that can facilitate and/or assist the surgical instrument 400 in performing an osteotomy in one cut and/or one pass.

Figure 4A:
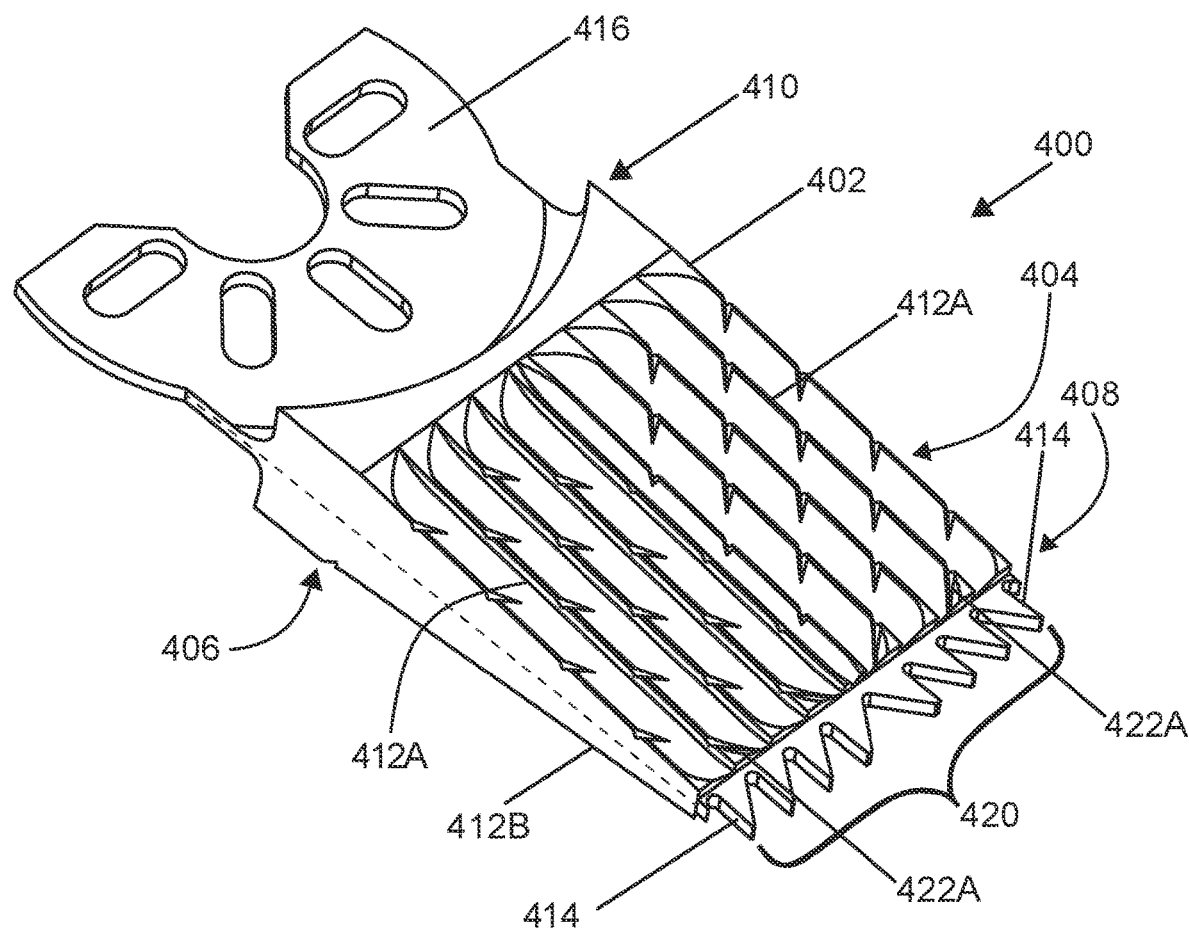
Figure 4B:
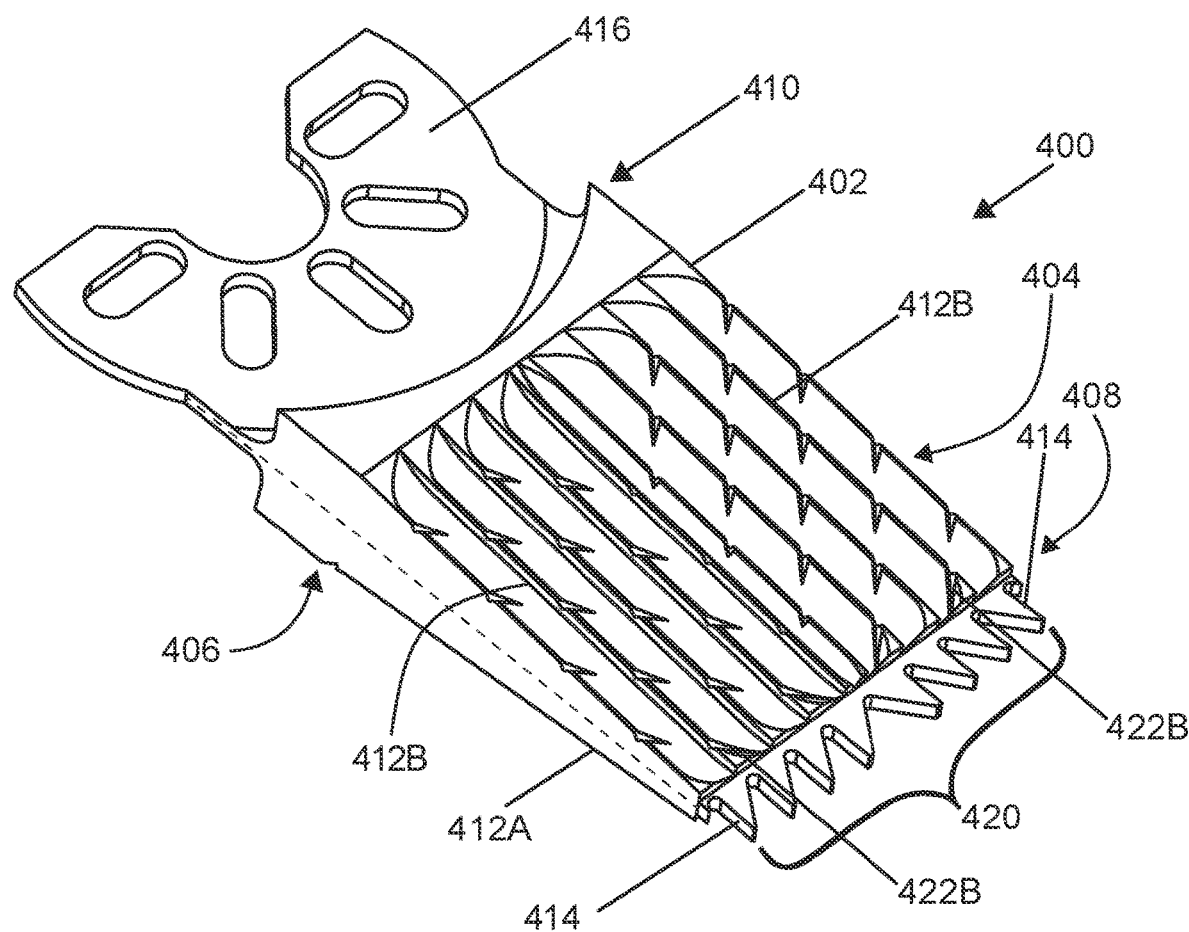
Figure 4C:
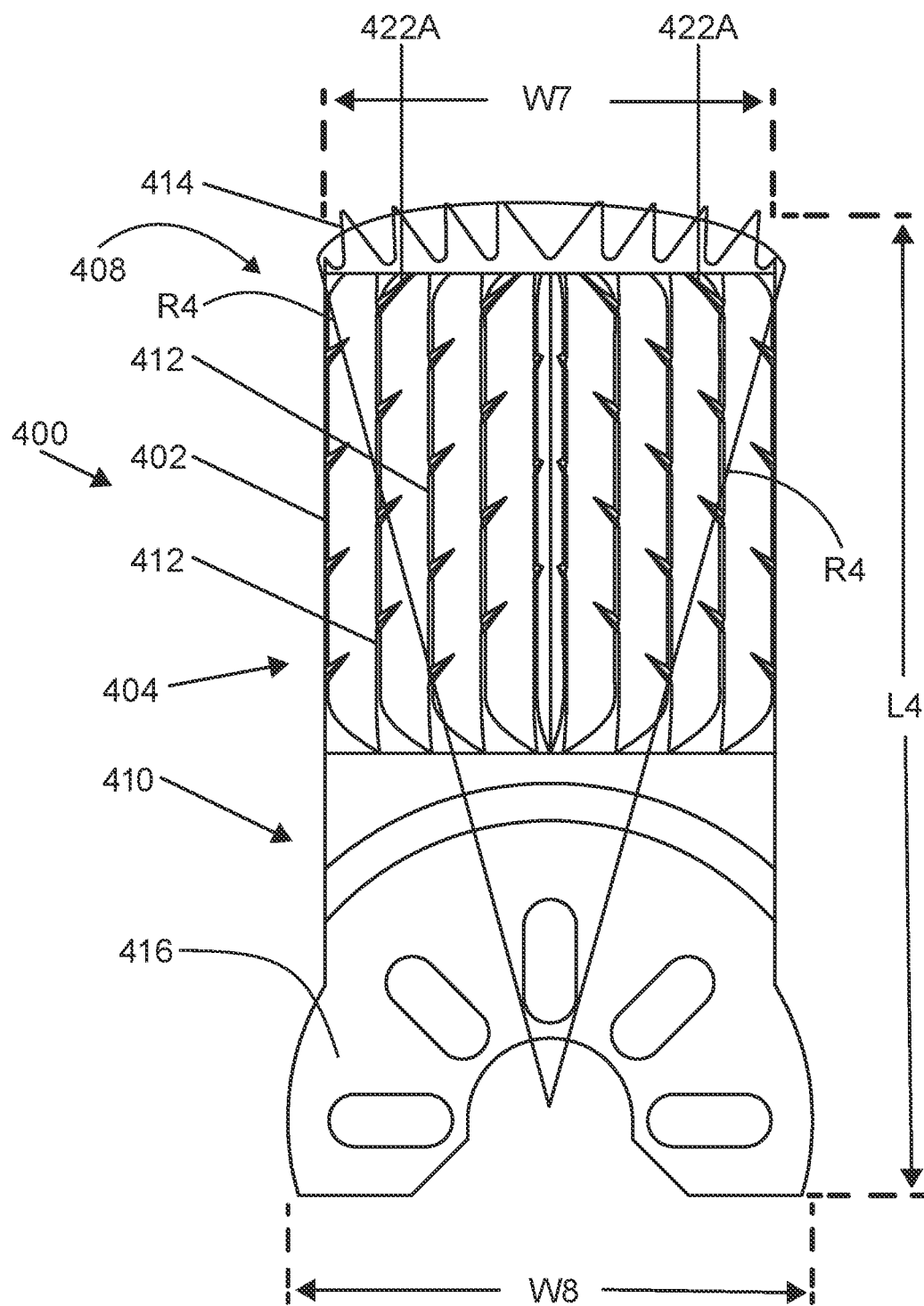
Figure 4D:
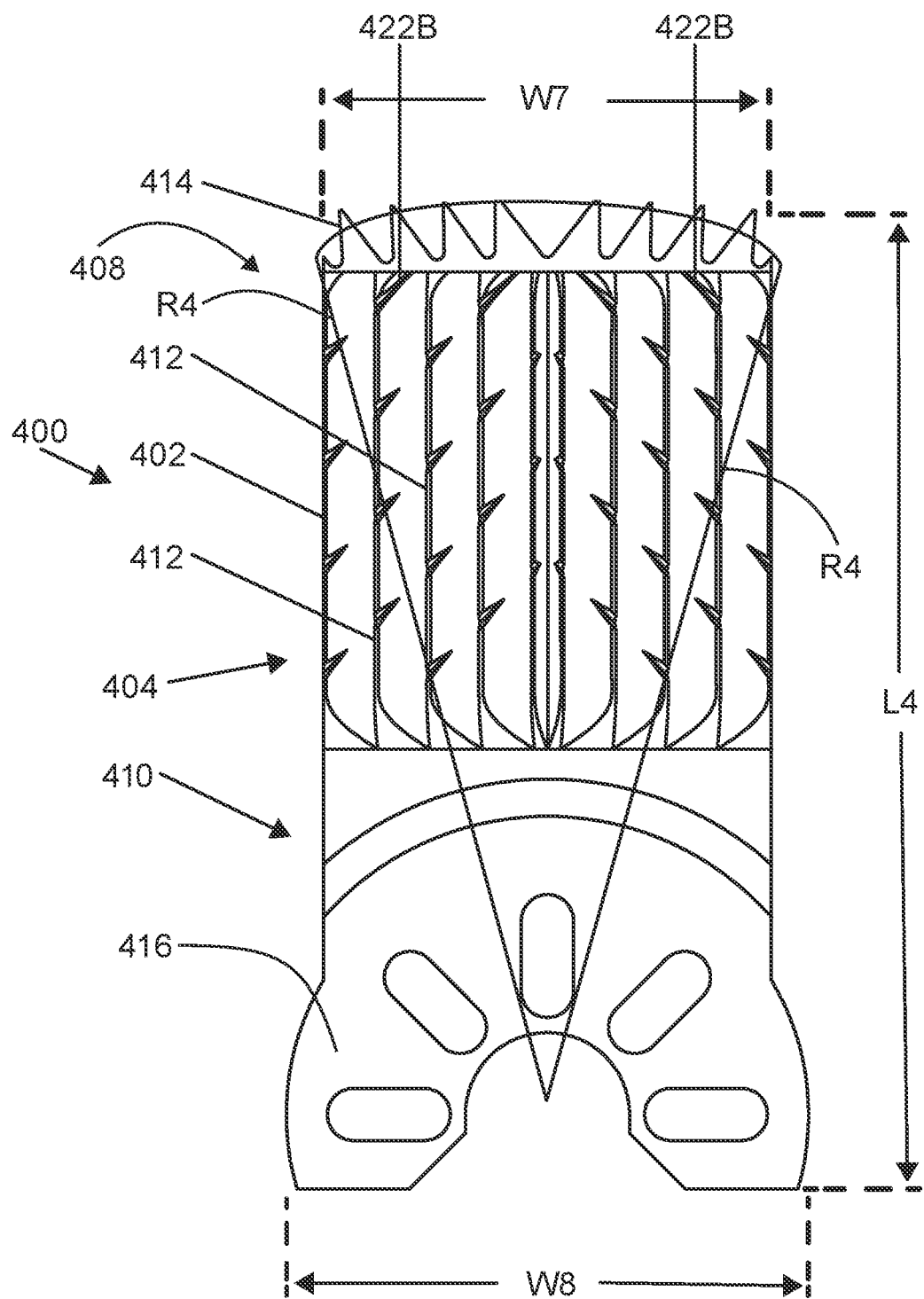
Figure 4F:
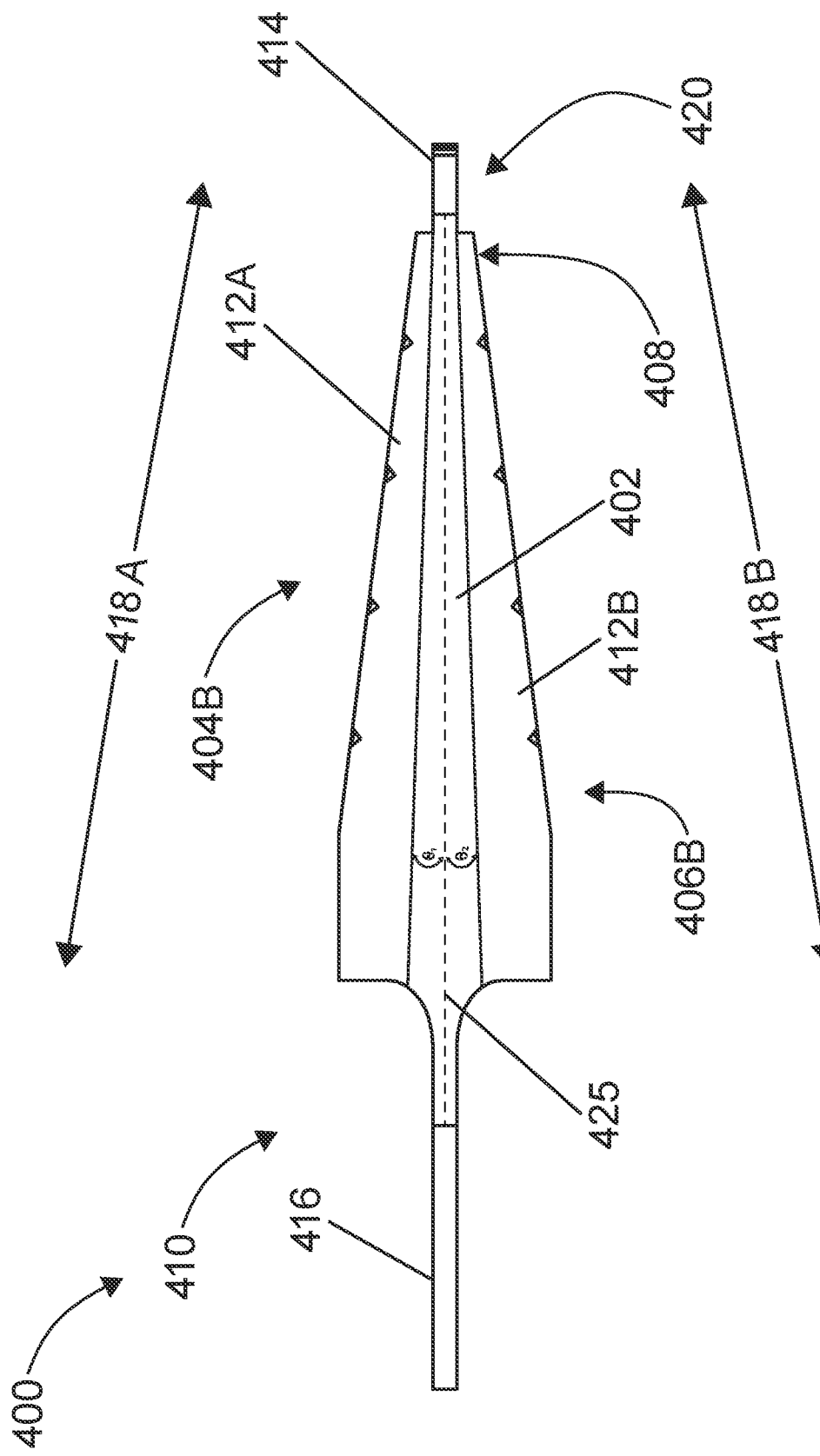

In various embodiments, the slope 418A includes a grade in the range of about zero degrees (0° or flat) to about fifteen degrees (15°), among other ranges of grades, grades, and/or slopes that are possible and contemplated herein. In other words, an angle $\theta_1$ in the range of about 0° to about 15° (e.g., the angle $\theta_1$=0°, 1°, 2°, 3°, 4°, 5°, 6°, 7°, 8°, 9°, 10°, 11°, 12°, 13°, 14°, or 15° and/or the angle $\theta_1 \approx$ 0°, 1°, 2°, 3°, 4°, 5°, 6°, 7°, 8°, 9°, 10°, 11°, 12°, 13°, 14°, or 15°) is defined between the reference plane 425 and the first surface 404 beginning at the distal end 408 and extending upward and toward the proximate end 410, as shown in FIGS. 4E and 4F. In some embodiments, the slope 418A includes a grade of about seven degrees (7°) (e.g., the angle $\theta_1$=7° or the angle $\theta_1 \approx$ 7°), among other suitable grades and/or slopes that are possible and contemplated herein.

A second surface 406 may include any suitable profile upon which one or more cutting blades 412B can be positioned. In various embodiments, the second surface 406 includes a slope 418B (see, FIGS. 4E and 4F) that extends upward and/or away from the reference plane 425 and the distal end 408. The slope 418B may include any suitable grade (e.g., rise over run) that can facilitate and/or assist the surgical instrument 400 in performing an osteotomy. That is, the second surface 406 and/or surgical instrument 400 may include any suitable grade that can facilitate and/or assist the surgical instrument 400 in performing an osteotomy in one cut and/or one pass.

In various embodiments, the slope 418B includes a grade in the range of about zero degrees (0° or flat) to about fifteen degrees (15°), among other ranges of grades, grades, and/or slopes that are possible and contemplated herein. In other words, an angle $\theta_2$ in the range of about 0° to about 15° (e.g., the angle $\theta_2$=0°, 1°, 2°, 3°, 4°, 5°, 6°, 7°, 8°, 9°, 10°, 11°, 12°, 13°, 14°, or 15° and/or the angle $\theta_2 \approx$ 0°, 1°, 2°, 3°, 4°, 5°, 6°, 7°, 8°, 9°, 10°, 11°, 12°, 13°, 14°, or 15°) is defined between the reference plane 425 and the second surface 406 beginning at the distal end 408 and extending upward and toward the proximate end 410, as shown in FIGS. 4E and 4F. In some embodiments, the slope 418B includes a grade of about 7° (e.g., the angle $\theta_2$=7° or the angle $\theta_2 \approx$ 7°), among other suitable grades and/or slopes that are possible and contemplated herein.

In various embodiments, the angles $\theta_1$ and $\theta_2$ include the same angle with respect to the reference plane 425. In alternative embodiments, the angles $\theta_1$ and $\theta_2$ include different angles with respect to the reference plane 425. In certain embodiments, the angle $\theta_1$ is greater than the angle $\theta_2$ or vice versa.

In some embodiments (see, e.g., FIG. 4E), the angles $\theta_1$ and $\theta_2$ are each greater than 0° such that neither of slopes 418A and 418B define a flat surface for the first surface 404 and the second surface 406 (e.g., the first surface 404 and the second surface 406 are not parallel to the reference plane 425). Here, the angles $\theta_1$ and $\theta_2$ can include the same angle greater than 0° or different angles greater than 0° with respect to the reference plane 425.

In other embodiments (see, e.g., FIG. 4F), angle $\theta_1$ and $\theta_2$ are each 0°. Here, the slope 418A defines a flat surface for the first surface 404 and the slope 418B defines a flat surface of the second surface 406 (e.g., first surface 404 and second surface 406 are parallel to the reference plane 425).

In still other embodiments, angle $\theta_1$ or angle $\theta_2$ is 0° and the other one of angle $\theta_1$ or angle $\theta_2$ greater than 0° with respect to the reference angle 425. Here, the slope 418A for the first surface 404 or the slope 418B for the second surface 406 defines a non-flat or sloped surface for the first surface 404 or second surface 406, respectively, with respect to the reference angle 425 and the other one of the first surface 404 or the second surface 406 includes a flat surface (e.g., is parallel to the reference angle 425).

In various embodiments, the distal end 408 includes a set of cutting teeth 414 (e.g., a single tooth 414 or multiple teeth 414) positioned thereon. A set of cutting teeth 414 may include any suitable quantity of teeth 414 that can assist in and/or facilitate initiating an osteotomy and particularly, a wedge-shaped osteotomy, when oscillated.

In various embodiments, the set of cutting teeth 414 includes a quantity of cutting teeth 414 in the range of one (1) cutting tooth 414 to about 50 cutting teeth 414, among other ranges of quantities and/or quantities of cutting teeth 414 that are possible and contemplated herein. In some embodiments, a set of cutting teeth 414 includes about 8 cutting teeth 414, among other quantities of cutting teeth 414 that are possible and contemplated herein.

In some embodiments, the set of cutting teeth 414 are positioned on the distal end 408 in a straight line or substantially straight line. In other embodiments, the set of cutting teeth 414 are positioned along a curve on the distal end 408 defined by a radius R1.

The radius R4 may be any suitable radius and/or curvature that can assist in and/or facilitate initiating an osteotomy (e.g., a wedge-shaped osteotomy) when oscillated. In various embodiments, the radius R4 is in the range of about 5 mm to about 80 mm, among other ranges of lengths and/or lengths that can define an amount and/or degree of curvature that are possible and contemplated herein. In some embodiments, the radius R4 is about 25 mm, among other lengths that can define an amount and/or degree of curvature that are possible and contemplated herein.

In some embodiments, the set of cutting teeth 414 on the distal end 408 may define a cutting tip 120 that can initiate an osteotomy (e.g., a wedge osteotomy). Further, the cutting blades 412A positioned along the slope 118A and/or the cutting blades 412B positioned along the slope 118B may define a cutting slope 118A and/or 118B, respectively, that can perform an osteotomy. In various embodiments, the coordination of the cutting tip 420 and the cutting slopes 118A and 118B can allow the surgical instrument 400 to produce a wedge-shaped osteotomy, a straight-cut osteotomy, and/or a parallel-cut osteotomy in a single cut and/or single pass.

As further shown, the proximal end 410 includes an attachment mechanism 416 positioned thereon. The attachment mechanism 416 may include any suitable size dimensions, shape, and/or configuration that enables attachments of the surgical instrument 400 to a surgical instrument (not shown). That is, while the attachment mechanism 416 is shown as including particular relative size dimensions, shapes, and configurations, the various embodiments of the surgical instrument 400 are not limited to the illustrated attachment mechanism 416. That is, other embodiments of the surgical instrument 400 may include one or more different relative size dimension(s), shapes, and/or configurations.

FIGS. 5A through 5F are schematic diagrams illustrating various views of various embodiments of a surgical instrument 500. In various embodiments, the surgical instrument 500 can be utilized to perform a wedge-shaped osteotomy, a straight-cut osteotomy, and/or a parallel-cut osteotomy. Further, the wedge-shaped osteotomy, straight-cut osteotomy, and/or parallel-cut osteotomy can be achieved with a single cut or pass utilizing the surgical instrument 500.

A surgical instrument 500 may be constructed of any suitable material that can cut bone. In various embodiments, the surgical instrument 500 is constructed of a sterilized suitable material that can cut bone. In some embodiments, the surgical instrument 500 includes stainless steel, among other suitable materials and combinations of materials that are possible and contemplated herein. In additional or alternative embodiments, the surgical instrument 500 includes surgical grade stainless steel, among other suitable surgical grade materials and combinations of materials that are possible and contemplated herein.

At least in the embodiments illustrated in FIGS. 5A through 5F, the surgical instrument 500 includes, among other features, a body 402, a distal end 408, a proximal end 410, and an attachment mechanism 416 similar to the body 402, distal end 408, proximal end 410, and attachment mechanism 416 of the various embodiments of the surgical instrument 400 discussed herein with reference to FIGS. 4A through 4F. A surgical instrument 500 further includes, among other features and/or elements, a first surface 504 including a set of cutting blades 512A positioned thereon and a second surface 506 including a set of cutting blades 512B positioned thereon (see, e.g., FIG. 5A).

A cutting blade 512A and 512B may include similar features and/or dimensions as the cutting blades 412A and 412B discussed with reference to FIGS. 4A through 4F. In addition, the cutting blades 512A on the first surface 504 and the cutting blades 512B on the second surface 506 may include the quantities and/or relative quantities as the cutting blades 412A on the first surface 404 and the cutting blades 412B on the second surface 406 discussed with reference to FIGS. 4A through 4F.

Figure 5A:
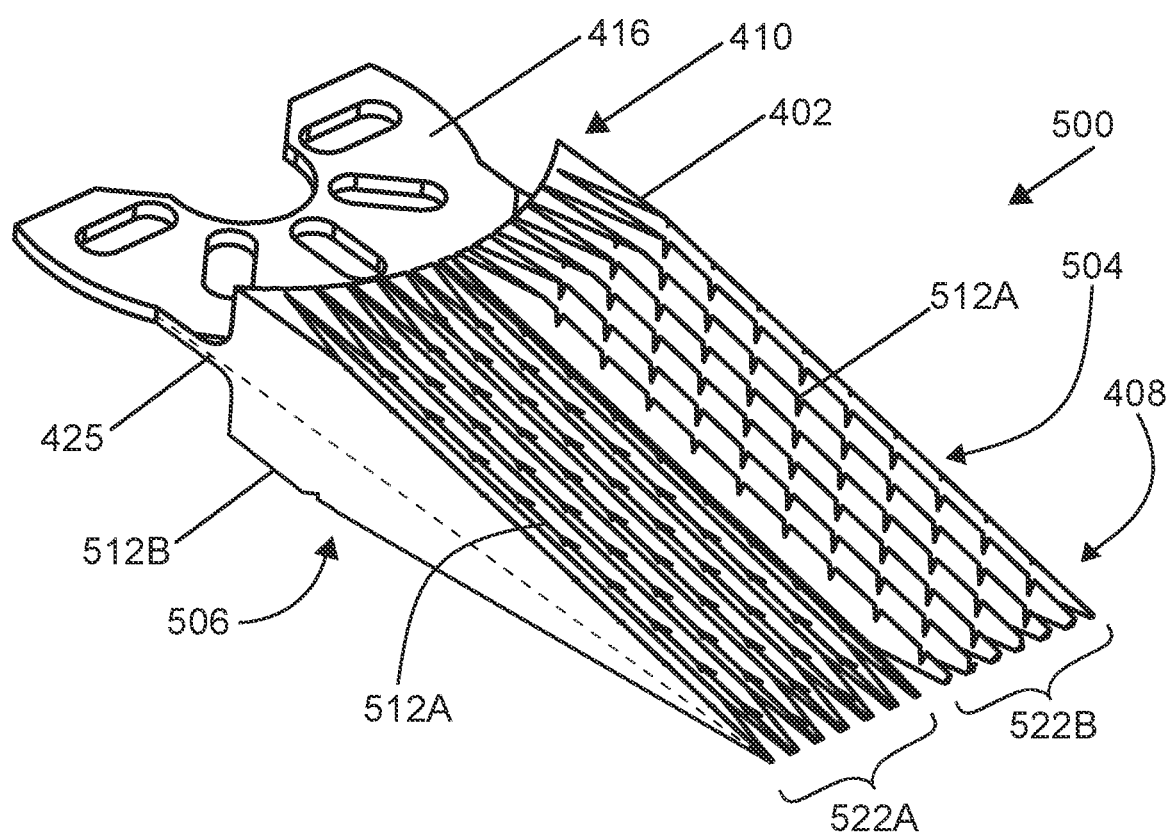
FIGS. 5A through 5F are schematic diagram illustrating various other embodiments of a double-sided surgical instrument including multiple columns of cutting blades.
Figure 5B:
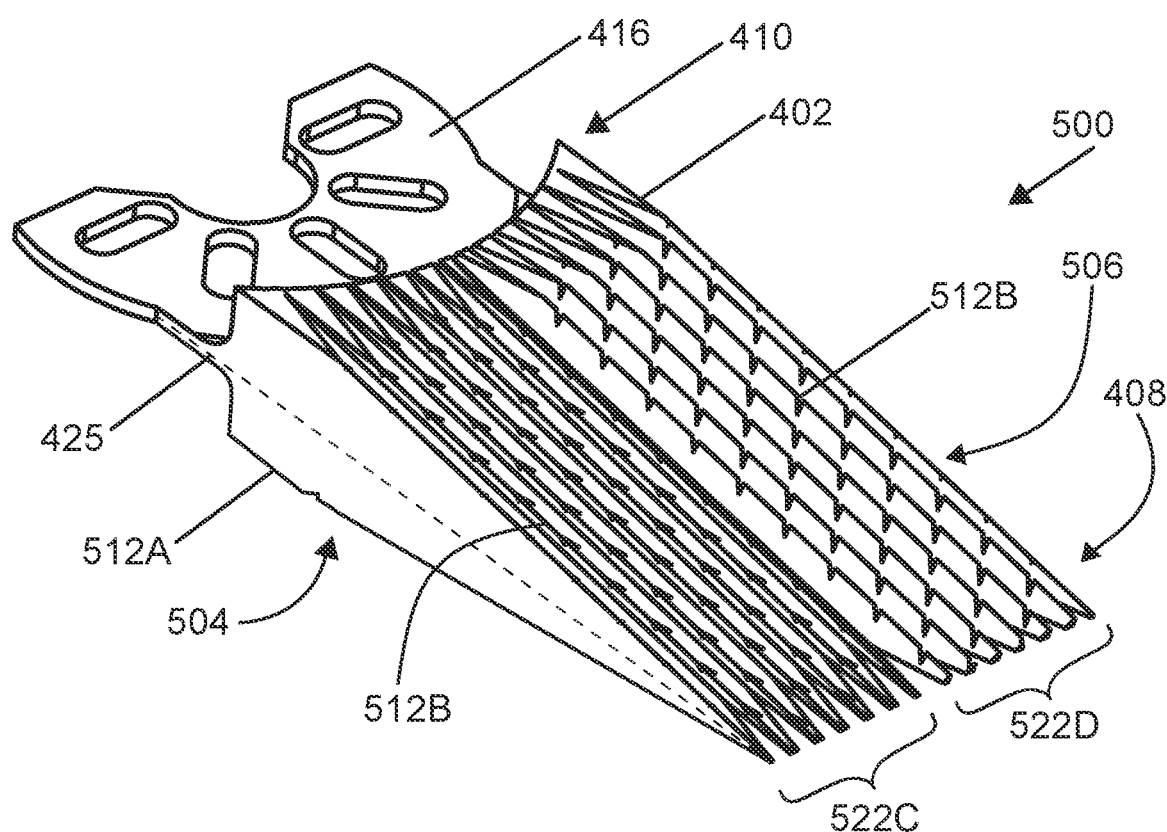
Figure 5C:
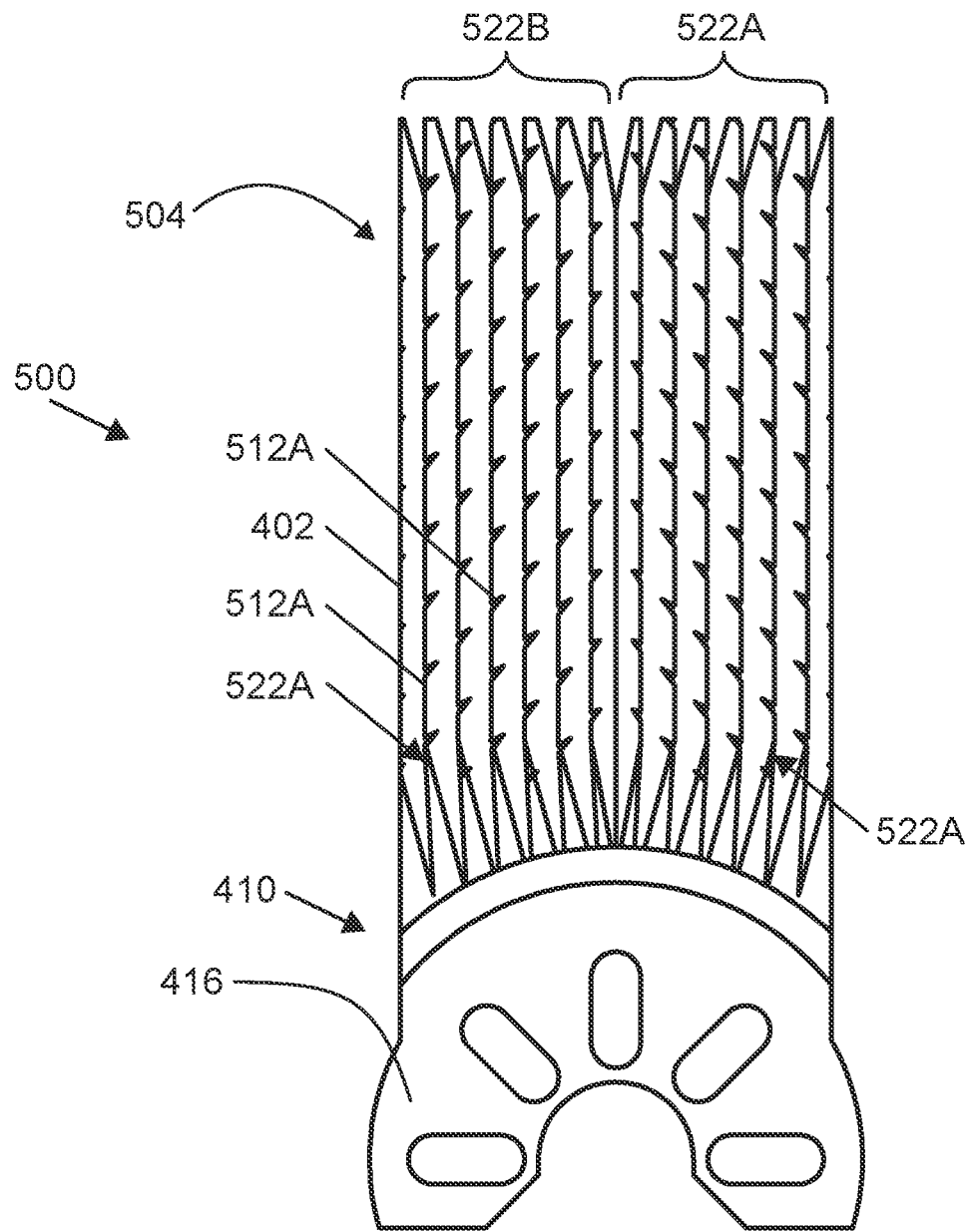

In FIGS. 5A and 5C, one or more columns 522A of cutting blades 512A (e.g., 4 cutting blades 512A) forms a set of columns 522C that is/are oriented outward toward the left (e.g., is/are not perpendicular to the first surface 504) and one or more columns 522A of cutting blades 512A (e.g., 4 cutting blades 512A) forms a set of columns 522D are oriented outward toward the right and/or away from the blade(s) 512A oriented outwardly toward the left (e.g., is/are not perpendicular to the first surface 504), among other quantities, relative quantities, and/or orientation(s) of cutting blades 512A that are possible and contemplated herein.

Figure 5D:
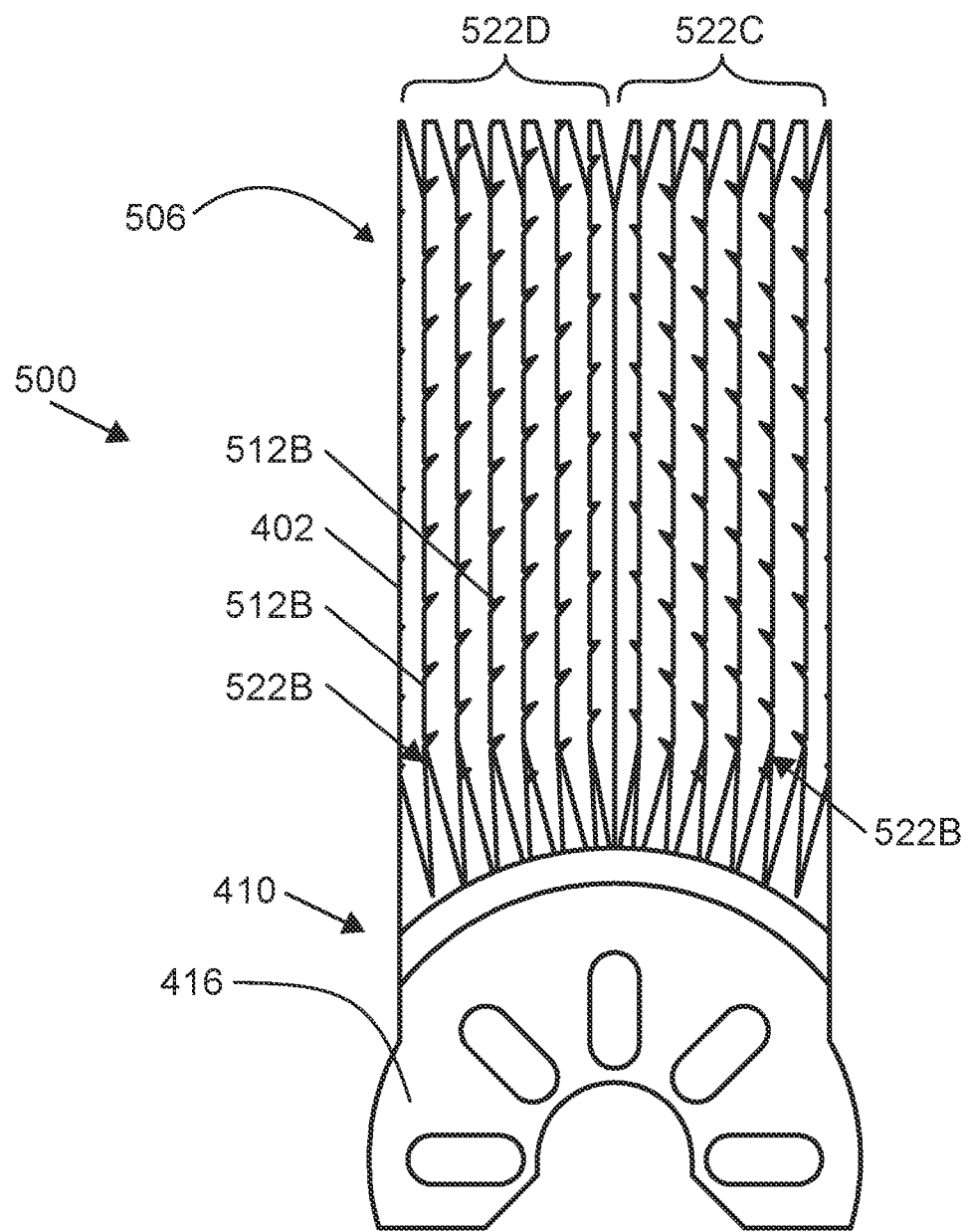

In FIGS. 5B and 5D, one or more columns 522B of cutting blades 512B (e.g., 4 cutting blades 512B) forms a set of columns 522E that is/are oriented outward toward the left (e.g., is/are not perpendicular to the second surface 506) and one or more columns 522B of cutting blades 512B (e.g., 4 cutting blades 512B) forms a set of columns 522F are oriented outward toward the right and/or away from the blade(s) 512B oriented outwardly toward the left (e.g., is/are not perpendicular to the second surface 506), among other quantities, relative quantities, and/or orientation(s) of cutting blades 512B that are possible and contemplated herein.

In various embodiments, the cutting blades 512A can include a portion at the distal end 408 that functions similar to the cutting teeth 414 and/or cutting tip 420 discussed with reference to FIGS. 4A through 4F. In additional or alternative embodiments, the cutting blades 512B can include a portion at the distal end 408 that functions similar to the cutting teeth 414 and/or cutting tip 420 discussed with reference to FIGS. 4A through 4F.

As shown, various embodiments of the surgical instrument 500 include the angles $\theta_1$ and $\theta_2$ similar to the various embodiments of the surgical instrument 400. In some embodiments, all of the cutting blades 512A on the first surface 504 include a uniform height (see, e.g., FIG. 5E). In alternative embodiments, one or more of the cutting blades 512A on the first surface 504 include a height that gradually increases from the distal end 408 to the proximal end 410 (see, e.g., FIG. 5F).

Figure 5E:
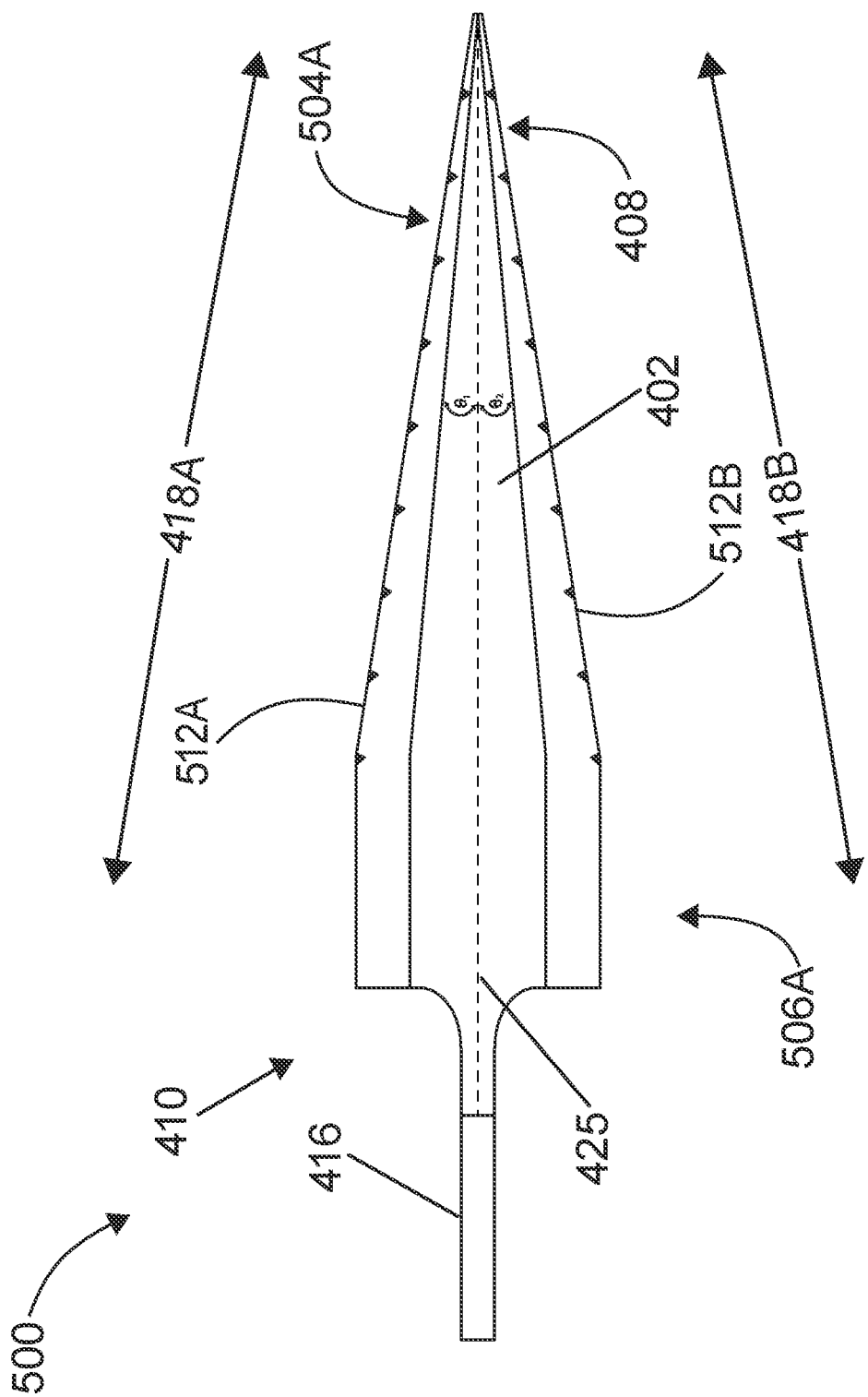
Figure 5F:
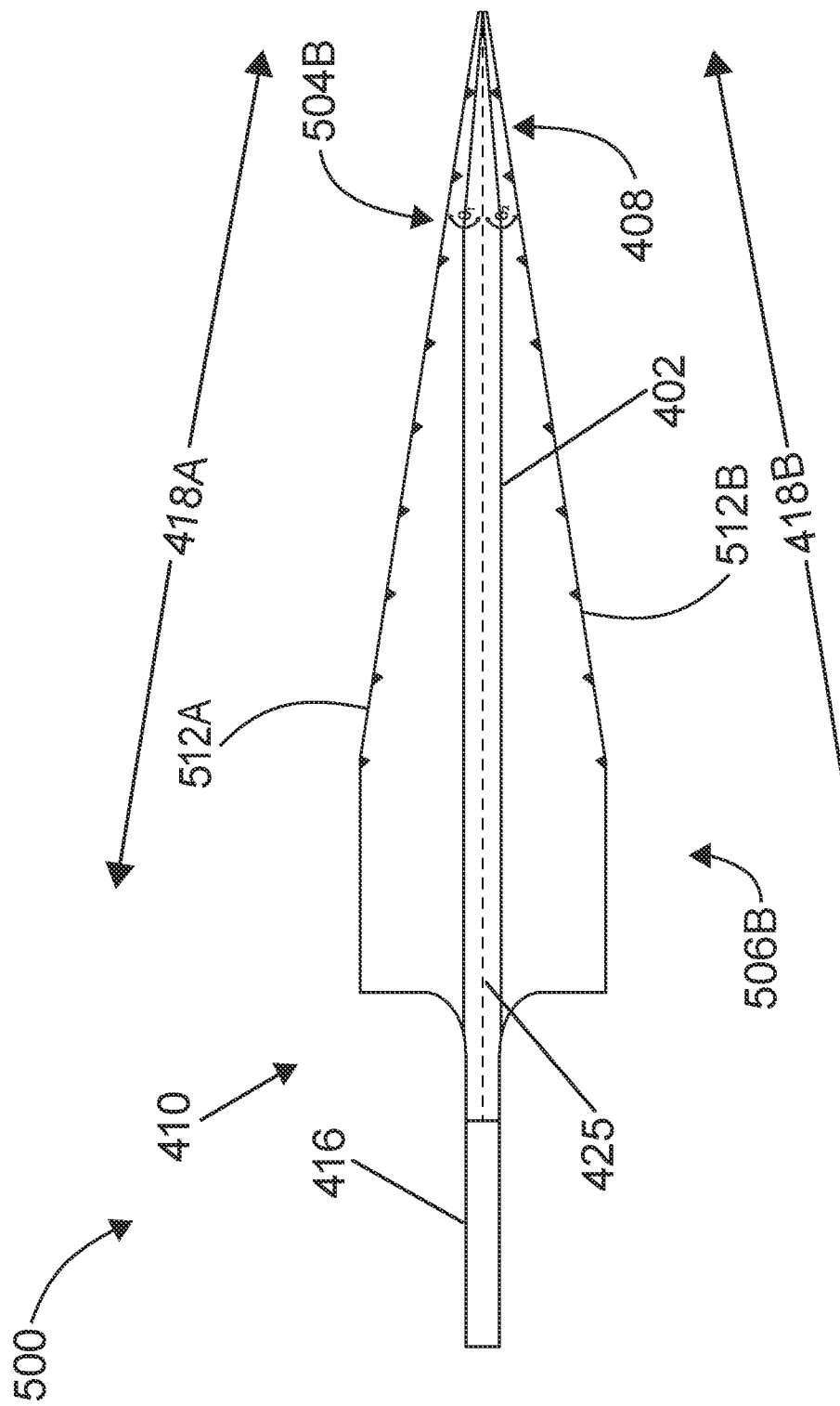

In additional embodiments, all of the cutting blades 512B on the second surface 506 include a uniform height (see, e.g., FIG. 5E). In alternative embodiments, one or more of the cutting blades 512B on the second surface 506 include a height that gradually increases from the distal end 408 to the proximal end 410 (see, e.g., FIG. 5F).

In further embodiments, all of the cutting blades 512 on the first surface 504 and the second surface 506 include a uniform height, which can be the same and/or different uniform heights from one another. In other embodiments, all of the cutting blades 512 on the first surface 504 and the second surface 506 include gradually increasing heights, which can be the same and/or different gradually increasing heights from one another. In still further embodiments, one or more of the cutting blades 512A on the first surface 504 can include uniform heights and/or gradually increasing heights and one or more of the cutting blades 512B on the second surface 506 can include uniform heights and/or gradually increasing heights, and the various possible combinations thereof, which also includes the various combinations of the same and/or different gradually increasing heights on the first surface 504 and/or the second surface 506.

A set of cutting blades 512A and 512B may include any suitable quantity of cutting blades 512 and/or quantity of columns 522A and 422B (also referred to herein individually and/or collectively, as column(s) 522) of cutting blades 412 that can facilitate and/or assist the surgical instrument 500 in performing an osteotomy. In various embodiments, the first surface 504 and the second surface 506 includes a suitable quantity of cutting blades 512 so that the surgical instrument 500 can perform an osteotomy in one cut and/or one pass.

FIGS. 6A through 6F are schematic diagrams illustrating various views of various embodiments of a surgical instrument 600. In various embodiments, the surgical instrument 600 can be utilized to perform a wedge-shaped osteotomy, a straight-cut osteotomy, and/or a parallel-cut osteotomy. Further, the wedge-shaped osteotomy, straight-cut osteotomy, and/or parallel-cut osteotomy can be achieved with a single cut or pass utilizing the surgical instrument 600.

A surgical instrument 600 may be constructed of any suitable material that can cut bone. In various embodiments, the surgical instrument 600 is constructed of a sterilized suitable material that can cut bone. In some embodiments, the surgical instrument 600 includes stainless steel, among other suitable materials and combinations of materials that are possible and contemplated herein. In additional or alternative embodiments, the surgical instrument 600 includes surgical grade stainless steel, among other suitable surgical grade materials and combinations of materials that are possible and contemplated herein.

At least in the embodiments illustrated in FIGS. 6A through 6F, the surgical instrument 600 includes, among other features, a body 402, a distal end 408, a proximal end 410, a set of cutting teeth 414, an attachment mechanism 416, and a cutting tip 420 similar to the body 402, distal end 408, proximal end 410, the set of cutting teeth 414, attachment mechanism 416, and cutting tip 420 of the various embodiments of the surgical instrument 400 discussed herein with reference to FIGS. 4A through 4F.

Figure 6A:
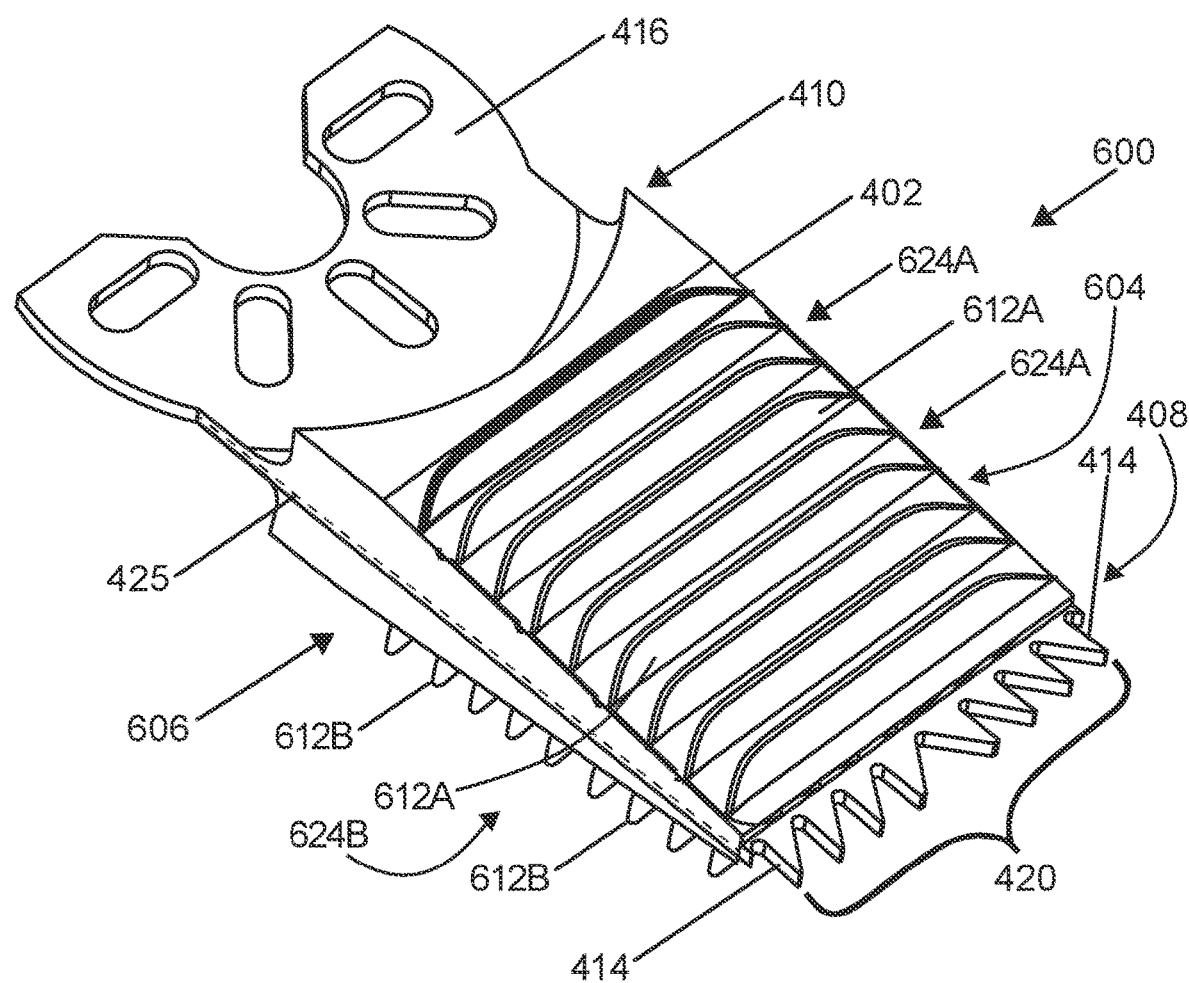
FIGS. 6A through 6D are schematic diagram illustrating various embodiments of a double-sided surgical instrument including multiple rows of cutting blades.

A surgical instrument 600 further includes, among other features and/or elements, a first surface 604 including a set of cutting blades 612A positioned thereon (see, e.g., FIG. 6A). As illustrated, the set of cutting blades 612A are spaced apart and positioned vertically and/or angles with respect to the first surface 604 to form a set of rows 424A of cutting blades 612A.

Figure 6B:
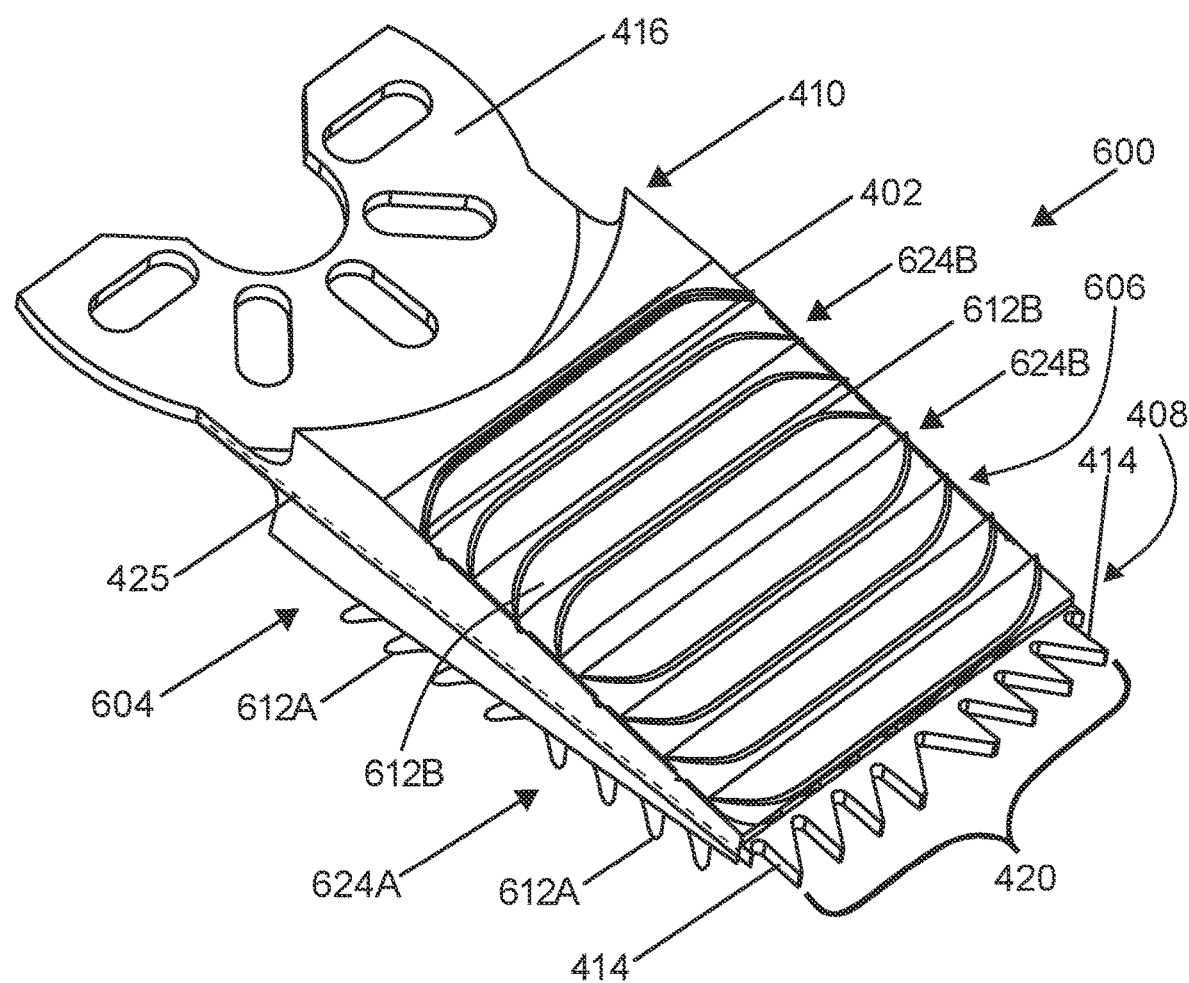

In further embodiments, the second surface 406 includes a set of cutting blades 612B positioned thereon. As illustrated in FIG. 6B, the set of cutting blades 612B are spaced apart and positioned vertically and/or angles with respect to the second surface 606 to form a set of rows 424B of cutting blades 612B.

A cutting blade 612A and 612B (also referred to herein individually and/or collectively, as cutting blade(s) 612) may include any suitable shape that can facilitate and/or assist the surgical instrument 600 in performing an osteotomy (e.g., a wedge-shaped osteotomy, a straight-cut osteotomy, and/or a parallel-cut osteotomy). In various embodiments, a cutting blade 612 can include a curved blade (e.g., a vertically curved blade), a straight blade, a single edge blade, a smooth edge blade, waved blade (e.g., a horizontally curved blade), or a wavy blade (e.g., a blade with multiple horizontal curves), among other suitable shapes that can facilitate cutting bone that are possible and contemplated herein. In additional or alternative embodiments, a cutting blade 612 can include a straight cutting edge and/or a serrated cutting edge, among other cutting edges that are possible and contemplated herein.

In some embodiments, all of the cutting blades 612A in the set of cutting blades 612A on the first surface 604 include the same or substantially the same shape. In alternative embodiments, at least two cutting blades 612A in the set of cutting blades 612A on the first surface 604 include different shapes or substantially different shapes.

In additional embodiments, all of the cutting blades 612B in the set of cutting blades 612B on the second surface 606 include the same or substantially the same shape. In alternative embodiments, at least two cutting blades 612B in the set of cutting blades 612B on the second surface 606 include different shapes or substantially different shapes.

In further embodiments, all of the cutting blades 612 on the first surface 604 and the second surface 606 include the same or substantially the same shape. In alternative embodiments, at least one cutting blade 612A on the first surface 604 includes a different shape or substantially different shape than at least one cutting blade 612B on the second surface 606.

A cutting blade 612 may include any suitable height that can facilitate and/or assist the surgical instrument 600 in performing an osteotomy. In various embodiments, a cutting blade 612 can include a height in the range of about 0.1 mm to about 30 mm, among other suitable heights that can facilitate cutting bone that are possible and contemplated herein. In some embodiments, a cutting blade 612 include a height of 0.75 mm.

Figure 6C:
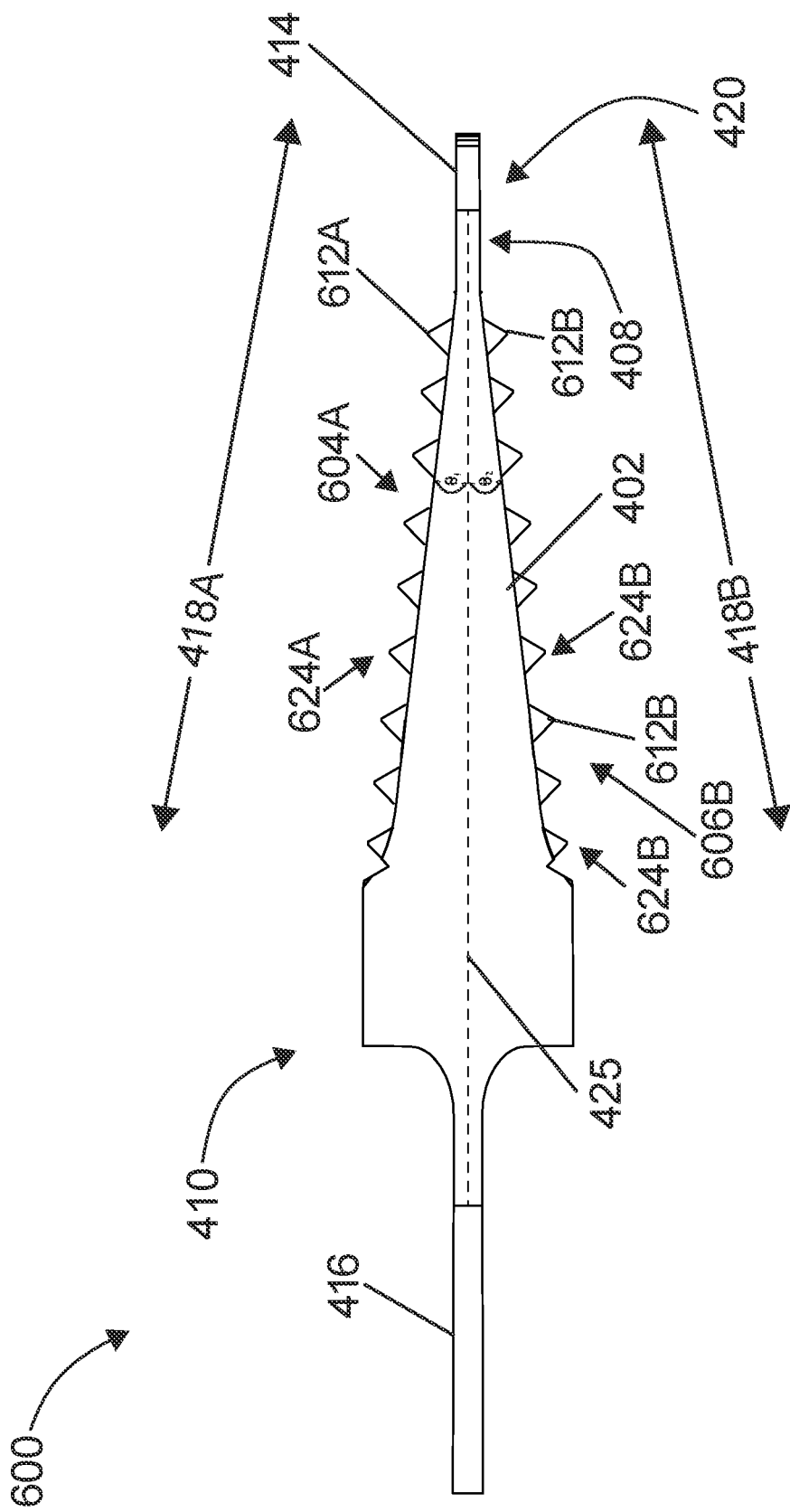
Figure 6D:
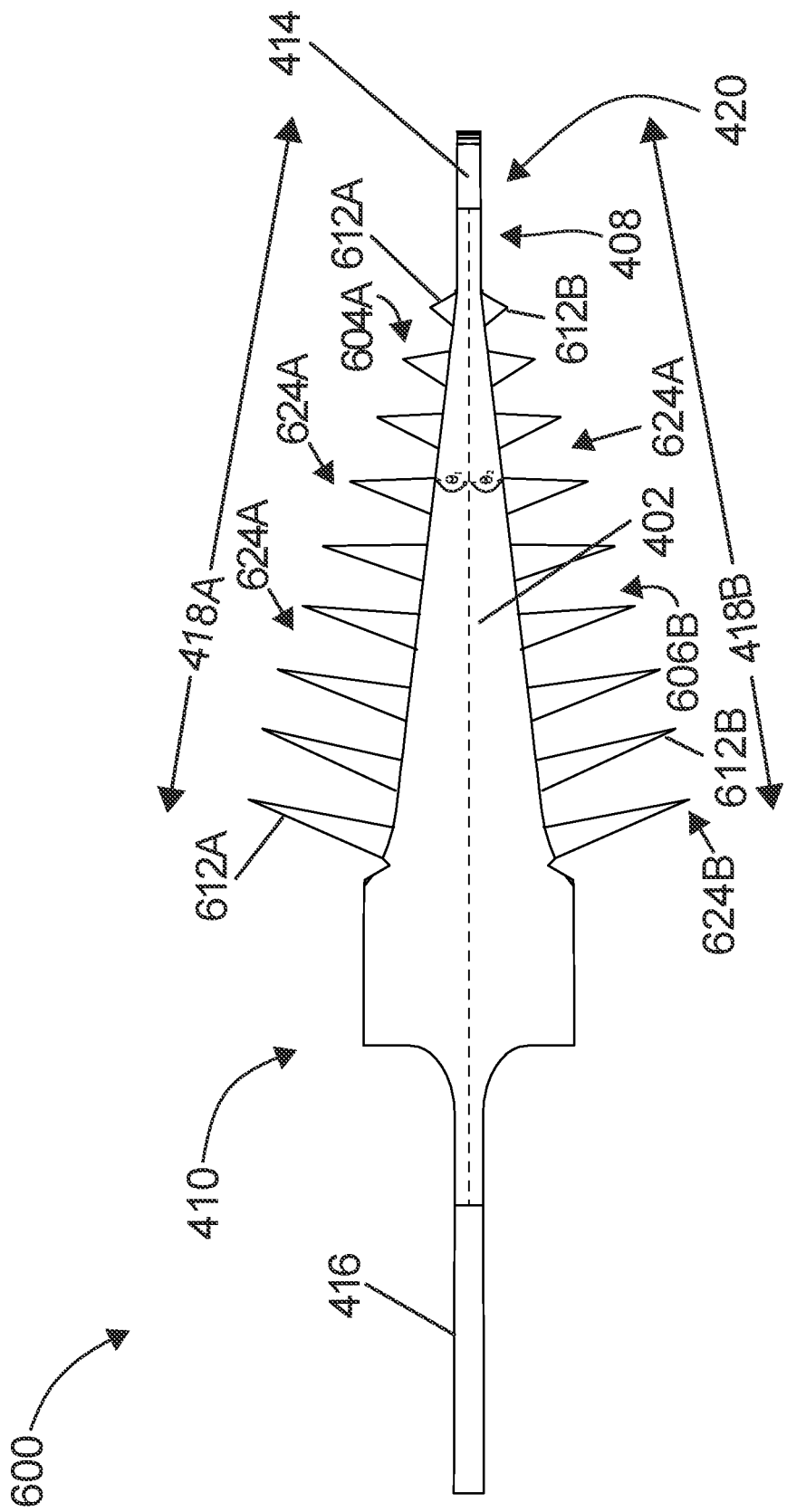

In some embodiments, all of the cutting blades 612A on the first surface 604 include a uniform height (see, e.g., FIG. 6C). In alternative embodiments, two or more rows 624A of the cutting blades 612A on the first surface 604 include a height that gradually increases from the distal end 408 to the proximal end 410 (see, e.g., FIG. 6D).

In additional embodiments, all of the cutting blades 612B on the second surface 606 include a uniform height (see, e.g., FIG. 6C). In alternative embodiments, two or more rows 624B of the cutting blades 612B on the second surface 606 include a height that gradually increases from the distal end 408 to the proximal end 410 (see, e.g., FIG. 6D).

In further embodiments, all of the cutting blades 612 on the first surface 604 and the second surface 606 include a uniform height, which can be the same and/or different uniform heights from one another. In other embodiments, two or more rows 624A and/or 624B of the cutting blades 612 on the first surface 604 and/or the second surface 606 include gradually increasing heights, which can be the same and/or different gradually increasing heights from one another. In still further embodiments, the cutting blades 612A on the first surface 404 can include uniform heights and/or rows 624A of gradually increasing heights and the cutting blades 612B on the second surface 406 can include uniform heights and/or rows 624B of gradually increasing heights, and the various possible combinations thereof, which also includes the various combinations of the same and/or different gradually rows 624 of increasing heights on the first surface 604 and/or the second surface 606.

A set of cutting blades 612 may include any suitable quantity of cutting blades 612 and/or quantity of rows 624A and 624B (also referred to herein individually and/or collectively, as column(s) 624) of cutting blades 612 that can facilitate and/or assist the surgical instrument 600 in performing an osteotomy. In various embodiments, the first surface 604 and the second surface 606 includes a suitable quantity of cutting blades 612 so that the surgical instrument 600 can perform an osteotomy in one cut and/or one pass.

In various embodiments, the first surface 604 includes a quantity of cutting blades 612A in the range of about 2 cutting blades 612A to about 40 cutting blades 612A, among other ranges of quantities of cutting blades 612A and/or quantities of cutting blades 612A that are possible and contemplated herein. In some embodiments, the first surface 604 includes 12 cutting blades 612A, among other quantities of cutting blades 612A that are possible and contemplated herein.

In additional embodiments, the second surface 606 includes a quantity of cutting blades 612B in the range of about 2 cutting blades 612B to about 40 cutting blades 612B, among other ranges of quantities of cutting blades 612B and/or quantities of cutting blades 612B that are possible and contemplated herein. In some embodiments, the second surface 606 includes 12 cutting blades 612B, among other quantities of cutting blades 612B that are possible and contemplated herein.

In various embodiments, the first surface 604 and the second surface 606 include the same quantity of cutting blades 612. In alternative embodiments, the first surface 604 and the second surface 606 include different quantities of cutting blades 612. In certain embodiments, the first surface 604 includes a greater quantity or lesser quantity of cutting blades 612 than the second surface 606 or vice versa.

While the surgical instrument 600 is shown with the first surface 604 and the second surface 606 each including 9 cutting blades 612, the various embodiments of the surgical instrument 600 are not limited to 9 cutting blades 612. That is, various other embodiments of a surgical instrument 600 can include a different quantity of cutting blades 612 such that the first surface 604 and/or the second surface 606 can include a greater quantity of cutting blades 612 than 9 cutting blades 612 and/or a smaller quantity of cutting blades 612 than 9 cutting blades 612.

In some embodiments, the cutting blades 612 may be included on the entirety or substantially the entirety of the first surface 604 and/or the second surface 606. In other embodiments, the cutting blades 612 may be included on a portion or at least a portion of the first surface 604 and/or second surface 606. That is, the cutting blades 612 may extend partially or fully from the distal end 408 to the proximal end 410 on the first surface 604 and/or the second surface 606.

In some embodiments, the cutting blades 612 extend fully from the distal end 408 to the proximal end 410 on both the first surface 604 and the second surface 606. In other embodiments, the cutting blades 612 extend partially from the distal end 408 to the proximal end 410 on both the first surface 604 and the second surface 606. In still other embodiments, the cutting blades 612A extend fully from the distal end 408 to the proximal end 410 on the first surface 604 and the cutting blades 412B extend partially from the distal end 408 to the proximal end 410 on the second surface 606. In still further embodiments, the cutting blades 612B extend fully from the distal end 408 to the proximal end 410 on the second surface 606 and the cutting blades 612A extend partially from the distal end 408 to the proximal end 410 on the first surface 604.

The portion of the first surface 604 and/or the second surface 606 including the cutting blades 612 may include any suitable sized portion that can produce a wedge-shaped, a straight-cut osteotomy, and/or a parallel-cut osteotomy. Various embodiments of the surgical instrument 600 may include varying sized portions of the first surface 604 and/or the second surface 606 including the cutting blades 612 so that different sized and/or shaped osteotomies can be obtained.

In some embodiments, the first surface 604 and the second surface 606 include the same sized portions of cutting blades 612. In other embodiments, the first surface 604 and the second surface 606 include different sized portions of cutting blades 612. In still other embodiments, the first surface 604 includes a larger sized portion or smaller sized portion of cutting blades 612 than the second surface 606 or vice versa.

A first surface 604 may include any suitable profile upon which one or more cutting blades 612A can be positioned. In various embodiments, the first surface 604 includes a slope 418A that extends upward and/or away from a reference plane 425 and the distal end 408 similar to the various embodiments discussed with reference to the surgical instrument 400.

A second surface 606 may include any suitable profile upon which one or more cutting blades 612B can be positioned. In various embodiments, the second surface 606 includes a slope 418B that extends upward and/or away from the reference plane 425 and the distal end 408 similar to the various embodiments discussed with reference to the surgical instrument 400.

In some embodiments (see, e.g., FIG. 6C), the angles $\theta_1$ and $\theta_2$ are each greater than 0° such that neither of slopes 418A and 418B define a flat surface for the first surface 604 and the second surface 606 (e.g., the first surface 604 and the second surface 606 are not parallel to the reference plane 425). Here, the angles $\theta_1$ and $\theta_2$ can include the same angle greater than 0° or different angles greater than 0° with respect to the reference plane 425.

In other embodiments (see, e.g., FIG. 6D), angle $\theta_1$ and $\theta_2$ are each 0°. Here, the slope 418A can define a flat surface for the first surface 604 and the slope 418B can define a flat surface of the second surface 606 (e.g., first surface 604 and second surface 606 are parallel to the reference plane 425).

In still other embodiments, angle $\theta_1$ or angle $\theta_2$ is 0° and the other one of angle $\theta_1$ or angle $\theta_2$ greater than 0° with respect to the reference angle 425. Here, the slope 418A for the first surface 604 or the slope 418B for the second surface 606 defines a non-flat or sloped surface for the first surface 604 or second surface 606, respectively, with respect to the reference angle 425 and the other one of the first surface 604 or the second surface 606 includes a flat surface (e.g., is parallel to the reference angle 425).

FIGS. 7A through 7D are diagrams of various embodiments of a surgical instrument 700. In the various embodiments illustrated in FIGS. 7A through 7D, the surgical instrument 700 includes among other features, a body 402, a distal end 408, a proximal end 410, a set of cutting teeth 414, an attachment mechanism 416, and a cutting tip 420 similar to the body 402, distal end 408, proximal end 410, the set of cutting teeth 414, attachment mechanism 416, and cutting tip 420 of the various embodiments of the surgical instrument 400 discussed herein with reference to FIGS. 4A through 4F.

Figure 7A:
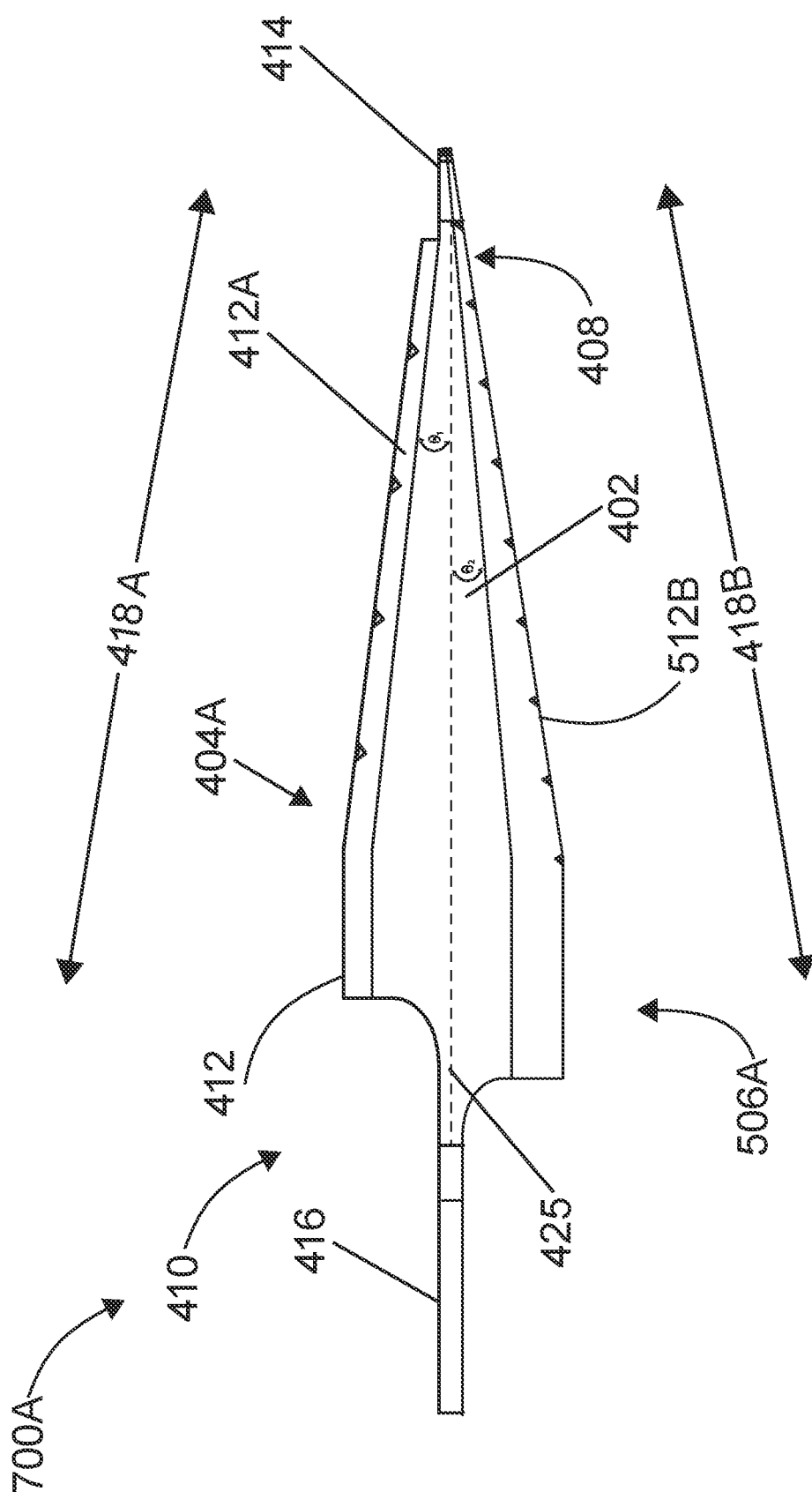

In FIG. 7A, a surgical instrument 700A includes a first surface 404A including one or more columns 422A of cutting blades 412A similar to the various embodiments of the first surface 404A discussed herein. In addition, the surgical instrument 700A includes a second surface 506A including one or more columns 522B (and/or sets of columns 522E and 522F) of cutting blades 512B similar to the various embodiments of the second surface 506A discussed herein.

In FIG. 7B, a surgical instrument 700B includes a first surface 404A including one or more columns 422A of cutting blades 412A similar to the various embodiments of the first surface 404A discussed herein. In addition, the surgical instrument 700B includes a second surface 506B including one or more columns 522B (and/or sets of columns 522E and 522F) of cutting blades 512B similar to the various embodiments of the second surface 506B discussed herein.

Figure 7C:
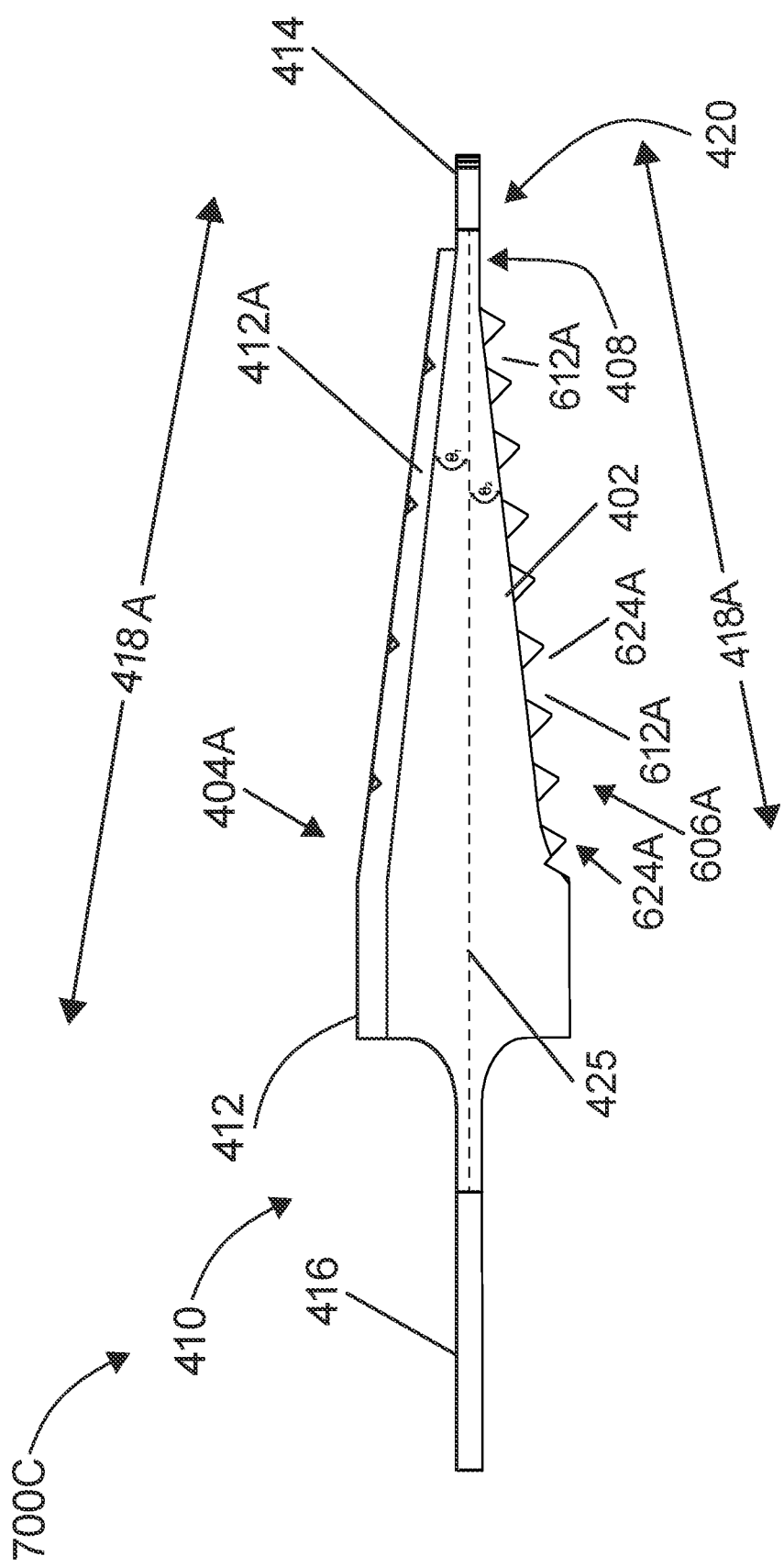

In FIG. 7C, a surgical instrument 700C includes a first surface 404A including one or more columns 422A of cutting blades 412A similar to the various embodiments of the first surface 404A discussed herein. In addition, the surgical instrument 700C includes a second surface 606A including one or more rows 624B of cutting blades 612B similar to the various embodiments of the second surface 606A discussed herein.

Figure 7D:
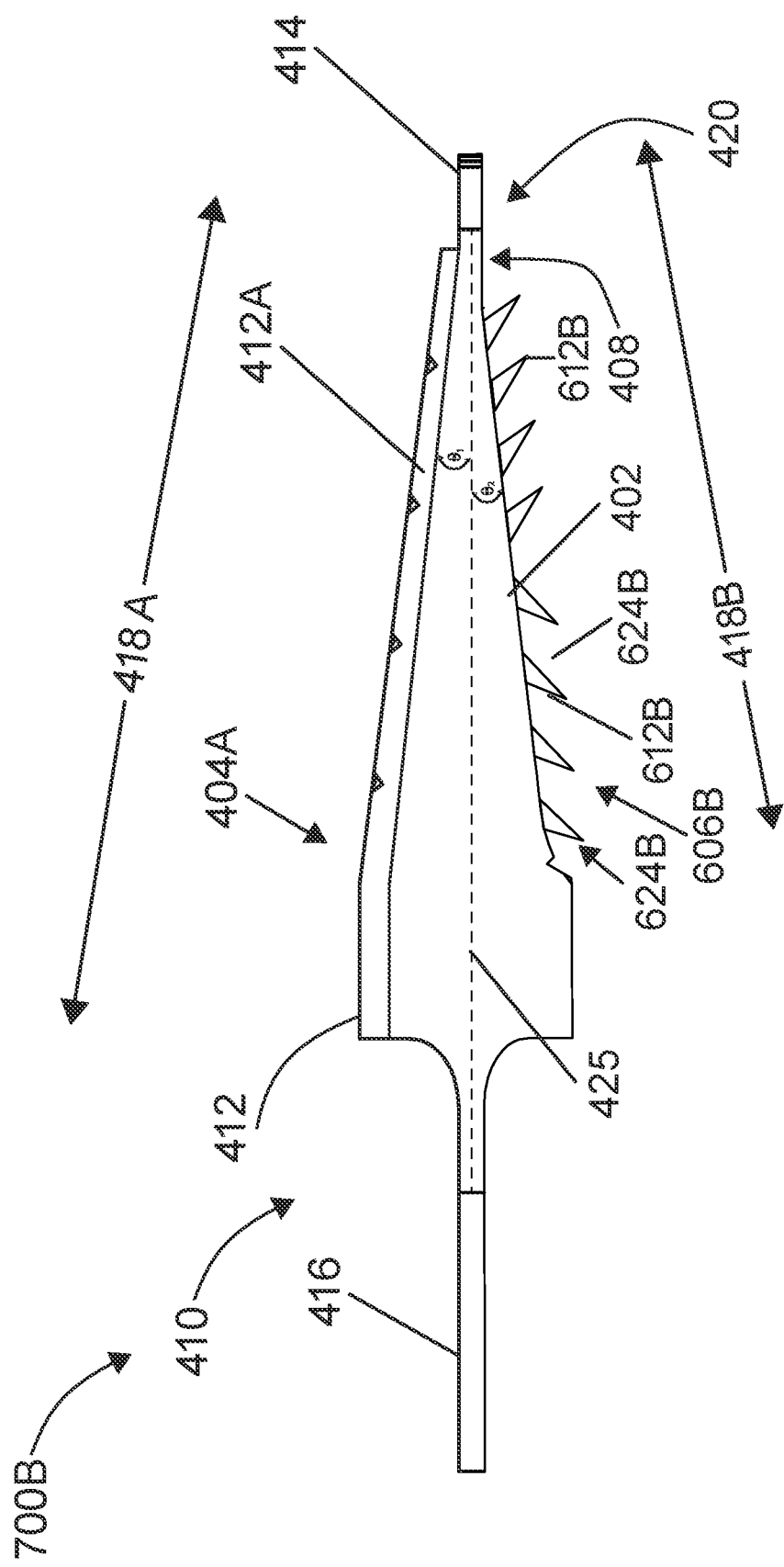

In FIG. 7D, a surgical instrument 700D includes a first surface 404A including one or more columns 422A of cutting blades 412A similar to the various embodiments of the first surface 404A discussed herein. In addition, the surgical instrument 700D includes a second surface 606B including one or more columns 624B of cutting blades 612B similar to the various embodiments of the second surface 606B discussed herein.

FIGS. 8A through 8D are diagrams of various embodiments of a surgical instrument 800. In the various embodiments illustrated in FIGS. 8A through 8D, the surgical instrument 800 includes among other features, a body 402, a distal end 408, a proximal end 410, a set of cutting teeth 414, an attachment mechanism 416, and a cutting tip 420 similar to the body 402, distal end 408, proximal end 410, the set of cutting teeth 414, attachment mechanism 416, and cutting tip 420 of the various embodiments of the surgical instrument 400 discussed herein with reference to FIGS. 4A through 4F.

Figure 8A:
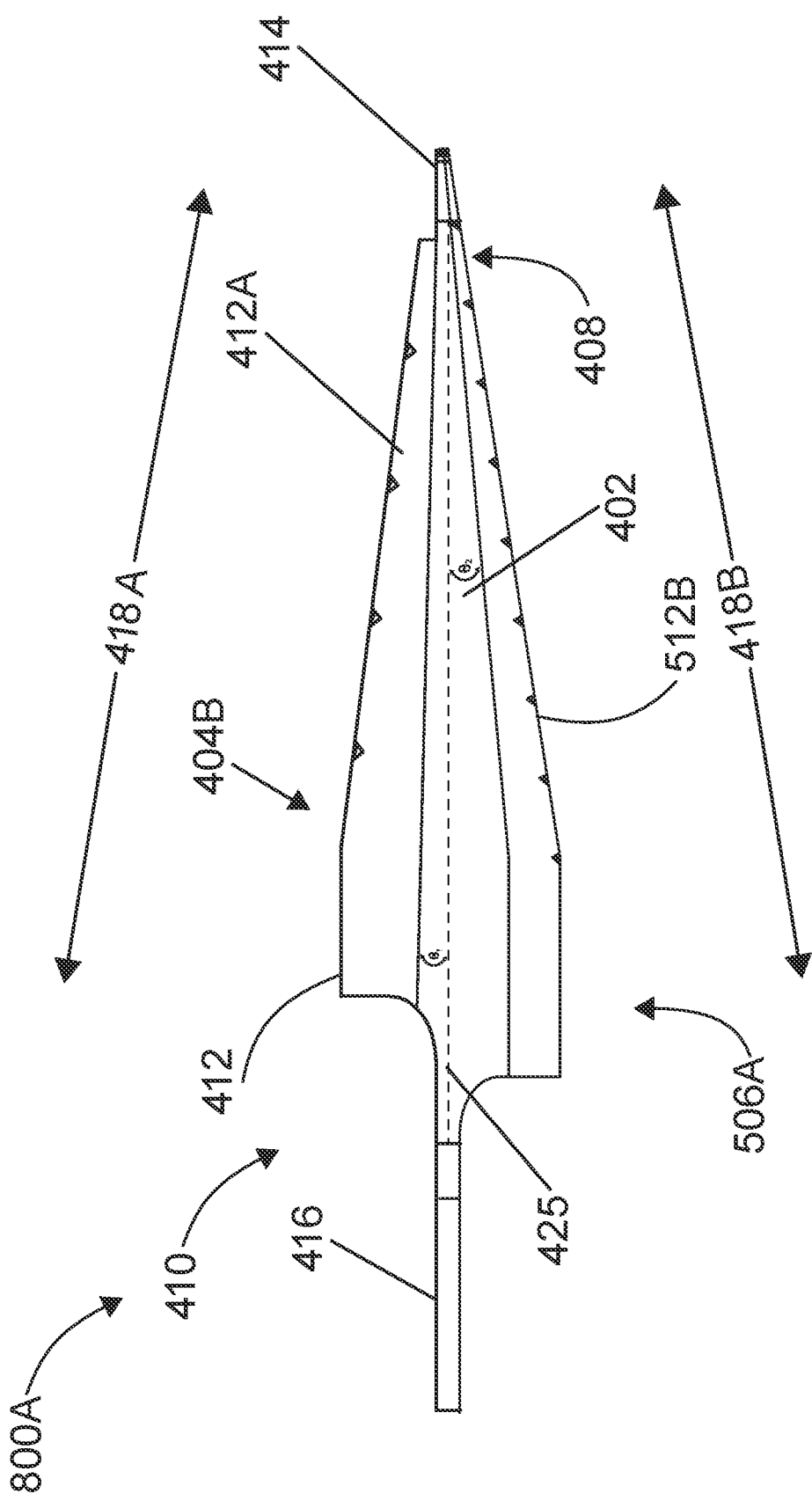
FIGS. 8A through 8D are schematic diagram illustrating various other embodiments of a double-sided surgical instrument including multiple rows of cutting blades and multiple columns of cutting blades.

In FIG. 8A, a surgical instrument 800A includes a first surface 404B including one or more columns 422A of cutting blades 412A similar to the various embodiments of the first surface 404B discussed herein. In addition, the surgical instrument 800A includes a second surface 506A including one or more columns 522B (and/or sets of columns 522E and 522F) of cutting blades 512B similar to the various embodiments of the second surface 506A discussed herein.

Figure 8B:
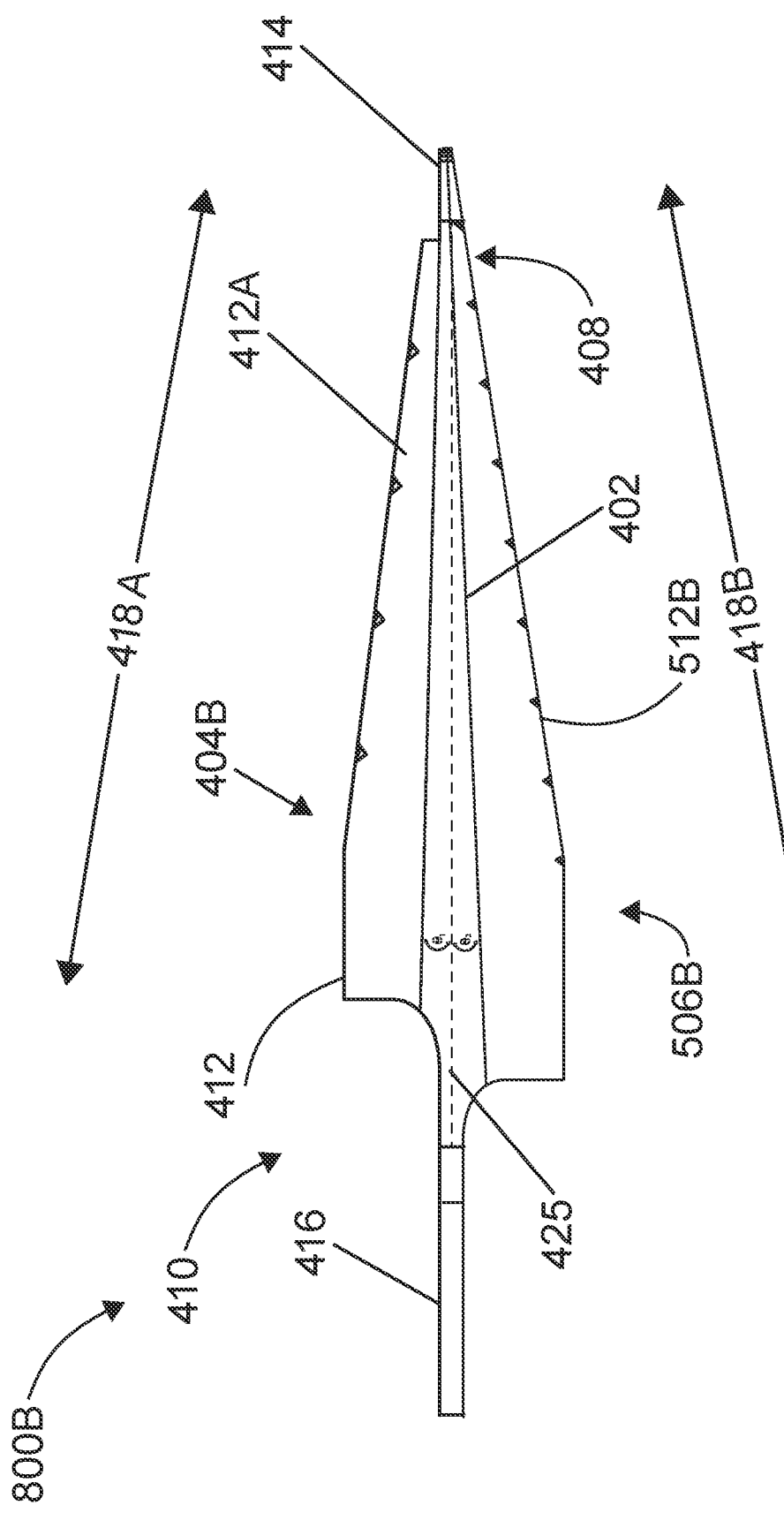

In FIG. 8B, a surgical instrument 800B includes a first surface 404B including one or more columns 422A of cutting blades 412A similar to the various embodiments of the first surface 404B discussed herein. In addition, the surgical instrument 800B includes a second surface 506B including one or more columns 522B (and/or sets of columns 522E and 522F) of cutting blades 512B similar to the various embodiments of the second surface 506B discussed herein.

Figure 8C:
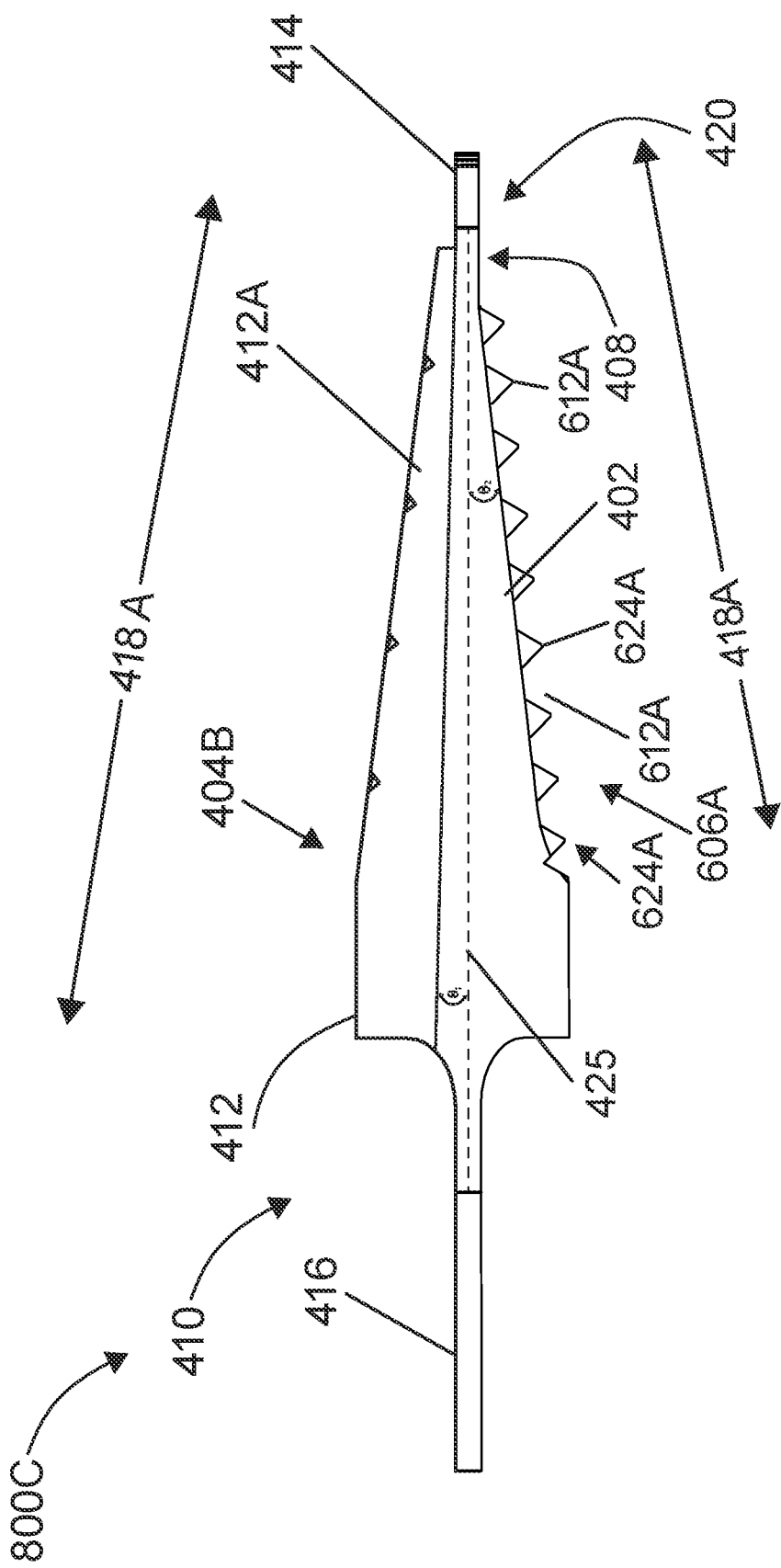

In FIG. 8C, a surgical instrument 800C includes a first surface 404B including one or more columns 422A of cutting blades 412A similar to the various embodiments of the first surface 404B discussed herein. In addition, the surgical instrument 800C includes a second surface 606A including one or more rows 624B of cutting blades 612B similar to the various embodiments of the second surface 606A discussed herein.

Figure 8D:
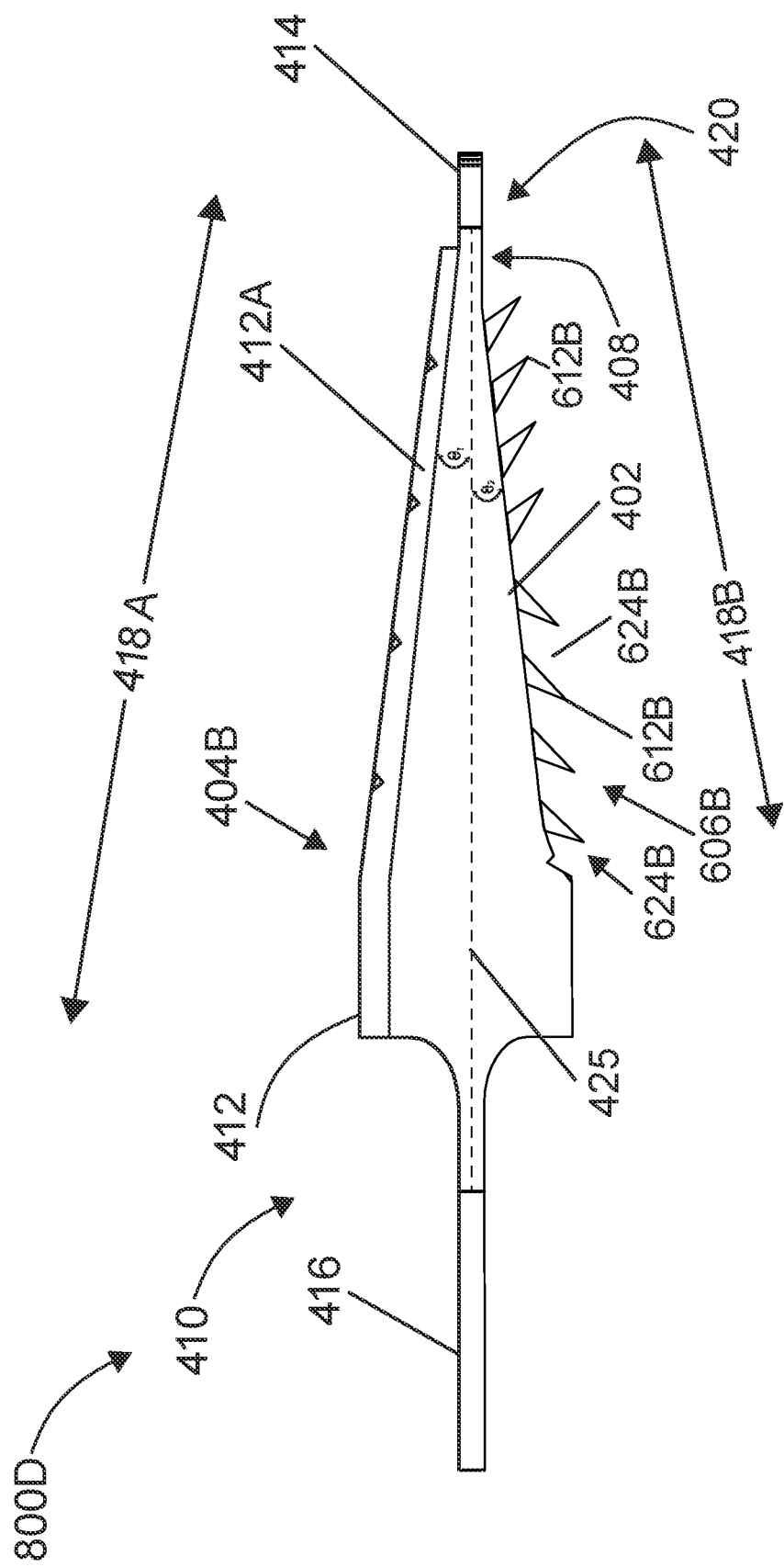

In FIG. 8D, a surgical instrument 800D includes a first surface 404B including one or more columns 422A of cutting blades 412A similar to the various embodiments of the first surface 404B discussed herein. In addition, the surgical instrument 800D includes a second surface 606B including one or more columns 624B of cutting blades 612B similar to the various embodiments of the second surface 606B discussed herein.

Figure 9A:
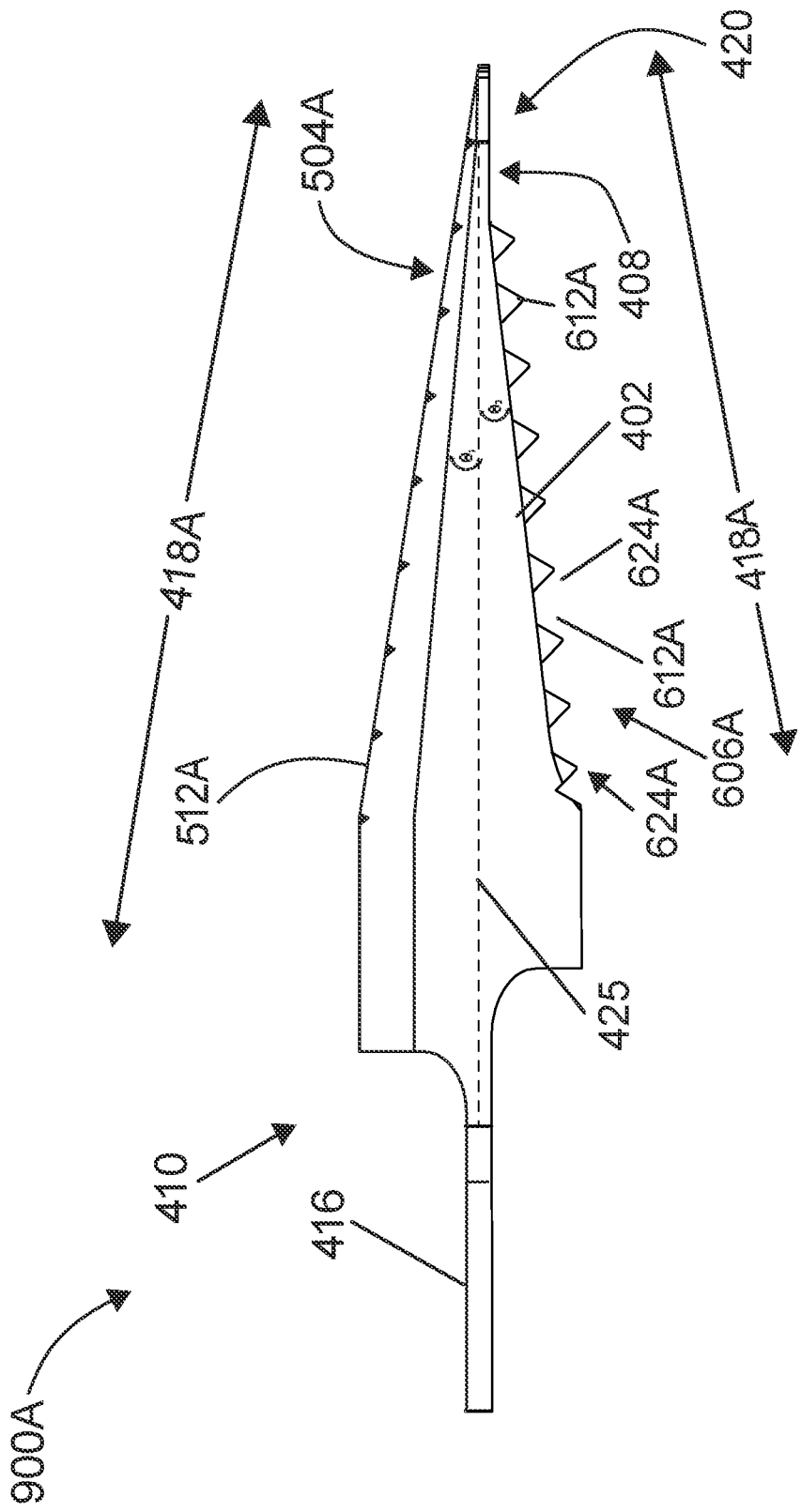
FIGS. 9A and 9B are schematic diagram illustrating various further embodiments of a double-sided surgical instrument including multiple rows of cutting blades and multiple columns of cutting blades.
Figure 9B:
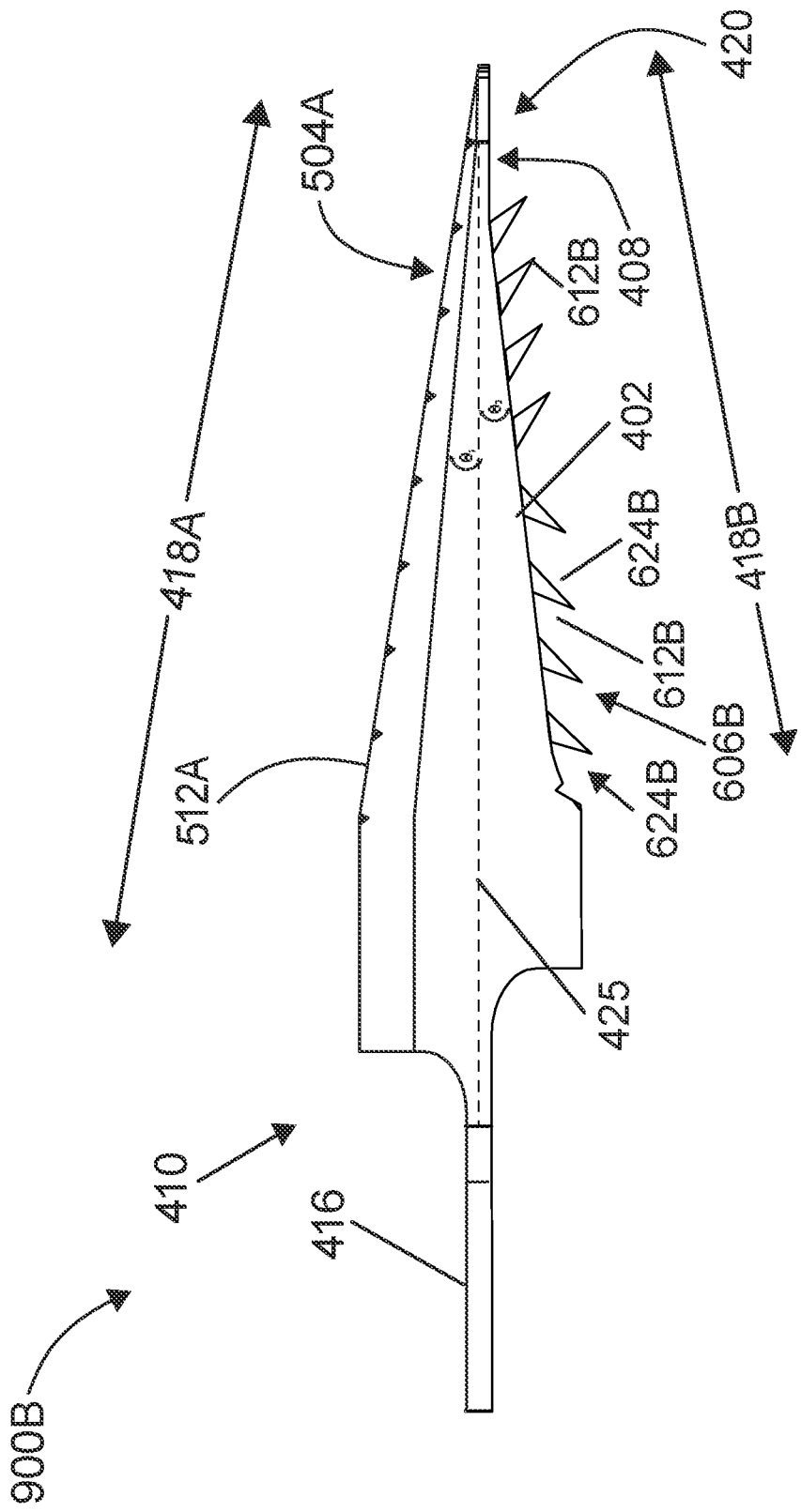

FIGS. 9A and 9B are diagrams of various embodiments of a surgical instrument 900. In the various embodiments illustrated in FIGS. 9A and 9B, the surgical instrument 900 includes among other features, a body 402, a distal end 408, a proximal end 410, a set of cutting teeth 414, an attachment mechanism 416, and a cutting tip 420 similar to the body 402, distal end 408, proximal end 410, the set of cutting teeth 414, attachment mechanism 416, and cutting tip 420 of the various embodiments of the surgical instrument 400 discussed herein with reference to FIGS. 4A through 4F.

In FIG. 9A, a surgical instrument 900A includes a first surface 504A including one or more columns 522A (and/or sets of columns 522C and 522D) of cutting blades 512A similar to the various embodiments of the first surface 504A discussed herein. In addition, the surgical instrument 900A includes a second surface 606A including one or more rows 624B of cutting blades 612B similar to the various embodiments of the second surface 606A discussed herein.

In FIG. 9B, a surgical instrument 900B includes a first surface 504A including one or more columns 522A (and/or sets of columns 522C and 522D) of cutting blades 512A similar to the various embodiments of the first surface 504A discussed herein. In addition, the surgical instrument 900B includes a second surface 606B including one or more columns 624B of cutting blades 612B similar to the various embodiments of the second surface 606B discussed herein.

Figure 10A:
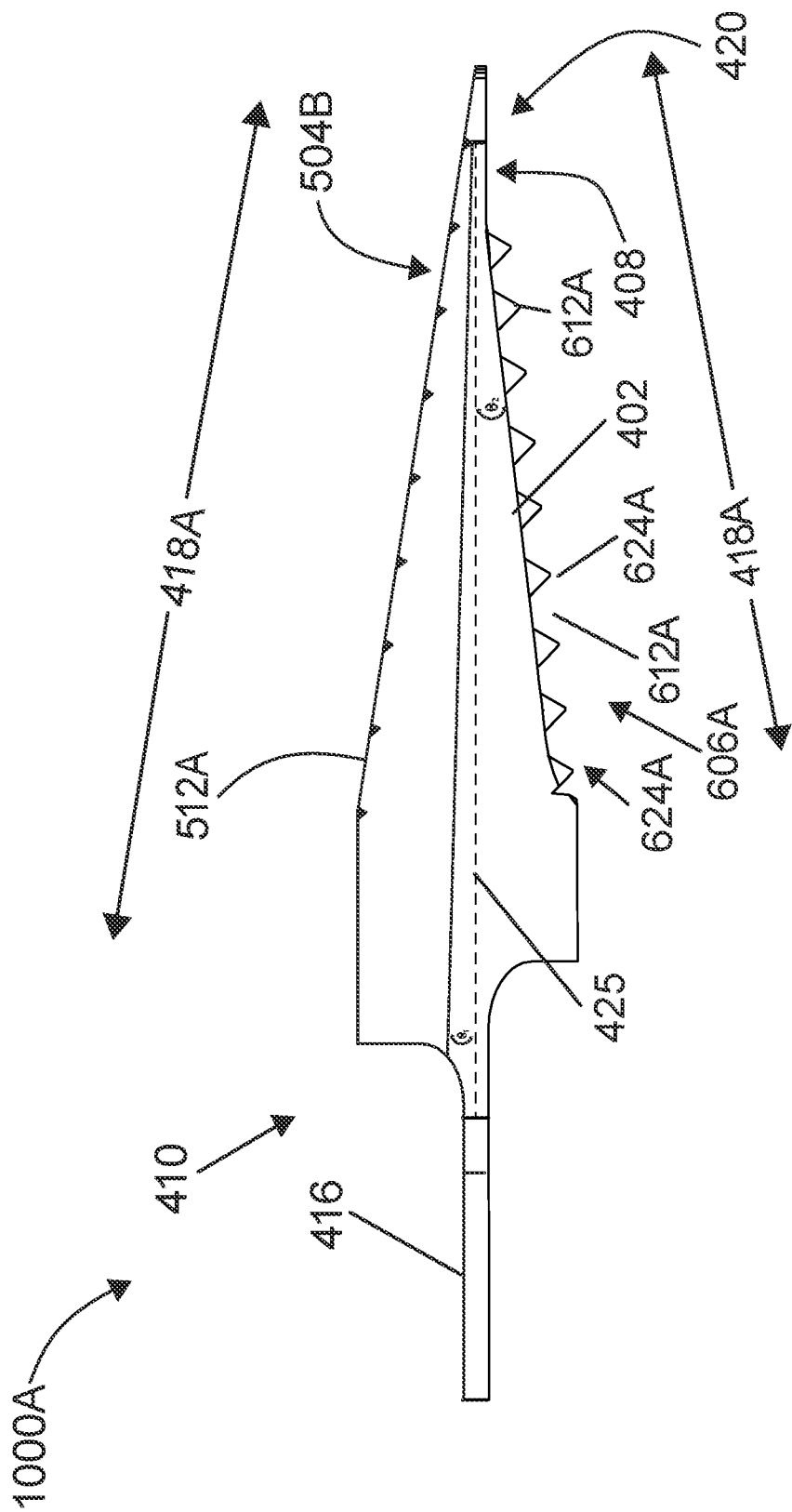
FIGS. 10A and 10B are schematic diagram illustrating various additional embodiments of a double-sided surgical instrument including multiple rows of cutting blades and multiple columns of cutting blades.
Figure 10B:
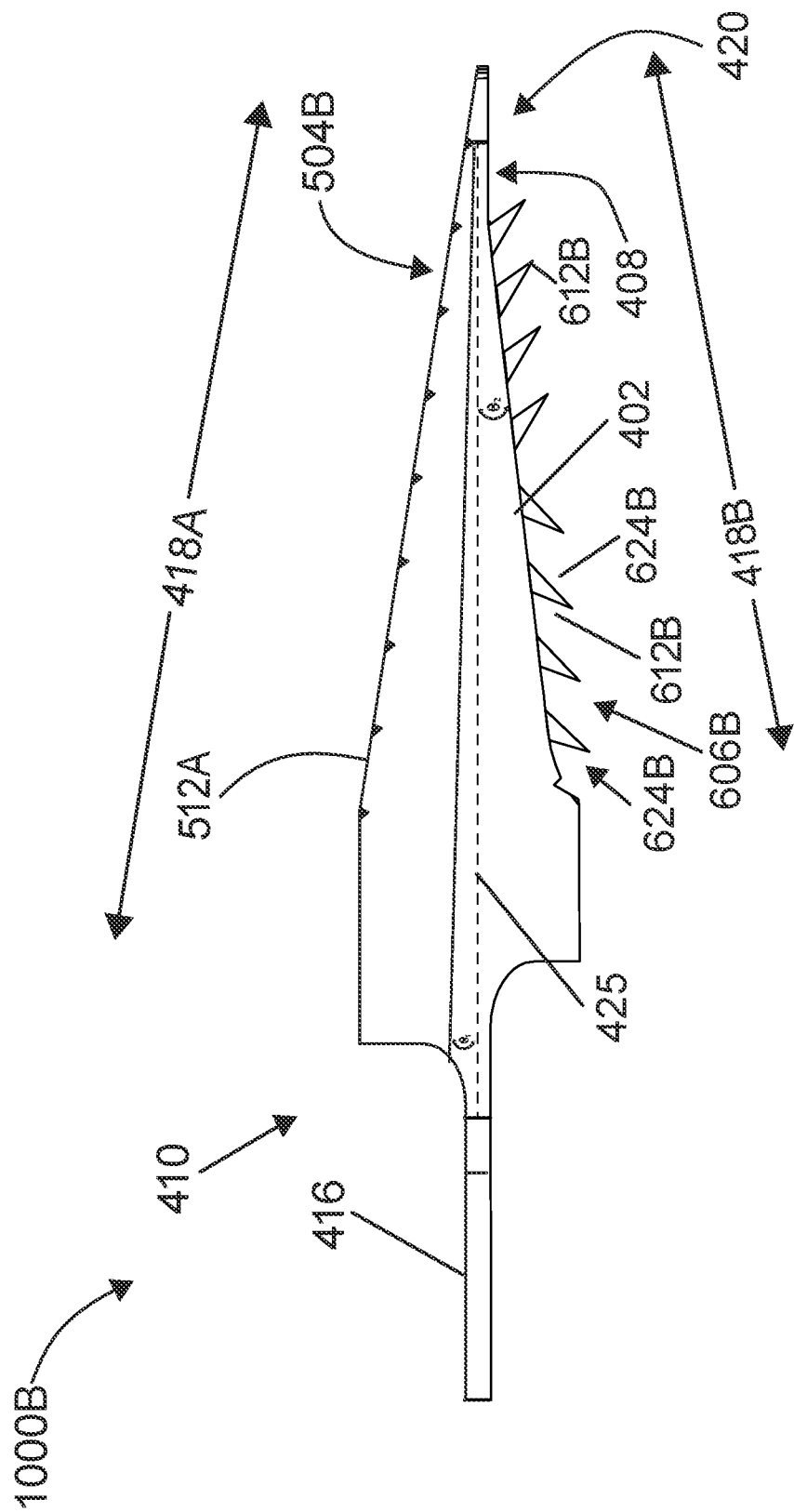

FIGS. 10A and 10B are diagrams of various embodiments of a surgical instrument 1000. In the various embodiments illustrated in FIGS. 10A and 10B, the surgical instrument 1000 includes among other features, a body 402, a distal end 408, a proximal end 410, a set of cutting teeth 414, an attachment mechanism 416, and a cutting tip 420 similar to the body 402, distal end 408, proximal end 410, the set of cutting teeth 414, attachment mechanism 416, and cutting tip 420 of the various embodiments of the surgical instrument 400 discussed herein with reference to FIGS. 4A through 4F.

In FIG. 10A, a surgical instrument 1000A includes a first surface 504B including one or more columns 522A (and/or sets of columns 522C and 522D) of cutting blades 512A similar to the various embodiments of the first surface 504B discussed herein. In addition, the surgical instrument 1000A includes a second surface 606A including one or more rows 624B of cutting blades 612B similar to the various embodiments of the second surface 606A discussed herein.

In FIG. 10B, a surgical instrument 1000B includes a first surface 504B including one or more columns 522A (and/or sets of columns 522C and 522D) of cutting blades 512A similar to the various embodiments of the first surface 504B discussed herein. In addition, the surgical instrument 1000B includes a second surface 606B including one or more columns 624B of cutting blades 612B similar to the various embodiments of the second surface 606B discussed herein.

In various embodiments, the surgical instruments 400 through 1000 each form at least a portion of a cutting blade and/or cutting device. In some embodiments, the surgical instruments 400 through 1000 form at least a portion of a sagittal blade and/or sagittal saw, among other cutting blades and/or cutting devices that are possible and contemplated herein.

In various embodiments, the surgical instruments 400 through 1000 can each be utilized to perform an osteotomy, which can include any suitable osteotomy that is known or developed in the future. In some embodiments, the osteotomy performed by the surgical instruments 400 through 1000 includes cutting and/or preparing a single bone (e.g., a cuneiform, a metatarsal, calcaneus, metacarpal, humerus, and femur, etc.)

In additional or alternative embodiments, the surgical instruments 400 through 1000 can each be utilized to perform two or more osteotomies. In certain embodiments, the surgical instruments 400 through 1000 can each be utilized to simultaneously perform two or more osteotomies, which can include cutting two different bones at the same time (e.g., a cuneiform and a metatarsal, carpal and metacarpal, and humerus and scapula, etc.).

In one non-limiting example, a first bone may be cut/prepared with one side of a surgical instrument 400 through 1000 and a second bone may be cut/prepared with another or different side of the surgical instrument 400 through 1000. Here, the first and second bones may be cut/prepared in series (e.g., one at a time), cut/prepared in parallel (e.g., at the same time or simultaneously), and/or cut/prepared substantially in parallel and/or series.

In another non-limiting example, a first portion of a bone may be cut/prepared with one side of the surgical instrument 400 through 1000 and a second or different portion of the same bone may be cut/prepared with another or different side of the surgical instrument 400 through 1000. Here, the first and second bones may be cut/prepared in series (e.g., one at a time), cut/prepared in parallel (e.g., at the same time or simultaneously), and/or cut/prepared substantially in parallel and/or series.

In still another non-limiting example, a first bone and a second bone may be cut/prepared with the same side of the surgical instrument 400 through 1000. Here, the first and second bones may be cut/prepared in series (e.g., one at a time), cut/prepared in parallel (e.g., at the same time or simultaneously), and/or cut/prepared substantially in parallel and/or series.

In yet another non-limiting example, a first portion and a second portion of the same bone may be cut/prepared with the same side of the surgical instrument 400 through 1000. Here, the first and second bones may be cut/prepared in series (e.g., one at a time), cut/prepared in parallel (e.g., at the same time or simultaneously), and/or cut/prepared substantially in parallel and/or series.

In a further non-limiting example, the same portion of the same bone may be cut with different sides of the surgical instrument 400 through 1000. Here, the first and second bones may be cut/prepared in series (e.g., one at a time), cut/prepared in parallel (e.g., at the same time or simultaneously), and/or cut/prepared substantially in parallel and/or substantially in series.

In various embodiments, at least one of the two or more osteotomies capable of being performed by a surgical instrument 400 through 1000 includes a wedge-shaped osteotomy and at least one of the two or more osteotomies includes a straight-cut osteotomy or a parallel-cut osteotomy, among other types of osteotomies and/or combinations of osteotomies that are possible and contemplated herein. In other embodiments, at least one of the two or more osteotomies capable of being performed by the surgical instrument 400 through 1000 includes a straight-cut osteotomy and at least one of the two or more osteotomies includes a wedge-cut osteotomy or a parallel-cut osteotomy, among other types of osteotomies and/or combinations of osteotomies that are possible and contemplated herein. In still other embodiments, at least one of the two or more osteotomies capable of being performed by the surgical instrument 400 through 1000 includes a parallel-cut osteotomy and at least one of the two or more osteotomies includes a wedge-cut osteotomy or a straight-cut osteotomy, among other types of osteotomies and/or combinations of osteotomies that are possible and contemplated herein.

In some embodiments, a surgical instrument 400 through 1000 (e.g., via first surface and second surface) can perform and/or facilitate performance of a relatively large or larger wedge-shaped osteotomy between two bones (e.g., at a joint) and/or the first surface can perform and/or facilitate performance of a relatively small or smaller wedge-shaped osteotomy on a first bone and the second surface can perform and/or facilitate performance of another relatively small or smaller wedge-shaped osteotomy on a second bone, which can include the same size or a different size wedge-shaped osteotomy than the first surface. In other embodiments, the surgical instrument 400 through 1000 (e.g., via first surface and second surface) can perform and/or facilitate performance of a relatively large or larger straight-cut osteotomy between two bones (e.g., at a joint) and/or the first surface can perform and/or facilitate performance of a relatively small or smaller straight-cut osteotomy on a first bone and the second surface can perform and/or facilitate performance of another relatively small or smaller straight-cut osteotomy on a second bone, which can include the same size or a different size straight-cut osteotomy than the first surface. In other embodiments, the surgical instrument 400 through 1000 (e.g., via first surface and second surface) can perform and/or facilitate performance of a relatively large or larger parallel-cut osteotomy between two bones (e.g., at a joint) and/or the first surface can perform and/or facilitate performance of a relatively small or smaller parallel-cut osteotomy on a first bone and the second surface can perform and/or facilitate performance of another relatively small or smaller parallel-cut osteotomy on a second bone, which can include the same size or a different size parallel-cut osteotomy than the first surface.

Figure 11:
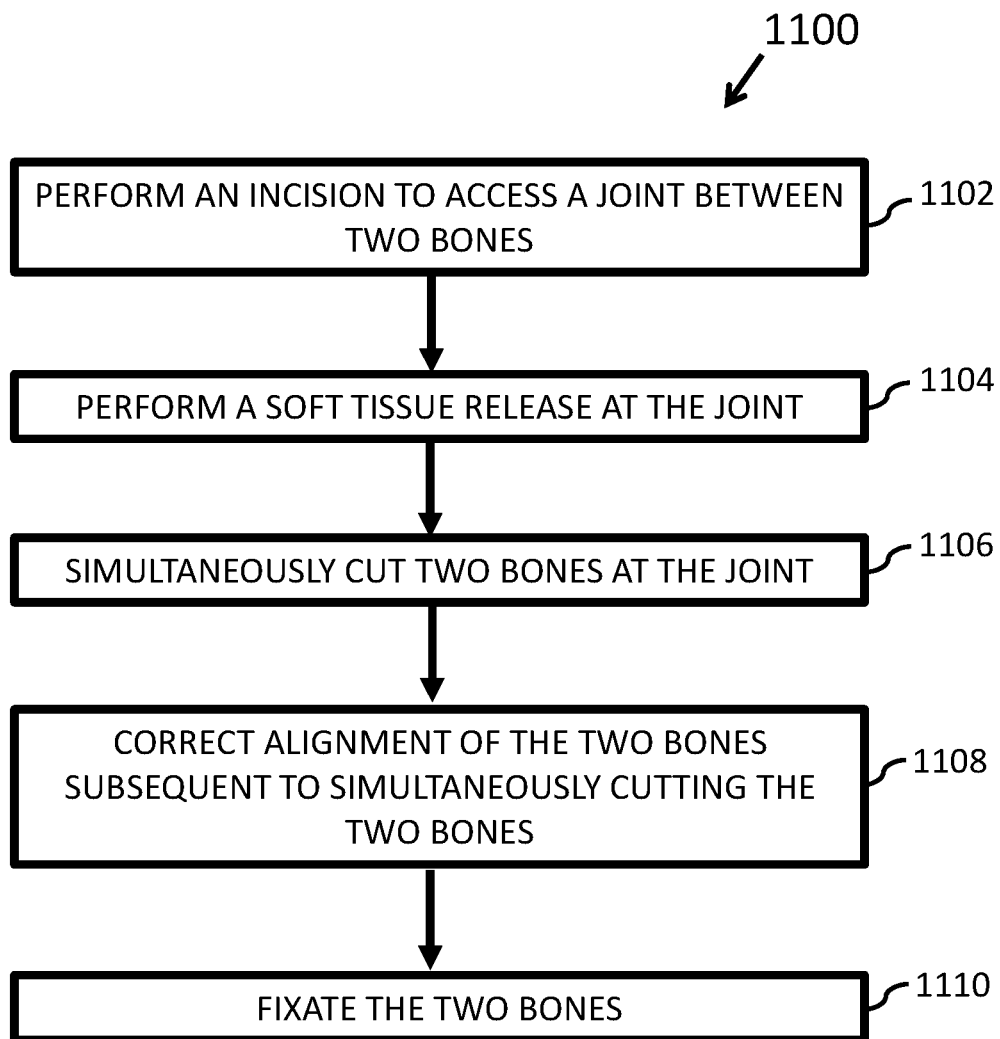
FIGS. 11 through 14 are schematic flow diagrams of various embodiments of a method for aligning two bones connected at a joint.

FIG. 11 is a schematic flow chart diagram illustrating one embodiment of a method 1100 for aligning two bones connected at a joint. The two bones may be any two bones separated by any joint (e.g., in a human or animal).

At least in the illustrated embodiment, the method 1100 begins by performing an incision in a patient to open and/or access a target joint (block 1102). The target joint may include any suitable joint between any two bones. Further, the incision may be performed at any suitable location at the target joint and/or bone(s) that can enable access the target joint.

A soft tissue release is performed at the joint (block 1104). The soft tissue release may include any suitable technique and/or procedure that can release the target joint and/or one or both of the bones at the target joint.

Two bones at the target joint are simultaneously cut and/or prepared (block 1106). The two bones may be simultaneously cut using a double-sided surgical instrument. In some embodiments, simultaneously cutting the two bones at the target joint with the double-sided surgical instrument includes simultaneously cutting the two bones at the target joint with one or more embodiments of a surgical instrument 400. In other embodiments, simultaneously cutting the two bones at the target joint with the double-sided surgical instrument includes simultaneously cutting the two bones at the target joint with one or more embodiments of a surgical instrument 500. In still other embodiments, simultaneously cutting the two bones at the target joint with the double-sided surgical instrument includes simultaneously cutting the two bones at the target joint with one or more embodiments of a surgical instrument 600. In further embodiments, simultaneously cutting the two bones at the target joint with the double-sided surgical instrument includes simultaneously cutting the two bones at the target joint with one or more embodiments of a surgical instrument 700. In yet further embodiments, simultaneously cutting the two bones at the target joint with the double-sided surgical instrument includes simultaneously cutting the two bones at the target joint with one or more embodiments of a surgical instrument 800. In still further embodiments, simultaneously cutting the two bones at the target joint with the double-sided surgical instrument includes simultaneously cutting the two bones at the target joint with one or more embodiments of a surgical instrument 900. In additional embodiments, simultaneously cutting the two bones at the target joint with the double-sided surgical instrument includes simultaneously cutting the two bones at the target joint with one or more embodiments of a surgical instrument 1000.

The alignment of the two bones is corrected subsequent to simultaneously cutting the two bones at the target joint (block 1108). Correcting the alignment of the two bones includes, in various embodiments, correcting the alignment of the two bones in one plane, two planes, or three planes, which can include a transverse plane, a sagittal plane, and/or a frontal plane.

After correction of the alignment, the two bones are fixated (block 1110). The bones may be fixated using any fixation technique(s) and/or fixation device(s) that is/are known or developed in the future. In various embodiments, the two bones are fixated using a fixation device manufactured by Fusion Orthopedics, LLC of Mesa, Arizona.

Figure 12:
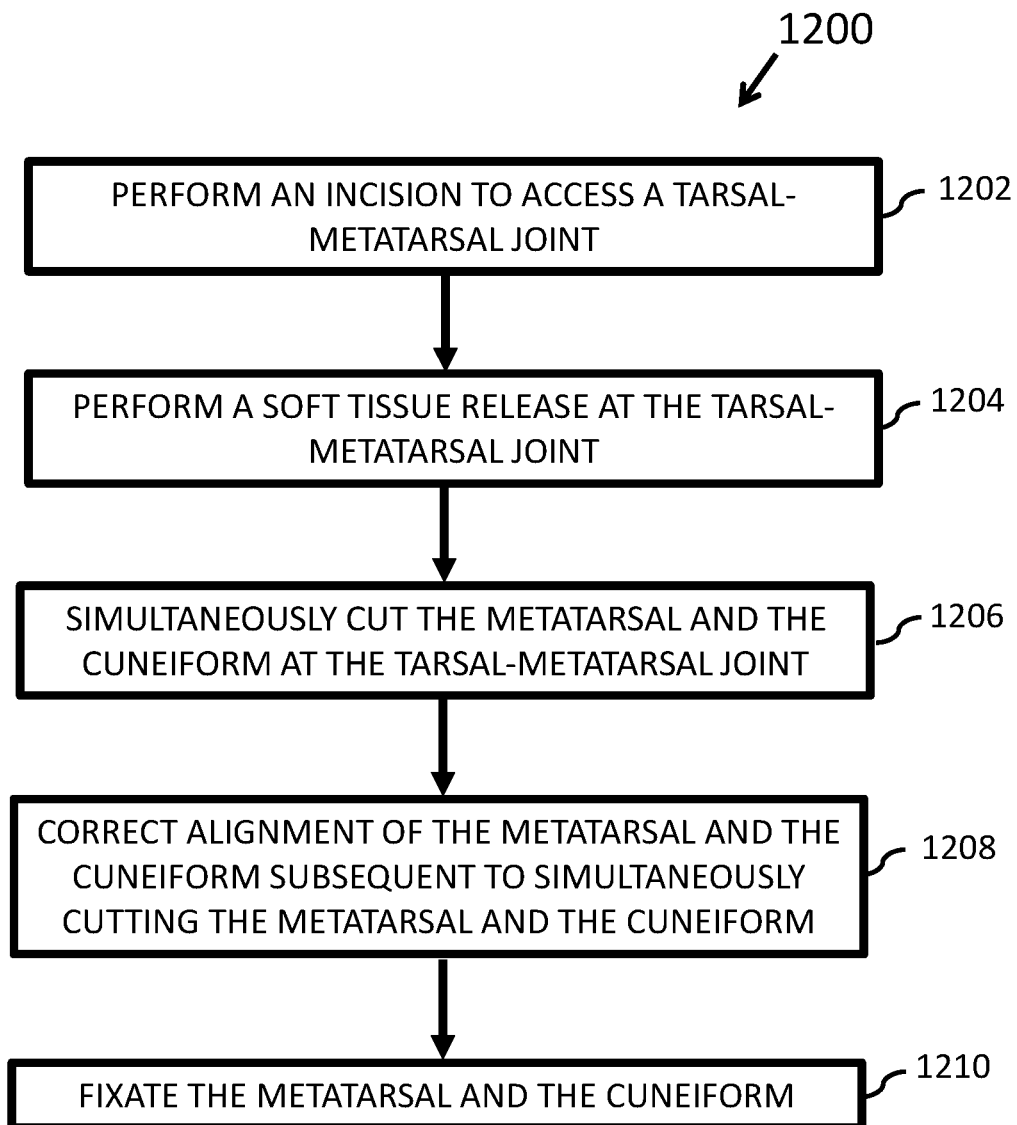

FIG. 12 is a schematic flow chart diagram illustrating another embodiment of a method 1200 for aligning two bones connected at a joint. In various embodiments, the joint includes a tarsal-metatarsal joint and the two bones include a metatarsal and a cuneiform. In certain embodiments, the metatarsal includes the first metatarsal and cuneiform. Further, the method 1200 may be utilized to correct a bunion. That is, the method 1200 can include a bunionectomy.

At least in the illustrated embodiment, the method 1200 begins by performing an incision in a patient to open and/or access a tarsal-metatarsal joint (block 1202). The incision may be performed at any suitable location on and/or at the tarsal-metatarsal joint, metatarsal, and/or cuneiform. In various embodiments, the incision can be performed on the top and/or side of the metatarsal (e.g., the first metatarsal).

A soft tissue release is performed at the tarsal-metatarsal joint (block 1204). The soft tissue release may include any suitable technique and/or procedure that can release soft tissue at the tarsal-metatarsal joint. In some embodiments, the soft tissue release includes a lateral release of soft tissue.

The metatarsal and cuneiform at the tarsal-metatarsal joint are simultaneously cut and/or prepared (block 1206). The metatarsal and the cuneiform may be simultaneously cut using a double-sided surgical instrument. In some embodiments, simultaneously cutting the metatarsal and the cuneiform with the double-sided surgical instrument includes simultaneously cutting the metatarsal and the cuneiform with one or more embodiments of a surgical instrument 400. In other embodiments, simultaneously cutting the metatarsal and the cuneiform with the double-sided surgical instrument includes simultaneously cutting the metatarsal and the cuneiform with one or more embodiments of a surgical instrument 500. In still other embodiments, simultaneously cutting the metatarsal and the cuneiform with the double-sided surgical instrument includes simultaneously cutting the metatarsal and the cuneiform with one or more embodiments of a surgical instrument 600. In further embodiments, simultaneously cutting the metatarsal and the cuneiform with the double-sided surgical instrument includes simultaneously cutting the metatarsal and the cuneiform with one or more embodiments of a surgical instrument 700. In yet further embodiments, simultaneously cutting the metatarsal and the cuneiform with the double-sided surgical instrument includes simultaneously cutting the metatarsal and the cuneiform with one or more embodiments of a surgical instrument 800. In still further embodiments, simultaneously cutting the metatarsal and the cuneiform with the double-sided surgical instrument includes simultaneously cutting the metatarsal and the cuneiform with one or more embodiments of a surgical instrument 900. In additional embodiments, simultaneously cutting the metatarsal and the cuneiform with the double-sided surgical instrument includes simultaneously cutting the metatarsal and the cuneiform with one or more embodiments of a surgical instrument 1000.

The alignment of the metatarsal and the cuneiform is corrected subsequent to simultaneously cutting the metatarsal and the cuneiform (block 1208). Correcting the alignment of the metatarsal and the cuneiform includes, in various embodiments, correcting the alignment of the metatarsal and the cuneiform in one plane, two planes, or three planes, which can include a transverse plane, a sagittal plane, and/or a frontal plane.

After correction of the alignment, the metatarsal and the cuneiform are fixated to one another (block 1210). The metatarsal and the cuneiform may be fixated using any fixation technique(s) and/or fixation device(s) that is/are known or developed in the future. In various embodiments, the metatarsal and the cuneiform are fixated using a fixation device manufactured by Fusion Orthopedics, LLC of Mesa, Arizona.

Figure 13:
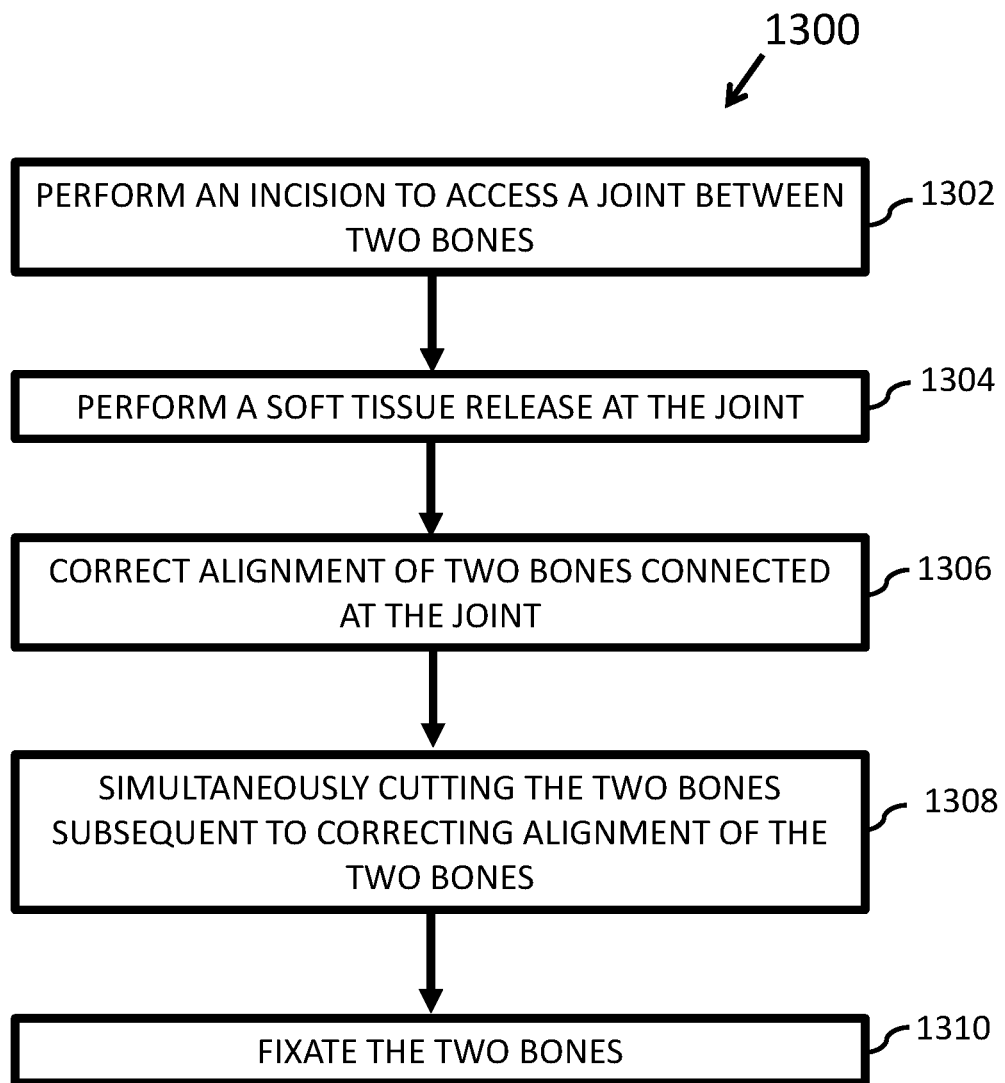

FIG. 13 is a schematic flow chart diagram illustrating yet another embodiment of a method 1300 for aligning two bones connected at a joint. The two bones may be any two bones separated by any joint (e.g., in a human or animal).

At least in the illustrated embodiment, the method 1300 begins by performing an incision in a patient to open and/or access a target joint (block 1302). The target joint may include any suitable joint between any two bones. Further, the incision may be performed at any suitable location at the target joint and/or bone(s) that can enable access the target joint.

A soft tissue release is performed at the joint (block 1304). The soft tissue release may include any suitable technique and/or procedure that can release the target joint and/or one or both of the bones at the target joint.

The alignment of two bones at the target joint is corrected (block 1306). Correcting the alignment of the two bones includes, in various embodiments, correcting the alignment of the two bones in one plane, two planes, or three planes, which can include a transverse plane, a sagittal plane, and/or a frontal plane.

Subsequent to correcting the alignment, the two bones are simultaneously cut and/or prepared (block 1308). The two bones may be simultaneously cut using a double-sided surgical instrument. In some embodiments, simultaneously cutting the two bones at the target joint with the double-sided surgical instrument includes simultaneously cutting the two bones at the target joint with one or more embodiments of a surgical instrument 400. In other embodiments, simultaneously cutting the two bones at the target joint with the double-sided surgical instrument includes simultaneously cutting the two bones at the target joint with one or more embodiments of a surgical instrument 500. In still other embodiments, simultaneously cutting the two bones at the target joint with the double-sided surgical instrument includes simultaneously cutting the two bones at the target joint with one or more embodiments of a surgical instrument 600. In further embodiments, simultaneously cutting the two bones at the target joint with the double-sided surgical instrument includes simultaneously cutting the two bones at the target joint with one or more embodiments of a surgical instrument 700. In yet further embodiments, simultaneously cutting the two bones at the target joint with the double-sided surgical instrument includes simultaneously cutting the two bones at the target joint with one or more embodiments of a surgical instrument 800. In still further embodiments, simultaneously cutting the two bones at the target joint with the double-sided surgical instrument includes simultaneously cutting the two bones at the target joint with one or more embodiments of a surgical instrument 900. In additional embodiments, simultaneously cutting the two bones at the target joint with the double-sided surgical instrument includes simultaneously cutting the two bones at the target joint with one or more embodiments of a surgical instrument 1000.

After simultaneously cutting the two bones, the two bones are fixated (block 1310). The bones may be fixated using any fixation technique(s) and/or fixation device(s) that is/are known or developed in the future. In various embodiments, the two bones are fixated using a fixation device manufactured by Fusion Orthopedics, LLC of Mesa, Arizona.

Figure 14:
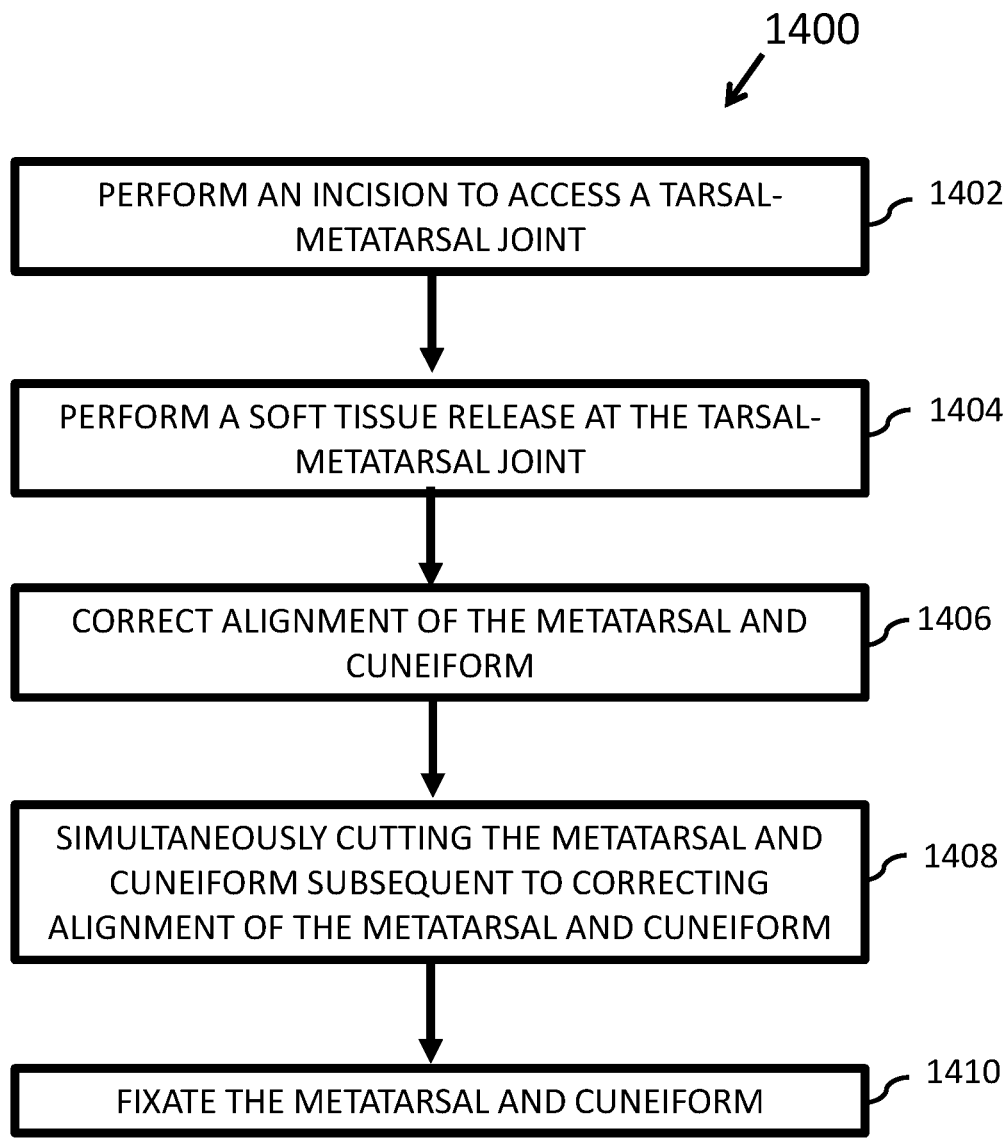

FIG. 14 is a schematic flow chart diagram illustrating still another embodiment of a method 1400 for aligning two bones connected at a joint. In various embodiments, the joint includes a tarsal-metatarsal joint and the two bones include a metatarsal and a cuneiform. In certain embodiments, the metatarsal includes the first metatarsal and cuneiform. Further, the method 1400 may be utilized to correct a bunion. That is, the method 1400 can include a bunionectomy.

At least in the illustrated embodiment, the method 1400 begins by performing an incision in a patient to open and/or access a tarsal-metatarsal joint (block 1402). The incision may be performed at any suitable location on and/or at the tarsal-metatarsal joint, metatarsal, and/or cuneiform. In various embodiments, the incision can be performed on the top and/or side of the metatarsal (e.g., the first metatarsal).

A soft tissue release is performed at the tarsal-metatarsal joint (block 1404). The soft tissue release may include any suitable technique and/or procedure that can release soft tissue at the tarsal-metatarsal joint. In some embodiments, the soft tissue release includes a lateral release of soft tissue.

The alignment of the metatarsal and the cuneiform is corrected (block 1406). Correcting the alignment of the metatarsal and the cuneiform includes, in various embodiments, correcting the alignment of the metatarsal and the cuneiform in one plane, two planes, or three planes, which can include a transverse plane, a sagittal plane, and/or a frontal plane.

Subsequent to correcting the alignment, the metatarsal and cuneiform at the tarsal-metatarsal joint are simultaneously cut and/or prepared (block 1408). The metatarsal and the cuneiform may be simultaneously cut using a double-sided surgical instrument. In some embodiments, simultaneously cutting the metatarsal and the cuneiform with the double-sided surgical instrument includes simultaneously cutting the metatarsal and the cuneiform with one or more embodiments of a surgical instrument 400. In other embodiments, simultaneously cutting the metatarsal and the cuneiform with the double-sided surgical instrument includes simultaneously cutting the metatarsal and the cuneiform with one or more embodiments of a surgical instrument 500. In still other embodiments, simultaneously cutting the metatarsal and the cuneiform with the double-sided surgical instrument includes simultaneously cutting the metatarsal and the cuneiform with one or more embodiments of a surgical instrument 600. In further embodiments, simultaneously cutting the metatarsal and the cuneiform with the double-sided surgical instrument includes simultaneously cutting the metatarsal and the cuneiform with one or more embodiments of a surgical instrument 700. In yet further embodiments, simultaneously cutting the metatarsal and the cuneiform with the double-sided surgical instrument includes simultaneously cutting the metatarsal and the cuneiform with one or more embodiments of a surgical instrument 800. In still further embodiments, simultaneously cutting the metatarsal and the cuneiform with the double-sided surgical instrument includes simultaneously cutting the metatarsal and the cuneiform with one or more embodiments of a surgical instrument 900. In additional embodiments, simultaneously cutting the metatarsal and the cuneiform with the double-sided surgical instrument includes simultaneously cutting the metatarsal and the cuneiform with one or more embodiments of a surgical instrument 1000.

After simultaneously cutting the metatarsal and the cuneiform, the metatarsal and the cuneiform are fixated to one another (block 1410). The metatarsal and the cuneiform may be fixated using any fixation technique(s) and/or fixation device(s) that is/are known or developed in the future. In various embodiments, the metatarsal and the cuneiform are fixated using a fixation device manufactured by Fusion Orthopedics, LLC of Mesa, Arizona.

The various embodiments discussed herein may be practiced in other specific forms and the described embodiments are to be considered in all respects only as illustrative, and not restrictive. The scope of the technology is, therefore, indicated by the appended claims rather than by the foregoing description. All changes that come within the meaning and range of equivalency of the claims are to be embraced within their scope. That is, one of ordinary skill in the art will appreciate that modifications and/or adaptations to the various aspects may be made without departing from the scope of the present technology, as set forth in the following claims.

The invention claimed is:

1. A surgical instrument, comprising:
a single solid body comprising a distal end, a proximal end, a bottom surface, a top surface, and a reference plane between the bottom surface and the top surface;
wherein:
the top surface includes a top slope that extends away from the reference plane at a first angle; and
the bottom surface includes a bottom slope that extends away from the reference plane at a second angle;
a first plurality of columns of cutting blades spaced apart and positioned on the top surface, wherein each column of the first plurality of columns of cutting blades comprises a single cutting blade, wherein the cutting blade:
extends away from the top surface, and
extends along the top surface from the distal end to the proximal end;
a second plurality of columns of cutting blades spaced apart and positioned on the bottom surface, wherein each column of the second plurality of cutting blades comprises a single cutting blade, wherein the cutting blade:
extends away from the bottom surface,
extends along the bottom surface from the distal end to the proximal end.

2. The surgical instrument of claim 1, wherein:
each cutting blade in the first plurality of cutting blades comprises a first height, wherein
the first height is uniform from the proximal end to the distal end.

3. The surgical instrument of claim 2, wherein the first angle is zero degrees.

4. The surgical instrument of claim 3, wherein the second angle is zero degrees.

5. The surgical instrument of claim 4, wherein:
each cutting blade in the second plurality of cutting blades comprises a second height,
wherein the second height is uniform from the proximal end to the distal end.

6. The surgical instrument of claim 4, wherein:
each cutting blade in the second plurality of cutting blades comprises a third gradually increasing height extending from the distal end to the proximal end such that a fourth height at the proximal end is greater than a fifth height at the distal end of each cutting blade.

7. The surgical instrument of claim 1, wherein the first angle is in the range of 0 degrees to 15 degrees.

8. The surgical instrument of claim 7, wherein the second angle is in the range of 0 degrees to 15 degrees.

9. The surgical instrument of claim 8, wherein:
each cutting blade in the second plurality of cutting blades comprises a third gradually increasing height extending from the distal end to the proximal end such that a fourth height at the proximal end is greater than a fifth height at the distal end of each cutting blade.

10. The surgical instrument of claim 9, wherein:
each cutting blade in the first plurality of cutting blades comprises a sixth gradually increasing height extending from the distal end to the proximal end such that a seventh height at the proximal end is greater than a eighth height at the distal end of each cutting blade.

11. The surgical instrument of claim 9, wherein:
each cutting blade in the first plurality of cutting blades comprises a first height, wherein the first height is uniform from the proximal end to the distal end.

12. The surgical instrument of claim 1, wherein:
the distal end includes a first horizontal width;
the proximal end includes a second horizontal width; and
the first horizontal width is greater than the second horizontal width such that the body includes a width that tapers from the distal end to the proximal end.

13. The surgical instrument of claim 1, further comprising an attachment mechanism, wherein the attachment mechanism is coupled to the proximal end and configured to couple the body to a sagittal saw.

14. A surgical instrument, comprising:
a single solid body comprising a distal end, a proximal end, a first side, a second side, a bottom surface, a top surface, and a reference plane between the bottom surface and the top surface; wherein:
the bottom surface includes a bottom slope that extends downward and away from the reference plane and along a single plane from the distal end to the proximal end; and
the top surface includes a top slope that extends upward and away from the reference plane and along a single plane from the distal end to the proximal end;
a first plurality of rows of cutting blades spaced apart and positioned on the top surface, wherein each row of the first plurality of rows of cutting blades comprises a single cutting blade, wherein the cutting blade:
extends away from the top surface,
extends along the top surface from the first side to the second side,
comprises a blade plane that bisects the cutting blade from the first side to the second side, wherein the blade plane defines a first angle relative to the top surface;
a second plurality of rows of cutting blades spaced apart and positioned on the bottom surface, wherein each row of the second plurality of cutting blades comprises a single cutting blade, wherein the cutting blade:
extends away from the bottom surface,
extends along the bottom surface from the first side to the second side,
comprises a blade plane that bisects the blade from the first side to the second side, wherein the blade plane defines a second angle relative to the bottom surface.

15. The surgical instrument of claim 14, wherein:
the first angle is in the range of 0 degrees to 15 degrees and the second angle is in the range of 0 degrees to 15 degrees.

16. The surgical instrument of claim 15, wherein:
each cutting blade in the first plurality of cutting blades comprises a first height.

17. The surgical instrument of claim 16, wherein:
each of the rows of the first plurality of cutting blades comprise gradually increasing heights from a third height at the distal end to a fourth height at the proximal end.

18. The surgical instrument of claim 16, wherein:
each cutting blade in the second plurality of cutting blades comprises a fifth height.

19. The surgical instrument of claim 17, wherein:
each cutting blade in the second plurality of cutting blades comprises a fifth height.

20. The surgical instrument of claim 14, further comprising an attachment mechanism, wherein the attachment mechanism is coupled to the proximal end and configured to couple the body to a sagittal saw.

* * * * *